US007348171B2

(12) United States Patent
Pierce et al.

(10) Patent No.: US 7,348,171 B2
(45) Date of Patent: Mar. 25, 2008

(54) N-ACETYLGLUCOSAMINYLTRANSFERASE VB CODING SEQUENCES, RECOMBINANT CELLS AND METHODS

(75) Inventors: James M. Pierce, Athens, GA (US); Maria Kamar, Athens, GA (US); Jin-Kyu Lee, Snellville, GA (US); Mika Kaneko, Yamagata (JP)

(73) Assignee: University of Georgia Research Foundation, Inc., Athens, GA (US)

( * ) Notice: Subject to any disclaimer, the term of this patent is extended or adjusted under 35 U.S.C. 154(b) by 275 days.

(21) Appl. No.: 10/972,053

(22) Filed: Oct. 22, 2004

(65) Prior Publication Data
US 2005/0255489 A1 Nov. 17, 2005

Related U.S. Application Data

(63) Continuation-in-part of application No. PCT/US03/12759, filed on Apr. 23, 2003.

(60) Provisional application No. 60/375,172, filed on Apr. 23, 2002.

(51) Int. Cl.
C12N 9/12 (2006.01)
C12N 1/20 (2006.01)
C12N 15/00 (2006.01)
C07H 21/04 (2006.01)

(52) U.S. Cl. ............... 435/193; 435/194; 435/252.3; 435/320.1; 536/23.2

(58) Field of Classification Search ............... 435/193, 435/194, 252.3, 320.1; 536/23.2
See application file for complete search history.

(56) References Cited

U.S. PATENT DOCUMENTS

| 5,032,519 | A | 7/1991 | Paulson et al. |
| 5,602,003 | A | 2/1997 | Pierce et al. |
| 5,605,807 | A | 2/1997 | Dennis |
| 6,015,701 | A | 1/2000 | Pierce et al. |
| 2004/0081980 | A1* | 4/2004 | Sanjanwala et al. ......... 435/6 |
| 2004/0142363 | A1 | 7/2004 | Korczak et al. |

FOREIGN PATENT DOCUMENTS

| EP | 0 585 109 A2 | 3/1994 |
| EP | 0 905 232 A1 | 3/1999 |
| EP | 1 460 134 A1 | 9/2004 |
| EP | 1 568 775 A1 | 8/2005 |
| WO | WO 00/08171 | 2/2000 |
| WO | WO 02/46426 A2 | 6/2002 |
| WO | WO 03/060131 A1 | 12/2002 |
| WO | WO 03/091402 | 11/2003 |
| WO | WO 2004/074461 A2 | 9/2004 |

OTHER PUBLICATIONS

Nishio et al. (Oct. 1995) "Identification and Characterization of a Gene Regulating Enzymatic Glycosylation which is Induced by Diabetes and Hyperglycemia Specifically in Rat Cardiac Tissue," *J. Clin. Invest.* 96:1759-1767.
Nogare et al. (1998) "Conserved Sequences in Enzymes of the UDP-GlcNAc/MurNAc Family are Essential in Hamster UDP-GlcNAc:dolichol-P GlcNAc-1-P Transferase," *Glycobiology* 8(6):625-632.
Oppenheimer et al. (Jan. 1981) "Purification and characterization of a rabbit liver alpha 1 goes to 3 mannoside beta 1 goes to 2 N-acetylglucosaminyltransferase," *J. Biol. Chem.* 256:799-804.
Park et al. (1999) "Characterization of UDP-N-Acetylglucosamine:alpha-6-d-Mannoside beta-1, 6-N-acetylglucosaminyltransferase V from a Human Hepatoma Cell Line Hep3B," *Arch. Biochem. Biophys.* 367(2):281-288.
Priatel et al. (1997) "Isolation, Characterization and Inactivation of the Mouse Mgat3 Gene: The Bisecting N-Acetylglucosamine in Asparagine-Linked Oligosaccharides Appears Dispensable for Viability and Reproduction," *Glycobiology* 7(1):45-56.
Saito et al. (May 2002) "A Secreted Type of β1, 6-N-Acetylglucosaminyltransferase V (GnT-V) Induces Tumor Angiogenesis Without Mediation of Glycosylation: A Novel Function of GnT-V Distinct from the Original Glycosyltransferase Activity," *J. Biol. Chem.* 277(19):17002-17008.
Saito et al. (Jan. 1994) "cDNA Cloning and Chromosomal Mapping of Human N-acetylglucosaminyltransferase V+," *Biochem. Biophys. Res. Commun.* 198(1):318-327.
Schwientek et al. (Feb. 1999) "Control of O-Glycan Branch Formation," *J. Biol. Chem.* 274(8):4504-4512.
Shoreibah et al. (Feb. 1992) "Purification and Characterization of Rat Kidney UDP-N-acetylglucosamine:α-6-D-Mannoside β-1,6-NAcetylglucoseminyltransferase," *J. Biol. Chem.* 262:2920-2927.
Shoreibah et al. (Jul. 1992) "Isolation, Characterization, and Expression of a cDNA Encoding N-Acetylglucosaminyltransferase V," *J. Biol. Chem.* 268(21):15381-15385.
Weinstein et al (Dec. 1987) "Primary structure of beta-galactoside alpha 2,6-sialyltransferase. Conversion of membrane-bound enzyme to soluble forms by cleavage of the NH2-terminal signal anchor," *J. Biol. Chem.* 262:17735-17743.
Weinstein et al (Nov. 1982) "Purification of a Gal/β1→4GlcNAc α2→6 Sialytransferase and a Gal/β1→3(4)GlcNAc α2→3 Sialytransferase to Hologeneity from Rat Liver," *J. Biol.Chem.* 257:13835-13844.
Alverez et al. (2002) "Sequences of the Mouse N-Acetylglucosaminyltransferase V (Mgat5) mRNA and an mRNA Expressed by an Mgat5-Deficient Cell Line," *Glycobiology* 12(7):389-394.

(Continued)

*Primary Examiner*—Tekchand Saidha
(74) *Attorney, Agent, or Firm*—Greenlee, Winner and Sullivan, P.C.

(57) ABSTRACT

A previously unknown mammalian UDP-N-acetylglucosamine:α-6-D-mannoside β-1,6-N-acetylglucosaminyltransferase (termed GlcNAc T-Vb herein) coding sequence, protein, recombinant host cells and antibodies which specifically bind GlcNAc T-Vb are described. GlcNAc T-Vb is encoded on human chromosome 17, whereas the prior GlcNAc T-V is encoded on human chromosome 2.

20 Claims, 1 Drawing Sheet

OTHER PUBLICATIONS

Bendiak et al. (Apr. 1987) "Control of glycoprotein synthesis. Purification of UDP-N-acetylglucosamine:alpha-D-mannoside beta 1-2 N- acetylglucosaminyltransferase II from rat liver," *J. Biol. Chem.* 262:5775-5783.

Buckhaults et al. (Aug. 1997) "Transcriptional regulation of N-acetylglucosaminyltransferase V by the src Oncogene," *J. Biol. Chem.* 272(31):19575-19581.

Chen et al (1995) "Preparation of Antisera to Recombinant, Soluble N-acetylglucosaminyltransferase V and its Visualization in situ," *Glycoconjugate J.12*:813-823.

Chou et al. (Nov. 1996) "*N*-Acetylglucosaminyl Transferase Regulates the Expression of the Sulfolucuronyl Glycolipids in Specific Cell Types in Cerebellum During Development," *J. Biol. Chem.* 271(46):28868-28874.

Cummings et al. (Nov. 1982) "A mouse lymphoma cell line resistant to the leukoagglutinating lectin from *Phaseolus vulgaris* is deficient in UDP-GlcNAc: alpha-D-mannoside beta 1,6 N-acetylglucosaminyltransferase," *J. Biol. Chem.* 257:13421-13427.

Demetriou et al. (Jul. 1995) "Reduced Contact-Inhibition and Substratum Adhesion in Epithelial Cells Expressing GlcNAc-Transferase V," *L. Cell Biol.* 130(2):383-392.

Dennis et al. (1999) "Glycoprotein Glycosylation and Cancer Progression," *Biochim. Biophys. Acta 1473*:21-34.

Hagen et al. (Oct. 1998) "Cloning and Expression of a Novel, Tissue Specifically Expressed Member of the UDP-GalNAc:Polypeptide *N*-Acetylgalactosaminyltransferase Family," *J. Biol. Chem.* 273(42):27749-27754.

Huang et al. (1998) "Characterization of Multiple Transcripts of the Hamster Dolichol-P-Dependent N-Acetylglucosamine-1-P Transferase Suggests Functionally Complex Expression," *Mol. Cell Biochem.* 181:97-106.

Ihara et al. (May 2002) "Prometastic Effect of N-Acetlyglucosaminyltransferase V is die to Modification and Stabilization of Active Matriptase by Adding Beta 1-6 GlcNAc Branching," *J. Biol. Chem.* 277(19):16960-16967.

Inamori et al. (Oct. 2003) "Molecular Cloning and Characterization of Human Gn-IX, A Novel β1,6-*N*-Acetylglucosaminyltransferase That is Specifically Expressed in the Brain," *J. Biol. Chem.* 278(44):43102-43109.

Korczak et al. (2000) "Minimal Catalytic Domain of N-Acetylglucosaminyltransferase V," *Glycobiology* 10(6):595-599.

Larsen et al. (Sep. 1990) "Molecular Cloning, Sequence, and Expression of a Human GDP-L-Fucose: β-D-Galactoside 2-α-L-Fucosyltransferase cDNA that can Form the H Blood Group Antigen," *Proc. Natl. Acad. Sci. USA* 87:6674-6678.

Larsen et al. (Nov. 1989) "Isolation of a cDNA Encoding a Murine UDPgalactose:β-D-galactosyl-1,4-N-acetyl-D-glucosaminide α-1,3-galactosyltransferase: Expression Cloning by Gene Transfer," *Proc. Natl. Acad. Sci. USA* 86:8227-8231.

Mattila et al. (Oct. 1998) "The Centrally Acting β1,6*N*-Acetylglucosaminyltransferase (GlcNAc to Gal)," *J. Biol. Chem.* 273(42):27633-27639.

NCBI Annotation Project Nov. 18, 2002 Accession # XM 203356 "Mus Muscles similar to Hypothetical Protein DKFZp761J107.1 mRNA."

Kaneko et. al., (Oct. 30, 2003) "A novel β(1,6)-*N*-acetylglucosaminyltransferase V (GnT-VB)" *FEBS Letters* 554:515-519.

Strausberg, Robert, May 16, 2001, "602724070F1 NIH_MGC_113 *Homo sapiens* cDNA clone IMAGE:4850465 5', mRNA sequence," Database Accession No. BG745494.

Li, W.B., Gruber, C., Jessee, J., and Polayes, D., Feb. 11, 2001, "human full-length cDNA 5-prime end of clone CS0DC0025YH15 of Neuroblastoma COT 25-Normalized of *Homo sapiens* (human)," Database Accession No. AL524151.

Strausberg, Robert, Oct. 21, 2001, "603181442F1 NIH_MGC_121 *Homo sapiens* cDNA clone IMAGE:5245403 5', mRNA sequence," Database Accession No. Bl917052.

Drmanac, R.T., Liu, C, and Tang, Y.T., Feb. 13, 2002, "DNA encoding novel human diagnostic protein #6297," Database Accession No. AAS70493.

Drmanac, R.T., Liu, C, and Tang, Y.T., Feb. 13, 2002, "Novel human diagnostic protein #6297," Database Accession No. ABG06306.

Venter, C.J., Adams, M.C., Li, P.W., and Myers, E.W., Feb. 3, 2004, "Sequence 10516 from Patent WO02068579," Database Accession No. CQ724582.

Tang, T.Y., Wang, J., Wang, Z.W., Zhang, J., Ren, F., Zhou, P., May, Y., Ghosh, M., Xue, A., Asundi, V., Zhao, Q., Wang, D., Goodrich, R., Chen, R., Wehrman, T., Weng, G., and Boyle, B., Aug. 11, 2005, "Novel human polypeptide SEQ ID No. 644," Database Accession No. AEA19950.

Tang, T.Y., Wang, J., Wang, Z.W., Zhang, J., Ren, F., Zhou, P., May, Y., Ghosh, M., Xue, A., Asundi, V., Zhao, Q., Wang, D., Goodrich, R., Chen, R., Wehrman, T., Weng, G., and Boyle, B., Aug. 11, 2005, "Novel human polynucleotide No. 77," Database Accession No. AEA19383.

Tang, Y.T., Yang, Y., Wang, Z., Weng, G., and Ma Y., Feb. 12, 2004, "Human contig polynucleotide sequence SEQ ID No.:2392," Database Accession No. ADF60025.

Wu, T.D., and Zhou, Y., Oct. 7, 2004, "Human tumour-associated antienic target (TAT) cDNA sequence #2329," Database Accession No. ADQ85515.

Supplementary European Search Report in EP 03 72 4215, Apr. 10, 2007 (application related in subject matter to present application).

\* cited by examiner

SEQUENCE LISTING

<160> NUMBER OF SEQ ID NOS: 12

<210> SEQ ID NO 1
<211> LENGTH: 2557
<212> TYPE: DNA
<213> ORGANISM: Homo sapiens

<400> SEQUENCE: 1

```
gccagcatct tgtagttgag ctctctttat cctatagtgg gggggccctc ctgggtctgg      60
agctcagccc ccatcctttc attctccctt gcttccttca ctcatgcact cattcgtaaa     120
acatttgtgc agccggtacg tggtggagcg tcagggcacg atggcccttc ctgccctcct     180
gacccgcctc cttcctctcc gcaggctttt tgtcctgggc atcggcttct tcactctctg     240
cttcctgatg acgtctctgg gaggccagtt ctcggcccgg cgcctggggg actcgccatt     300
caccatccgc acagaagtga tggggggccc cgagtcccgc ggcgtcctgc gcaagatgag     360
cgacctgctg gagctgatgg tgaagcgcat ggacgcactg gccaggctgg agaacagcag     420
tgagctgcac cgggccggcg cgacctgca cttttcccgca gacaggatgc ccctggggc     480
cggcctcatg gagcggatcc aggctattgc ccagaacgtc tccgacatcg ctgtgaaggt     540
ggaccagatc ctgcgccaca gtctgctcct gcacagcaag gtgtcagaag gcggcggga     600
ccagtgtgag gcacccagtg accccaagtt ccctgactgc tcagggaagg tggagtggat     660
gcgtgcccgc tggacctctg accctgcta cgccttcttt ggggtggacg caccgagtg     720
ctccttcctc atctacctca gtgaggtcga gtggttctgc ccccgctgc cctggaggaa     780
ccagacggct gccagagggg cacccaagcc cctccccaaa gtccaggcag ttttccgaag     840
caacctgtcc caccttctgg acctgatggg cagcgggaag gagtccctga tcttcatgaa     900
gaagcggacc aagaggctca cagcccagtg gcgctggct gcccagcgcc tggcacagaa     960
gctgggggcc acccagaggg accagaagca gatcctggtc cacatcggct tcctgacgga    1020
ggagtccggg gacgtgttca gccctcgggt cctgaagggc gggcccctag ggagatggt    1080
gcagtgggcg gacattctga ctgcactcta tgtcctgggc catggcctgc gggtcacagt    1140
ctccctgaag gagctgcaga gtaacttagg ggtaccgcca ggccgcggaa gctgcccgct    1200
caccatgccc ctgcccttcg acctcatcta caccgactac cacggcctgc agcagatgaa    1260
gcggcacatg ggactctcct tcaagaagta ccggtgccga atcagggtca tcgacacctt    1320
cgggacggaa cctgcgtaca accacgagga gtacgccacg ctgcacggct accggaccaa    1380
ctggggctac tggaacctca cccccaagca gttcatgacc atgtttcctc ataccccga    1440
caactccttc atgggcttcg tgtccgagga gctcaacgag acgagaagc ggctcatcaa    1500
aggcggcaag gccagcaaca tggccgtggt gtacggcaag gaggcgagca tctggaaggg    1560
gaaggagaag ttcctgggca tcctgaacaa atacatggag atccatggca ccgtgtacta    1620
cgagagccag cggccccccg aggtgccagc ctttgtgaag aaccacggcc tcttaccgca    1680
gcctgagttt cagcagctgc tgcgcaaggc caaactcttc atcgggtttg gcttcccta    1740
cgagggcccc gccccctgg aggccatcgc caatggttgc atcttcctgc agtcccgctt    1800
cagcccgccc cacagctccc tcaaccacga gttcttccga ggcaagccca cctcagaga    1860
ggtgttctcc cagcatccct acgcggagaa cttcatcggc aagcccacg tgtggacagt    1920
cgactacaac aactcagagg agtttgaagc agccatcaag gccattatga gaactcaggt    1980
agacccctac ctaccctacg agtacacctg cgaggggatg ctggagcgga tccacgccta    2040
```

```
catccagcac caggacttct gcagagctcc agaccctgcc ctaccagagg cccacgcccc    2100
gcagagcccc tttgtcctgg cccccaatgc cacccacctc gagtgggctc ggaacaccag    2160
cttggctcct ggggcctggc ccccgcgca cgccctgcgg gcctggctgg ccgtgcctgg    2220
gagggcctgc accgacacct gcctggacca cgggctaatc tgtgagccct ccttcttccc    2280
cttcctgaac agccaggacg ccttcctcaa gctgcaggtg ccctgtgaca gcaccgagtc    2340
ggagatgaac cacctgtacc cggcgttcgc ccagcctggc caggagtgct acctgcagaa    2400
ggagcctctg ctcttcagct gcgccggctc caacaccaag taccgccggc tctgcccctg    2460
ccgcgacttc cgcaagggcc aggtggcctt gtgccagggc tgtctgtgaa tccgcctctg    2520
ccgccctgcc tggcacccac gctggctctc tcctgcc                             2557
```

<210> SEQ ID NO 2
<211> LENGTH: 782
<212> TYPE: PRT
<213> ORGANISM: Homo sapiens

<400> SEQUENCE: 2

```
Met Ala Leu Pro Ala Leu Leu Thr Arg Leu Leu Pro Leu Arg Arg Leu
 1               5                  10                  15

Phe Val Leu Gly Ile Gly Phe Phe Thr Leu Cys Phe Leu Met Thr Ser
                20                  25                  30

Leu Gly Gly Gln Phe Ser Ala Arg Arg Leu Gly Asp Ser Pro Phe Thr
            35                  40                  45

Ile Arg Thr Glu Val Met Gly Gly Pro Glu Ser Arg Gly Val Leu Arg
        50                  55                  60

Lys Met Ser Asp Leu Leu Glu Leu Met Val Lys Arg Met Asp Ala Leu
 65                  70                  75                  80

Ala Arg Leu Glu Asn Ser Ser Glu Leu His Arg Ala Gly Gly Asp Leu
                85                  90                  95

His Phe Pro Ala Asp Arg Met Pro Pro Gly Ala Gly Leu Met Glu Arg
            100                 105                 110

Ile Gln Ala Ile Ala Gln Asn Val Ser Asp Ile Ala Val Lys Val Asp
        115                 120                 125

Gln Ile Leu Arg His Ser Leu Leu His Ser Lys Val Ser Glu Gly
        130                 135                 140

Arg Arg Asp Gln Cys Glu Ala Pro Ser Asp Pro Lys Phe Pro Asp Cys
145                 150                 155                 160

Ser Gly Lys Val Glu Trp Met Arg Ala Arg Trp Thr Ser Asp Pro Cys
                165                 170                 175

Tyr Ala Phe Phe Gly Val Asp Gly Thr Glu Cys Ser Phe Leu Ile Tyr
            180                 185                 190

Leu Ser Glu Val Glu Trp Phe Cys Pro Pro Leu Pro Trp Arg Asn Gln
        195                 200                 205

Thr Ala Ala Gln Arg Ala Pro Lys Pro Leu Pro Lys Val Gln Ala Val
    210                 215                 220

Phe Arg Ser Asn Leu Ser His Leu Leu Asp Leu Met Gly Ser Gly Lys
225                 230                 235                 240

Glu Ser Leu Ile Phe Met Lys Lys Arg Thr Lys Arg Leu Thr Ala Gln
                245                 250                 255

Trp Ala Leu Ala Ala Gln Arg Leu Ala Gln Lys Leu Gly Ala Thr Gln
            260                 265                 270

Arg Asp Gln Lys Gln Ile Leu Val His Ile Gly Phe Leu Thr Glu Glu
```

-continued

```
                275                 280                 285
Ser Gly Asp Val Phe Ser Pro Arg Val Leu Lys Gly Gly Pro Leu Gly
    290                 295                 300
Glu Met Val Gln Trp Ala Asp Ile Leu Thr Ala Leu Tyr Val Leu Gly
305                 310                 315                 320
His Gly Leu Arg Val Thr Val Ser Leu Lys Glu Leu Gln Ser Asn Leu
                325                 330                 335
Gly Val Pro Pro Gly Arg Gly Ser Cys Pro Leu Thr Met Pro Leu Pro
            340                 345                 350
Phe Asp Leu Ile Tyr Thr Asp Tyr His Gly Leu Gln Gln Met Lys Arg
        355                 360                 365
His Met Gly Leu Ser Phe Lys Lys Tyr Arg Cys Arg Ile Arg Val Ile
    370                 375                 380
Asp Thr Phe Gly Thr Glu Pro Ala Tyr Asn His Glu Glu Tyr Ala Thr
385                 390                 395                 400
Leu His Gly Tyr Arg Thr Asn Trp Gly Tyr Trp Asn Leu Asn Pro Lys
                405                 410                 415
Gln Phe Met Thr Met Phe Pro His Thr Pro Asp Asn Ser Phe Met Gly
            420                 425                 430
Phe Val Ser Glu Glu Leu Asn Glu Thr Glu Lys Arg Leu Ile Lys Gly
        435                 440                 445
Gly Lys Ala Ser Asn Met Ala Val Val Tyr Gly Lys Glu Ala Ser Ile
    450                 455                 460
Trp Lys Gly Lys Glu Lys Phe Leu Gly Ile Leu Asn Lys Tyr Met Glu
465                 470                 475                 480
Ile His Gly Thr Val Tyr Tyr Glu Ser Gln Arg Pro Pro Glu Val Pro
                485                 490                 495
Ala Phe Val Lys Asn His Gly Leu Leu Pro Gln Pro Glu Phe Gln Gln
            500                 505                 510
Leu Leu Arg Lys Ala Lys Leu Phe Ile Gly Phe Gly Phe Pro Tyr Glu
        515                 520                 525
Gly Pro Ala Pro Leu Glu Ala Ile Ala Asn Gly Cys Ile Phe Leu Gln
    530                 535                 540
Ser Arg Phe Ser Pro Pro His Ser Ser Leu Asn His Glu Phe Phe Arg
545                 550                 555                 560
Gly Lys Pro Thr Ser Arg Glu Val Phe Ser Gln His Pro Tyr Ala Glu
                565                 570                 575
Asn Phe Ile Gly Lys Pro His Val Trp Thr Val Asp Tyr Asn Asn Ser
            580                 585                 590
Glu Glu Phe Glu Ala Ala Ile Lys Ala Ile Met Arg Thr Gln Val Asp
        595                 600                 605
Pro Tyr Leu Pro Tyr Glu Tyr Thr Cys Glu Gly Met Leu Glu Arg Ile
    610                 615                 620
His Ala Tyr Ile Gln His Gln Asp Phe Cys Arg Ala Pro Asp Pro Ala
625                 630                 635                 640
Leu Pro Glu Ala His Ala Pro Gln Ser Pro Phe Val Leu Ala Pro Asn
                645                 650                 655
Ala Thr His Leu Glu Trp Ala Arg Asn Thr Ser Leu Ala Pro Gly Ala
            660                 665                 670
Trp Pro Pro Ala His Ala Leu Arg Ala Trp Leu Ala Val Pro Gly Arg
        675                 680                 685
Ala Cys Thr Asp Thr Cys Leu Asp His Gly Leu Ile Cys Glu Pro Ser
    690                 695                 700
```

```
Phe Phe Pro Phe Leu Asn Ser Gln Asp Ala Phe Leu Lys Leu Gln Val
705                 710                 715                 720

Pro Cys Asp Ser Thr Glu Ser Glu Met Asn His Leu Tyr Pro Ala Phe
                725                 730                 735

Ala Gln Pro Gly Gln Glu Cys Tyr Leu Gln Lys Glu Pro Leu Leu Phe
            740                 745                 750

Ser Cys Ala Gly Ser Asn Thr Lys Tyr Arg Arg Leu Cys Pro Cys Arg
        755                 760                 765

Asp Phe Arg Lys Gly Gln Val Ala Leu Cys Gln Gly Cys Leu
    770                 775                 780

<210> SEQ ID NO 3
<211> LENGTH: 3370
<212> TYPE: DNA
<213> ORGANISM: Mus musculus
<220> FEATURE:
<221> NAME/KEY: CDS
<222> LOCATION: (369)..(2744)

<400> SEQUENCE: 3
ggcgcccgcc gcgggaagcc cgtttgcgcg ccgcggcgcc gtcccgccca gccagcgagc    60
ctagcaggca gacgcgcggc cggcgatctg ggggcgcgcc gcctcgcctt ccccaaaatg   120
tgaatcgggg agggcggaga cgcagagagc gcccggcccc aagctctcgc cgaacccctg   180
ccctgcgcgc ccaggccgcg ccgtgccccg cgcggggctg cagagccacc gtgccccgcg   240
ctccctcggt gctgcgaccc cccggcttcg gcccgcagcg gcttcgtggt tcccgaggcg   300
gtcagagccg ggcccaggac ggtgcgtccg gcctcgcccc cggcttctcg cccagacaag   360
``` tttgaaca atg atc aca gtc aac cca gat ggg aag ata atg gtc aga aga      410
         Met Ile Thr Val Asn Pro Asp Gly Lys Ile Met Val Arg Arg
           1               5                  10 tgc ctg gtc acc ctg aga ccc ttt cgg ctg ttt gtc ctg ggc atc ggc       458
Cys Leu Val Thr Leu Arg Pro Phe Arg Leu Phe Val Leu Gly Ile Gly
 15              20                  25                  30 ttc ttc act ctc tgc ttc ctg atg aca tct ttg gga ggc cag ttc tct       506
Phe Phe Thr Leu Cys Phe Leu Met Thr Ser Leu Gly Gly Gln Phe Ser
             35                  40                  45 gcc cgg cgc ctg ggg gac tcg ccc ttc acc atc cgc aca gaa gtg cca       554
Ala Arg Arg Leu Gly Asp Ser Pro Phe Thr Ile Arg Thr Glu Val Pro
         50                  55                  60 ggc agc cca gag tca cgt ggt gcc ctt cgc aag atg agc gac ctg ctg       602
Gly Ser Pro Glu Ser Arg Gly Ala Leu Arg Lys Met Ser Asp Leu Leu
     65                  70                  75 gag ctg atg gtg aag cgc atg gat atg ctg gcc agg ctg gag aat agc       650
Glu Leu Met Val Lys Arg Met Asp Met Leu Ala Arg Leu Glu Asn Ser
 80                  85                  90 agc gag ctg cac cgg act gcc agt gtg gcg cac tta gcc gca gac agg       698
Ser Glu Leu His Arg Thr Ala Ser Val Ala His Leu Ala Ala Asp Arg
 95                 100                 105                 110 ctc acc cct ggg gcc agc ctc att gaa agg atc cag gcc att gcc cag       746
Leu Thr Pro Gly Ala Ser Leu Ile Glu Arg Ile Gln Ala Ile Ala Gln
            115                 120                 125 aat gtg tct gac atc gct gtg aag gtg gac cag atc ctg cgc cac agc       794
Asn Val Ser Asp Ile Ala Val Lys Val Asp Gln Ile Leu Arg His Ser
        130                 135                 140 ctg att ctg cat agc aag gtg tct gaa ggt cgg agg gac cag tgt gaa       842
Leu Ile Leu His Ser Lys Val Ser Glu Gly Arg Arg Asp Gln Cys Glu
    145                 150                 155

-continued

| | | |
|---|---|---|
| gca ccc agt gac ccc aag ttc cct gac tgt tcc ggg aaa gtg gag tgg<br>Ala Pro Ser Asp Pro Lys Phe Pro Asp Cys Ser Gly Lys Val Glu Trp<br>160                    165                    170 | | 890 |
| atg cgc gcc cgc tgg acc tct gac ccc tgc tac gcc ttc ttt gga gta<br>Met Arg Ala Arg Trp Thr Ser Asp Pro Cys Tyr Ala Phe Phe Gly Val<br>175                    180                    185                    190 | | 938 |
| gac ggc act gag tgc tcc ttc ctc atc tac ctc agt gag gtt gag tgg<br>Asp Gly Thr Glu Cys Ser Phe Leu Ile Tyr Leu Ser Glu Val Glu Trp<br>                    195                    200                    205 | | 986 |
| ttc tgt ccc ccg ttg ccc tgg agg aac cag aca gct gcc cgg aca gcc<br>Phe Cys Pro Pro Leu Pro Trp Arg Asn Gln Thr Ala Ala Arg Thr Ala<br>210                    215                    220 | | 1034 |
| ccc aag tcc ctt ccc aga gtc cag gct gtg ttc cga agc aac ctg tcc<br>Pro Lys Ser Leu Pro Arg Val Gln Ala Val Phe Arg Ser Asn Leu Ser<br>            225                    230                    235 | | 1082 |
| cac ctc ctg gag ctg atg ggc agt ggg aag gag tcc ctc atc ttc atg<br>His Leu Leu Glu Leu Met Gly Ser Gly Lys Glu Ser Leu Ile Phe Met<br>240                    245                    250 | | 1130 |
| aag aag cga acc agg cgg ttc acc gca cag tgg acc aag gct gcc aag<br>Lys Lys Arg Thr Arg Arg Phe Thr Ala Gln Trp Thr Lys Ala Ala Lys<br>255                    260                    265                    270 | | 1178 |
| tac ctg gca cag aag ctg ggg gac att cgg agg gac cag aag caa atc<br>Tyr Leu Ala Gln Lys Leu Gly Asp Ile Arg Arg Asp Gln Lys Gln Ile<br>                    275                    280                    285 | | 1226 |
| ctt gtc cac att ggc ttc ctg aca gag gag tct ggg gac gtg ttc agc<br>Leu Val His Ile Gly Phe Leu Thr Glu Glu Ser Gly Asp Val Phe Ser<br>290                    295                    300 | | 1274 |
| cca agg gta ctg aag ggc ggg cct ctg gga gag atg gta cag tgg gca<br>Pro Arg Val Leu Lys Gly Gly Pro Leu Gly Glu Met Val Gln Trp Ala<br>            305                    310                    315 | | 1322 |
| gac atc ctg gct gct ctc tac gtg ctg ggc cat agc ctg cgg atc aca<br>Asp Ile Leu Ala Ala Leu Tyr Val Leu Gly His Ser Leu Arg Ile Thr<br>320                    325                    330 | | 1370 |
| gtc tcc ctg aag gag ctg cag agt aac tta ggg gtg ccg cca ggc cgg<br>Val Ser Leu Lys Glu Leu Gln Ser Asn Leu Gly Val Pro Pro Gly Arg<br>335                    340                    345                    350 | | 1418 |
| ggg aac tgc cca ctc acc gta cct ctg cct ttt gac ctc atc tac acg<br>Gly Asn Cys Pro Leu Thr Val Pro Leu Pro Phe Asp Leu Ile Tyr Thr<br>                    355                    360                    365 | | 1466 |
| gac tat cac ggc ttg cag cag atg aaa cag cac atg gga ctg tcc ttc<br>Asp Tyr His Gly Leu Gln Gln Met Lys Gln His Met Gly Leu Ser Phe<br>370                    375                    380 | | 1514 |
| aag aag tac cgg tgc aga atc cga gtc atc gac acc ttt ggg acg gag<br>Lys Lys Tyr Arg Cys Arg Ile Arg Val Ile Asp Thr Phe Gly Thr Glu<br>385                    390                    395 | | 1562 |
| cca gcg tac aac cac gag gag tat gcc acg ctg cac ggc tac cgg acc<br>Pro Ala Tyr Asn His Glu Glu Tyr Ala Thr Leu His Gly Tyr Arg Thr<br>400                    405                    410 | | 1610 |
| aac tgg ggt tac tgg aac ctc aac ccc aag cag ttc atg acc atg ttc<br>Asn Trp Gly Tyr Trp Asn Leu Asn Pro Lys Gln Phe Met Thr Met Phe<br>415                    420                    425                    430 | | 1658 |
| cct cac acc cca gac aac tcc ttc atg ggc ttc gtg tcc gag gag ctc<br>Pro His Thr Pro Asp Asn Ser Phe Met Gly Phe Val Ser Glu Glu Leu<br>                    435                    440                    445 | | 1706 |
| aat gag acc gag aag cag ctc atc aaa gat ggc aag gcc agc aac atg<br>Asn Glu Thr Glu Lys Gln Leu Ile Lys Asp Gly Lys Ala Ser Asn Met<br>450                    455                    460 | | 1754 |
| gcg gtg gtg tac ggc aag gag gcg agt atc tgg aag gtg agc aag gag<br>Ala Val Val Tyr Gly Lys Glu Ala Ser Ile Trp Lys Val Ser Lys Glu<br>465                    470                    475 | | 1802 |

```
aag ttc ctg gcc gtc ctc aac aag tac atg gag atc cac ggt acc gtg    1850
Lys Phe Leu Ala Val Leu Asn Lys Tyr Met Glu Ile His Gly Thr Val
    480                 485                 490 tac tat gag agc cag cgg cca ccc gag gtc ccc gcc ttc gtg aag aac    1898
Tyr Tyr Glu Ser Gln Arg Pro Pro Glu Val Pro Ala Phe Val Lys Asn
495                 500                 505                 510 cac ggc ctc cta ccg cag cct gag ttc cag cag ctg ctg cgg aag gcc    1946
His Gly Leu Leu Pro Gln Pro Glu Phe Gln Gln Leu Leu Arg Lys Ala
                515                 520                 525 aag ctc ttt ata ggg ttc gga ttc ccc tac gag ggc cca gca ccg ttg    1994
Lys Leu Phe Ile Gly Phe Gly Phe Pro Tyr Glu Gly Pro Ala Pro Leu
            530                 535                 540 gaa gcc att gcc aat ggc tgc atc ttc cta cag tct cgc ttc agc ccg    2042
Glu Ala Ile Ala Asn Gly Cys Ile Phe Leu Gln Ser Arg Phe Ser Pro
        545                 550                 555 ccc cac agc tcc ctc aac cac gag ttc ttc cgg ggc aag ccc acc tcc    2090
Pro His Ser Ser Leu Asn His Glu Phe Phe Arg Gly Lys Pro Thr Ser
    560                 565                 570 agg gag gtg ttc tcc cag cat ccg tat gca gag aac ttt att ggc aag    2138
Arg Glu Val Phe Ser Gln His Pro Tyr Ala Glu Asn Phe Ile Gly Lys
575                 580                 585                 590 ccg cac gtg tgg acc gtg gac tat aac aac tcc gat gag ttt gaa aca    2186
Pro His Val Trp Thr Val Asp Tyr Asn Asn Ser Asp Glu Phe Glu Thr
                595                 600                 605 gcc att aag gcc atc atg aac acc cag gta gac cca tat ctg ccc tat    2234
Ala Ile Lys Ala Ile Met Asn Thr Gln Val Asp Pro Tyr Leu Pro Tyr
            610                 615                 620 gaa tat acc tgt gca ggg atg ctg gaa cgg atc aat gcc tac atc caa    2282
Glu Tyr Thr Cys Ala Gly Met Leu Glu Arg Ile Asn Ala Tyr Ile Gln
        625                 630                 635 cac cag gac ttc tgt gtg ggt cca agc cct ctt cca cca ggg gcc agc    2330
His Gln Asp Phe Cys Val Gly Pro Ser Pro Leu Pro Pro Gly Ala Ser
    640                 645                 650 act gcc cag agt cca ttt gtc tta gct cct aat gca act cat ctc gag    2378
Thr Ala Gln Ser Pro Phe Val Leu Ala Pro Asn Ala Thr His Leu Glu
655                 660                 665                 670 tgg gcc cag aac atc agc tca gtt ccg gga gcc tgg ccc cct acc cac    2426
Trp Ala Gln Asn Ile Ser Ser Val Pro Gly Ala Trp Pro Pro Thr His
                675                 680                 685 tct ctg cgg gcc tgg ctg gca gcc cct gga agg gcc tgc acg gac gcc    2474
Ser Leu Arg Ala Trp Leu Ala Ala Pro Gly Arg Ala Cys Thr Asp Ala
            690                 695                 700 tgc ctg gac cat gga ttg atc tgc gag cct tcc ttc ttc cct ttc ctc    2522
Cys Leu Asp His Gly Leu Ile Cys Glu Pro Ser Phe Phe Pro Phe Leu
        705                 710                 715 aac agc cag aat tcg ttc ctc aag ctg cag gtg ccc tgt gac agc act    2570
Asn Ser Gln Asn Ser Phe Leu Lys Leu Gln Val Pro Cys Asp Ser Thr
    720                 725                 730 gag tgg gag atg cat cac ttg tac cct gcc ttt gcc caa ccc ggc caa    2618
Glu Trp Glu Met His His Leu Tyr Pro Ala Phe Ala Gln Pro Gly Gln
735                 740                 745                 750 gag tgc tac cta caa aaa gag cca ctg ctc ttc agc tgt gct ggt gcc    2666
Glu Cys Tyr Leu Gln Lys Glu Pro Leu Leu Phe Ser Cys Ala Gly Ala
                755                 760                 765 agc acc aag tac cag agg ctc tgc ccc tgc cgt gac ttc cgc aag ggt    2714
Ser Thr Lys Tyr Gln Arg Leu Cys Pro Cys Arg Asp Phe Arg Lys Gly
            770                 775                 780 cag gtg gcc ttg tgc cag ggc tgc ctg tga ggccggagcc accctgccca     2764
Gln Val Ala Leu Cys Gln Gly Cys Leu
```

-continued

```
                785                 790
gaacctgccc acccgcacgt ggttggcaag caccagcact ttctgagctc cggtcacgct    2824
cactacgtgt cccctggctg cagcctcccc tggccaggga tgggaagagg aagctgagga    2884
gacagcagct ccaggcctgc agctccctcc tagggcttc cttgcctcgc ataggacct     2944 gaggccaagc atgtgggctg acctccctgt cgggtgtacc caggagcacg tggatgaga    3004 tccctggctt tctgaggtct ggaccagctg gagatgtggc cttgaccatg cttggaccca    3064
gcataggcct tttgatccac aaggctggga gcatggccat gccgcccct attcaccaga    3124 ggtctcaagg gatagggaac aggtcacagc cacacttgct gtgagggcca cccctcaca    3184 tgaggcaaca gttcacgcag ggccagtcca gcctcctcag ttgcttgggg gggggggga    3244 acgacaaagg gacagagagc tcagggaggc tagtgcccct ccctgttgct caaccctgct    3304
tcctccagca gacttccctc tgggcctctc ctgacaccca gttctggcat ggcctgtgac    3364
tggtcc                                                               3370
```

<210> SEQ ID NO 4
<211> LENGTH: 791
<212> TYPE: PRT
<213> ORGANISM: Mus musculus

<400> SEQUENCE: 4

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
            20                  25                  30

Thr Leu Cys Phe Leu Met Thr Ser Leu Gly Gly Gln Phe Ser Ala Arg
        35                  40                  45

Arg Leu Gly Asp Ser Pro Phe Thr Ile Arg Thr Glu Val Pro Gly Ser
    50                  55                  60

Pro Glu Ser Arg Gly Ala Leu Arg Lys Met Ser Asp Leu Leu Glu Leu
65                  70                  75                  80

Met Val Lys Arg Met Asp Met Leu Ala Arg Leu Glu Asn Ser Ser Glu
                85                  90                  95

Leu His Arg Thr Ala Ser Val Ala His Leu Ala Ala Asp Arg Leu Thr
            100                 105                 110

Pro Gly Ala Ser Leu Ile Glu Arg Ile Gln Ala Ile Ala Gln Asn Val
        115                 120                 125

Ser Asp Ile Ala Val Lys Val Asp Gln Ile Leu Arg His Ser Leu Ile
    130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Glu Trp Met Arg
                165                 170                 175

Ala Arg Trp Thr Ser Asp Pro Cys Tyr Ala Phe Gly Val Asp Gly
            180                 185                 190

Thr Glu Cys Ser Phe Leu Ile Tyr Leu Ser Glu Val Glu Trp Phe Cys
        195                 200                 205

Pro Pro Leu Pro Trp Arg Asn Gln Thr Ala Ala Arg Thr Ala Pro Lys
    210                 215                 220

Ser Leu Pro Arg Val Gln Ala Val Phe Arg Ser Asn Leu Ser His Leu
225                 230                 235                 240

Leu Glu Leu Met Gly Ser Gly Lys Glu Ser Leu Ile Phe Met Lys Lys
                245                 250                 255

```
Arg Thr Arg Arg Phe Thr Ala Gln Trp Thr Lys Ala Ala Lys Tyr Leu
            260                 265                 270

Ala Gln Lys Leu Gly Asp Ile Arg Arg Asp Gln Lys Gln Ile Leu Val
        275                 280                 285

His Ile Gly Phe Leu Thr Glu Glu Ser Gly Asp Val Phe Ser Pro Arg
        290                 295                 300

Val Leu Lys Gly Gly Pro Leu Gly Glu Met Val Gln Trp Ala Asp Ile
305                 310                 315                 320

Leu Ala Ala Leu Tyr Val Leu Gly His Ser Leu Arg Ile Thr Val Ser
                325                 330                 335

Leu Lys Glu Leu Gln Ser Asn Leu Gly Val Pro Pro Gly Arg Gly Asn
            340                 345                 350

Cys Pro Leu Thr Val Pro Leu Pro Phe Asp Leu Ile Tyr Thr Asp Tyr
        355                 360                 365

His Gly Leu Gln Gln Met Lys Gln His Met Gly Leu Ser Phe Lys Lys
        370                 375                 380

Tyr Arg Cys Arg Ile Arg Val Ile Asp Thr Phe Gly Thr Glu Pro Ala
385                 390                 395                 400

Tyr Asn His Glu Glu Tyr Ala Thr Leu His Gly Tyr Arg Thr Asn Trp
                405                 410                 415

Gly Tyr Trp Asn Leu Asn Pro Lys Gln Phe Met Thr Met Phe Pro His
            420                 425                 430

Thr Pro Asp Asn Ser Phe Met Gly Phe Val Ser Glu Glu Leu Asn Glu
        435                 440                 445

Thr Glu Lys Gln Leu Ile Lys Asp Gly Lys Ala Ser Asn Met Ala Val
        450                 455                 460

Val Tyr Gly Lys Glu Ala Ser Ile Trp Lys Val Ser Lys Glu Lys Phe
465                 470                 475                 480

Leu Ala Val Leu Asn Lys Tyr Met Glu Ile His Gly Thr Val Tyr Tyr
                485                 490                 495

Glu Ser Gln Arg Pro Pro Glu Val Pro Ala Phe Val Lys Asn His Gly
            500                 505                 510

Leu Leu Pro Gln Pro Glu Phe Gln Gln Leu Leu Arg Lys Ala Lys Leu
        515                 520                 525

Phe Ile Gly Phe Gly Phe Pro Tyr Glu Gly Pro Ala Pro Leu Glu Ala
        530                 535                 540

Ile Ala Asn Gly Cys Ile Phe Leu Gln Ser Arg Phe Ser Pro Pro His
545                 550                 555                 560

Ser Ser Leu Asn His Glu Phe Phe Arg Gly Lys Pro Thr Ser Arg Glu
                565                 570                 575

Val Phe Ser Gln His Pro Tyr Ala Glu Asn Phe Ile Gly Lys Pro His
            580                 585                 590

Val Trp Thr Val Asp Tyr Asn Asn Ser Asp Glu Phe Glu Thr Ala Ile
        595                 600                 605

Lys Ala Ile Met Asn Thr Gln Val Asp Pro Tyr Leu Pro Tyr Glu Tyr
        610                 615                 620

Thr Cys Ala Gly Met Leu Glu Arg Ile Asn Ala Tyr Ile Gln His Gln
625                 630                 635                 640

Asp Phe Cys Val Gly Pro Ser Pro Leu Pro Pro Gly Ala Ser Thr Ala
                645                 650                 655

Gln Ser Pro Phe Val Leu Ala Pro Asn Ala Thr His Leu Glu Trp Ala
            660                 665                 670
```

```
Gln Asn Ile Ser Ser Val Pro Gly Ala Trp Pro Pro Thr His Ser Leu
            675                 680                 685

Arg Ala Trp Leu Ala Ala Pro Gly Arg Ala Cys Thr Asp Ala Cys Leu
    690                 695                 700

Asp His Gly Leu Ile Cys Glu Pro Ser Phe Phe Pro Phe Leu Asn Ser
705                 710                 715                 720

Gln Asn Ser Phe Leu Lys Leu Gln Val Pro Cys Asp Ser Thr Glu Trp
            725                 730                 735

Glu Met His His Leu Tyr Pro Ala Phe Ala Gln Pro Gly Gln Glu Cys
        740                 745                 750

Tyr Leu Gln Lys Glu Pro Leu Leu Phe Ser Cys Ala Gly Ala Ser Thr
            755                 760                 765

Lys Tyr Gln Arg Leu Cys Pro Cys Arg Asp Phe Arg Lys Gly Gln Val
770                 775                 780

Ala Leu Cys Gln Gly Cys Leu
785                 790

<210> SEQ ID NO 5
<211> LENGTH: 28
<212> TYPE: DNA
<213> ORGANISM: Artificial
<220> FEATURE:
<223> OTHER INFORMATION: Oligonucleotide useful as a primer

<400> SEQUENCE: 5
cttcgacctc atctacaccg actaccac                                          28

<210> SEQ ID NO 6
<211> LENGTH: 28
<212> TYPE: DNA
<213> ORGANISM: Artificial
<220> FEATURE:
<223> OTHER INFORMATION: Oligonucleotide useful as a primer

<400> SEQUENCE: 6
gccaaacccg atgaagagtt tggccttg                                          28

<210> SEQ ID NO 7
<211> LENGTH: 2349
<212> TYPE: DNA
<213> ORGANISM: Homo sapiens
<220> FEATURE:
<221> NAME/KEY: CDS
<222> LOCATION: (1)..(2346)

<400> SEQUENCE: 7 atg gcc ctt cct gcc ctc ctg acc cgc ctc ctt cct ctc cgc agg ctt        48
Met Ala Leu Pro Ala Leu Leu Thr Arg Leu Leu Pro Leu Arg Arg Leu
1               5                   10                  15 ttt gtc ctg ggc atc ggc ttc ttc act ctc tgc ttc ctg atg acg tct        96
Phe Val Leu Gly Ile Gly Phe Phe Thr Leu Cys Phe Leu Met Thr Ser
                20                  25                  30 ctg gga ggc cag ttc tcg gcc cgg cgc ctg ggg gac tcg cca ttc acc       144
Leu Gly Gly Gln Phe Ser Ala Arg Arg Leu Gly Asp Ser Pro Phe Thr
            35                  40                  45 atc cgc aca gaa gtg atg ggg ggc ccc gag tcc cgc ggc gtc ctg cgc       192
Ile Arg Thr Glu Val Met Gly Gly Pro Glu Ser Arg Gly Val Leu Arg
        50                  55                  60 aag atg agc gac ctg ctg gag ctg atg gtg aag cgc atg gac gca ctg       240
Lys Met Ser Asp Leu Leu Glu Leu Met Val Lys Arg Met Asp Ala Leu
65                  70                  75                  80
```

```
gcc agg ctg gag aac agc agt gag ctg cac cgg gcc ggc ggc gac ctg      288
Ala Arg Leu Glu Asn Ser Ser Glu Leu His Arg Ala Gly Gly Asp Leu
                85                  90                  95 cac ttt ccc gca gac agg atg ccc cct ggg gcc ggc ctc atg gag cgg      336
His Phe Pro Ala Asp Arg Met Pro Pro Gly Ala Gly Leu Met Glu Arg
            100                 105                 110 atc cag gct att gcc cag aac gtc tcc gac atc gct gtg aag gtg gac      384
Ile Gln Ala Ile Ala Gln Asn Val Ser Asp Ile Ala Val Lys Val Asp
        115                 120                 125 cag atc ctg cgc cac agt ctg ctc ctg cac agc aag gtg tca gaa ggc      432
Gln Ile Leu Arg His Ser Leu Leu Leu His Ser Lys Val Ser Glu Gly
    130                 135                 140 cgg cgg gac cag tgt gag gca ccc agt gac ccc aag ttc cct gac tgc      480
Arg Arg Asp Gln Cys Glu Ala Pro Ser Asp Pro Lys Phe Pro Asp Cys
145                 150                 155                 160 tca ggg aag gtg gag tgg atg cgt gcc cgc tgg acc tct gac ccc tgc      528
Ser Gly Lys Val Glu Trp Met Arg Ala Arg Trp Thr Ser Asp Pro Cys
                165                 170                 175 tac gcc ttc ttt ggg gtg gac ggc acc gag tgc tcc ttc ctc atc tac      576
Tyr Ala Phe Phe Gly Val Asp Gly Thr Glu Cys Ser Phe Leu Ile Tyr
            180                 185                 190 ctc agt gag gtc gag tgg ttc tgc ccc ccg ctg ccc tgg agg aac cag      624
Leu Ser Glu Val Glu Trp Phe Cys Pro Pro Leu Pro Trp Arg Asn Gln
        195                 200                 205 acg gct gcc cag agg gca ccc aag ccc ctc ccc aaa gtc cag gca gtt      672
Thr Ala Ala Gln Arg Ala Pro Lys Pro Leu Pro Lys Val Gln Ala Val
    210                 215                 220 ttc cga agc aac ctg tcc cac ctt ctg gac ctg atg ggc agc ggg aag      720
Phe Arg Ser Asn Leu Ser His Leu Leu Asp Leu Met Gly Ser Gly Lys
225                 230                 235                 240 gag tcc ctg atc ttc atg aag aag cgg acc aag agg ctc aca gcc cag      768
Glu Ser Leu Ile Phe Met Lys Lys Arg Thr Lys Arg Leu Thr Ala Gln
                245                 250                 255 tgg gcg ctg gct gcc cag cgc ctg gca cag aag ctg ggg gcc acc cag      816
Trp Ala Leu Ala Ala Gln Arg Leu Ala Gln Lys Leu Gly Ala Thr Gln
            260                 265                 270 agg gac cag aag cag atc ctg gtc cac atc ggc ttc ctg acg gag gag      864
Arg Asp Gln Lys Gln Ile Leu Val His Ile Gly Phe Leu Thr Glu Glu
        275                 280                 285 tcc ggg gac gtg ttc agc cct cgg gtc ctg aag ggc ggg ccc cta ggg      912
Ser Gly Asp Val Phe Ser Pro Arg Val Leu Lys Gly Gly Pro Leu Gly
    290                 295                 300 gag atg gtg cag tgg gcg gac att ctg act gca ctc tat gtc ctg ggc      960
Glu Met Val Gln Trp Ala Asp Ile Leu Thr Ala Leu Tyr Val Leu Gly
305                 310                 315                 320 cat ggc ctg cgg gtc aca gtc tcc ctg aag gag ctg cag agt aac tta     1008
His Gly Leu Arg Val Thr Val Ser Leu Lys Glu Leu Gln Ser Asn Leu
                325                 330                 335 ggg gta ccg cca ggc cgc gga agc tgc ccg ctc acc atg ccc ctg ccc     1056
Gly Val Pro Pro Gly Arg Gly Ser Cys Pro Leu Thr Met Pro Leu Pro
            340                 345                 350 ttc gac ctc atc tac acc gac tac cac ggc ctg cag cag atg aag cgg     1104
Phe Asp Leu Ile Tyr Thr Asp Tyr His Gly Leu Gln Gln Met Lys Arg
        355                 360                 365 cac atg gga ctc tcc ttc aag aag tac cgg tgc cga atc agg gtc atc     1152
His Met Gly Leu Ser Phe Lys Lys Tyr Arg Cys Arg Ile Arg Val Ile
    370                 375                 380 gac acc ttc ggg acg gaa cct gcg tac aac cac gag gag tac gcc acg     1200
Asp Thr Phe Gly Thr Glu Pro Ala Tyr Asn His Glu Glu Tyr Ala Thr
385                 390                 395                 400
```

-continued

```
ctg cac ggc tac cgg acc aac tgg ggc tac tgg aac ctc aac ccc aag       1248
Leu His Gly Tyr Arg Thr Asn Trp Gly Tyr Trp Asn Leu Asn Pro Lys
            405                 410                 415 cag ttc atg acc atg ttt cct cat acc ccc gac aac tcc ttc atg ggc       1296
Gln Phe Met Thr Met Phe Pro His Thr Pro Asp Asn Ser Phe Met Gly
        420                 425                 430 ttc gtg tcc gag gag ctc aac gag acg gag aag cgg ctc atc aaa ggc       1344
Phe Val Ser Glu Glu Leu Asn Glu Thr Glu Lys Arg Leu Ile Lys Gly
    435                 440                 445 ggc aag gcc agc aac atg gcc gtg gtg tac ggc aag gag gcg agc atc       1392
Gly Lys Ala Ser Asn Met Ala Val Val Tyr Gly Lys Glu Ala Ser Ile
450                 455                 460 tgg aag ggg aag gag aag ttc ctg ggc atc ctg aac aaa tac atg gag       1440
Trp Lys Gly Lys Glu Lys Phe Leu Gly Ile Leu Asn Lys Tyr Met Glu
465                 470                 475                 480 atc cat ggc acc gtg tac tac gag agc cag cgg ccc ccc gag gtg cca       1488
Ile His Gly Thr Val Tyr Tyr Glu Ser Gln Arg Pro Pro Glu Val Pro
                485                 490                 495 gcc ttt gtg aag aac cac ggc ctc tta ccg cag cct gag ttt cag cag       1536
Ala Phe Val Lys Asn His Gly Leu Leu Pro Gln Pro Glu Phe Gln Gln
            500                 505                 510 ctg ctg cgc aag gcc aaa ctc ttc atc ggg ttt ggc ttc ccc tac gag       1584
Leu Leu Arg Lys Ala Lys Leu Phe Ile Gly Phe Gly Phe Pro Tyr Glu
        515                 520                 525 ggc ccc gcc ccc ctg gag gcc atc gcc aat ggt tgc atc ttc ctg cag       1632
Gly Pro Ala Pro Leu Glu Ala Ile Ala Asn Gly Cys Ile Phe Leu Gln
    530                 535                 540 tcc cgc ttc agc ccg ccc cac agc tcc ctc aac cac gag ttc ttc cga       1680
Ser Arg Phe Ser Pro Pro His Ser Ser Leu Asn His Glu Phe Phe Arg
545                 550                 555                 560 ggc aag ccc acc tcc aga gag gtg ttc tcc cag cat ccc tac gcg gag       1728
Gly Lys Pro Thr Ser Arg Glu Val Phe Ser Gln His Pro Tyr Ala Glu
                565                 570                 575 aac ttc atc ggc aag ccc cac gtg tgg aca gtc gac tac aac aac tca       1776
Asn Phe Ile Gly Lys Pro His Val Trp Thr Val Asp Tyr Asn Asn Ser
            580                 585                 590 gag gag ttt gaa gca gcc atc aag gcc att atg aga act cag gta gac       1824
Glu Glu Phe Glu Ala Ala Ile Lys Ala Ile Met Arg Thr Gln Val Asp
        595                 600                 605 ccc tac cta ccc tac gag tac acc tgc gag ggg atg ctg gag cgg atc       1872
Pro Tyr Leu Pro Tyr Glu Tyr Thr Cys Glu Gly Met Leu Glu Arg Ile
    610                 615                 620 cac gcc tac atc cag cac cag gac ttc tgc aga gct cca gac cct gcc       1920
His Ala Tyr Ile Gln His Gln Asp Phe Cys Arg Ala Pro Asp Pro Ala
625                 630                 635                 640 cta cca gag gcc cac gcc ccg cag agc ccc ttt gtc ctg gcc ccc aat       1968
Leu Pro Glu Ala His Ala Pro Gln Ser Pro Phe Val Leu Ala Pro Asn
                645                 650                 655 gcc acc cac ctc gag tgg gct cgg aac acc agc ttg gct cct ggg gcc       2016
Ala Thr His Leu Glu Trp Ala Arg Asn Thr Ser Leu Ala Pro Gly Ala
            660                 665                 670 tgg ccc ccc gcg cac gcc ctg cgg gcc tgg ctg gcc gtg cct ggg agg       2064
Trp Pro Pro Ala His Ala Leu Arg Ala Trp Leu Ala Val Pro Gly Arg
        675                 680                 685 gcc tgc acc gac acc tgc ctg gac cac ggg cta atc tgt gag ccc tcc       2112
Ala Cys Thr Asp Thr Cys Leu Asp His Gly Leu Ile Cys Glu Pro Ser
    690                 695                 700 ttc ttc ccc ttc ctg aac agc cag gac gcc ttc ctc aag ctg cag gtg       2160
Phe Phe Pro Phe Leu Asn Ser Gln Asp Ala Phe Leu Lys Leu Gln Val
```

```
                705                 710                 715                 720
ccc tgt gac agc acc gag tcg gag atg aac cac ctg tac ccg gcg ttc      2208
Pro Cys Asp Ser Thr Glu Ser Glu Met Asn His Leu Tyr Pro Ala Phe
                    725                 730                 735 gcc cag cct ggc cag gag tgc tac ctg cag aag gag cct ctg ctc ttc      2256
Ala Gln Pro Gly Gln Glu Cys Tyr Leu Gln Lys Glu Pro Leu Leu Phe
                740                 745                 750 agc tgc gcc ggc tcc aac acc aag tac cgc cgg ctc tgc ccc tgc cgc      2304
Ser Cys Ala Gly Ser Asn Thr Lys Tyr Arg Arg Leu Cys Pro Cys Arg
                    755                 760                 765 gac ttc cgc aag ggc cag gtg gcc ttg tgc cag ggc tgt ctg tga          2349
Asp Phe Arg Lys Gly Gln Val Ala Leu Cys Gln Gly Cys Leu
        770                 775                 780

<210> SEQ ID NO 8
<211> LENGTH: 782
<212> TYPE: PRT
<213> ORGANISM: Homo sapiens

<400> SEQUENCE: 8

Met Ala Leu Pro Ala Leu Leu Thr Arg Leu Leu Pro Leu Arg Arg Leu
1               5                   10                  15

Phe Val Leu Gly Ile Gly Phe Phe Thr Leu Cys Phe Leu Met Thr Ser
            20                  25                  30

Leu Gly Gly Gln Phe Ser Ala Arg Arg Leu Gly Asp Ser Pro Phe Thr
        35                  40                  45

Ile Arg Thr Glu Val Met Gly Gly Pro Glu Ser Arg Gly Val Leu Arg
    50                  55                  60

Lys Met Ser Asp Leu Leu Glu Leu Met Val Lys Arg Met Asp Ala Leu
65                  70                  75                  80

Ala Arg Leu Glu Asn Ser Ser Glu Leu His Arg Ala Gly Gly Asp Leu
                85                  90                  95

His Phe Pro Ala Asp Arg Met Pro Gly Ala Gly Leu Met Glu Arg
            100                 105                 110

Ile Gln Ala Ile Ala Gln Asn Val Ser Asp Ile Ala Val Lys Val Asp
        115                 120                 125

Gln Ile Leu Arg His Ser Leu Leu His Ser Lys Val Ser Glu Gly
    130                 135                 140

Arg Arg Asp Gln Cys Glu Ala Pro Ser Asp Pro Lys Phe Pro Asp Cys
145                 150                 155                 160

Ser Gly Lys Val Glu Trp Met Arg Ala Arg Trp Thr Ser Asp Pro Cys
                165                 170                 175

Tyr Ala Phe Phe Gly Val Asp Gly Thr Glu Cys Ser Phe Leu Ile Tyr
            180                 185                 190

Leu Ser Glu Val Glu Trp Phe Cys Pro Pro Leu Pro Trp Arg Asn Gln
        195                 200                 205

Thr Ala Ala Gln Arg Ala Pro Lys Pro Leu Pro Lys Val Gln Ala Val
    210                 215                 220

Phe Arg Ser Asn Leu Ser His Leu Leu Asp Leu Met Gly Ser Gly Lys
225                 230                 235                 240

Glu Ser Leu Ile Phe Met Lys Lys Arg Thr Lys Arg Leu Thr Ala Gln
                245                 250                 255

Trp Ala Leu Ala Ala Gln Arg Leu Ala Gln Lys Leu Gly Ala Thr Gln
            260                 265                 270

Arg Asp Gln Lys Gln Ile Leu Val His Ile Gly Phe Leu Thr Glu Glu
        275                 280                 285
```

```
Ser Gly Asp Val Phe Ser Pro Arg Val Leu Lys Gly Pro Leu Gly
    290                 295                 300

Glu Met Val Gln Trp Ala Asp Ile Leu Thr Ala Leu Tyr Val Leu Gly
305                 310                 315                 320

His Gly Leu Arg Val Thr Val Ser Leu Lys Glu Leu Gln Ser Asn Leu
                325                 330                 335

Gly Val Pro Pro Gly Arg Gly Ser Cys Pro Leu Thr Met Pro Leu Pro
                340                 345                 350

Phe Asp Leu Ile Tyr Thr Asp Tyr His Gly Leu Gln Gln Met Lys Arg
                355                 360                 365

His Met Gly Leu Ser Phe Lys Lys Tyr Arg Cys Arg Ile Arg Val Ile
    370                 375                 380

Asp Thr Phe Gly Thr Glu Pro Ala Tyr Asn His Glu Glu Tyr Ala Thr
385                 390                 395                 400

Leu His Gly Tyr Arg Thr Asn Trp Gly Tyr Trp Asn Leu Asn Pro Lys
                405                 410                 415

Gln Phe Met Thr Met Phe Pro His Thr Pro Asp Asn Ser Phe Met Gly
                420                 425                 430

Phe Val Ser Glu Glu Leu Asn Glu Thr Glu Lys Arg Leu Ile Lys Gly
    435                 440                 445

Gly Lys Ala Ser Asn Met Ala Val Val Tyr Gly Lys Glu Ala Ser Ile
    450                 455                 460

Trp Lys Gly Lys Glu Lys Phe Leu Gly Ile Leu Asn Lys Tyr Met Glu
465                 470                 475                 480

Ile His Gly Thr Val Tyr Tyr Glu Ser Gln Arg Pro Pro Glu Val Pro
                485                 490                 495

Ala Phe Val Lys Asn His Gly Leu Leu Pro Gln Pro Glu Phe Gln Gln
                500                 505                 510

Leu Leu Arg Lys Ala Lys Leu Phe Ile Gly Phe Gly Phe Pro Tyr Glu
                515                 520                 525

Gly Pro Ala Pro Leu Glu Ala Ile Ala Asn Gly Cys Ile Phe Leu Gln
                530                 535                 540

Ser Arg Phe Ser Pro Pro His Ser Ser Leu Asn His Glu Phe Phe Arg
545                 550                 555                 560

Gly Lys Pro Thr Ser Arg Glu Val Phe Ser Gln His Pro Tyr Ala Glu
                565                 570                 575

Asn Phe Ile Gly Lys Pro His Val Trp Thr Val Asp Tyr Asn Asn Ser
                580                 585                 590

Glu Glu Phe Glu Ala Ala Ile Lys Ala Ile Met Arg Thr Gln Val Asp
                595                 600                 605

Pro Tyr Leu Pro Tyr Glu Tyr Thr Cys Glu Gly Met Leu Glu Arg Ile
                610                 615                 620

His Ala Tyr Ile Gln His Gln Asp Phe Cys Arg Ala Pro Asp Pro Ala
625                 630                 635                 640

Leu Pro Glu Ala His Ala Pro Gln Ser Pro Phe Val Leu Ala Pro Asn
                645                 650                 655

Ala Thr His Leu Glu Trp Ala Arg Asn Thr Ser Leu Ala Pro Gly Ala
                660                 665                 670

Trp Pro Pro Ala His Ala Leu Arg Ala Trp Leu Ala Val Pro Gly Arg
                675                 680                 685

Ala Cys Thr Asp Thr Cys Leu Asp His Gly Leu Ile Cys Glu Pro Ser
    690                 695                 700
```

```
                            Phe Phe Pro Phe Leu Asn Ser Gln Asp Ala Phe Leu Lys Leu Gln Val
                            705                 710                 715                 720

Pro Cys Asp Ser Thr Glu Ser Glu Met Asn His Leu Tyr Pro Ala Phe
                                            725                 730                 735

Ala Gln Pro Gly Gln Glu Cys Tyr Leu Gln Lys Glu Pro Leu Leu Phe
                                        740                 745                 750

Ser Cys Ala Gly Ser Asn Thr Lys Tyr Arg Arg Leu Cys Pro Cys Arg
                                    755                 760                 765

Asp Phe Arg Lys Gly Gln Val Ala Leu Cys Gln Gly Cys Leu
                                770                 775                 780

<210> SEQ ID NO 9
<211> LENGTH: 2355
<212> TYPE: DNA
<213> ORGANISM: Homo sapiens
<220> FEATURE:
<221> NAME/KEY: CDS
<222> LOCATION: (1)..(2352)

<400> SEQUENCE: 9 atg gcc ctt cct gcc ctc ctg acc cgc ctc ctt cct ctc cgc agg ctt      48
Met Ala Leu Pro Ala Leu Leu Thr Arg Leu Leu Pro Leu Arg Arg Leu
1               5                   10                  15 ttt gtc ctg ggc atc ggc ttc ttc act ctc tgc ttc ctg atg acg tct      96
Phe Val Leu Gly Ile Gly Phe Phe Thr Leu Cys Phe Leu Met Thr Ser
            20                  25                  30 ctg gga ggc cag ttc tcg gcc cgg cgc ctg ggg gac tcg cca ttc acc     144
Leu Gly Gly Gln Phe Ser Ala Arg Arg Leu Gly Asp Ser Pro Phe Thr
        35                  40                  45 atc cgc aca gaa gtg atg ggg ggc ccc gag tcc cgc ggc gtc ctg cgc     192
Ile Arg Thr Glu Val Met Gly Gly Pro Glu Ser Arg Gly Val Leu Arg
    50                  55                  60 aag atg agc gac ctg ctg gag ctg atg gtg aag cgc atg gac gca ctg     240
Lys Met Ser Asp Leu Leu Glu Leu Met Val Lys Arg Met Asp Ala Leu
65                  70                  75                  80 gcc agg ctg gag aac agc agt gag ctg cac cgg gcc ggc ggc gac ctg     288
Ala Arg Leu Glu Asn Ser Ser Glu Leu His Arg Ala Gly Gly Asp Leu
                85                  90                  95 cac ttt ccc gca gac agg atg ccc cct ggg gcc ggc ctc atg gag cgg     336
His Phe Pro Ala Asp Arg Met Pro Pro Gly Ala Gly Leu Met Glu Arg
            100                 105                 110 atc cag gct att gcc cag aac gtc tcc gac atc gct gtg aag gtg gac     384
Ile Gln Ala Ile Ala Gln Asn Val Ser Asp Ile Ala Val Lys Val Asp
        115                 120                 125 cag atc ctg cgc cac agt ctg ctc ctg cac agc aag gtg tca gaa ggc     432
Gln Ile Leu Arg His Ser Leu Leu Leu His Ser Lys Val Ser Glu Gly
    130                 135                 140 cgg cgg gac cag tgt gag gca ccc agt gac ccc aag ttc cct gac tgc     480
Arg Arg Asp Gln Cys Glu Ala Pro Ser Asp Pro Lys Phe Pro Asp Cys
145                 150                 155                 160 tca ggg aag gtg gag tgg atg cgt gcc cgc tgg acc tct gac ccc tgc     528
Ser Gly Lys Val Glu Trp Met Arg Ala Arg Trp Thr Ser Asp Pro Cys
                165                 170                 175 tac gcc ttc ttt ggg gtg gac ggc acc gag tgc tcc ttc ctc atc tac     576
Tyr Ala Phe Phe Gly Val Asp Gly Thr Glu Cys Ser Phe Leu Ile Tyr
            180                 185                 190 ctc agt gag gtc gag tgg ttc tgc ccc ccg ctg ccc tgg agg aac cag     624
Leu Ser Glu Val Glu Trp Phe Cys Pro Pro Leu Pro Trp Arg Asn Gln
        195                 200                 205 acg gct gcc cag agg gca ccc aag ccc ctc ccc aaa gtc cag gca gtt     672
```

```
                Thr Ala Ala Gln Arg Ala Pro Lys Pro Leu Pro Lys Val Gln Ala Val
                    210                 215                 220 tgc cga agc aac ctg tcc cac ctt ctg gac ctg atg ggc agc ggg aag            720
Phe Arg Ser Asn Leu Ser His Leu Leu Asp Leu Met Gly Ser Gly Lys
225                 230                 235                 240 gag tcc ctg atc ttc atg aag aag cgg acc aag agg ctc aca gcc cag            768
Glu Ser Leu Ile Phe Met Lys Lys Arg Thr Lys Arg Leu Thr Ala Gln
                245                 250                 255 tgg gcg ctg gct gcc cag cgc ctg gca cag aag ctg ggg gcc acc cag            816
Trp Ala Leu Ala Ala Gln Arg Leu Ala Gln Lys Leu Gly Ala Thr Gln
            260                 265                 270 agg gac cag aag cag atc ctg gtc cac atc ggc ttc ctg acg gag gag            864
Arg Asp Gln Lys Gln Ile Leu Val His Ile Gly Phe Leu Thr Glu Glu
        275                 280                 285 tcc ggg gac gtg ttc agc cct cgg gtc ctg aag ggc ggg ccc cta ggg            912
Ser Gly Asp Val Phe Ser Pro Arg Val Leu Lys Gly Gly Pro Leu Gly
    290                 295                 300 gag atg gtg cag tgg gcg gac att ctg act gca ctc tat gtc ctg ggc            960
Glu Met Val Gln Trp Ala Asp Ile Leu Thr Ala Leu Tyr Val Leu Gly
305                 310                 315                 320 cat ggc ctg cgg gtc aca gtc tcc ctg aag gag ctg cag agt aac tta           1008
His Gly Leu Arg Val Thr Val Ser Leu Lys Glu Leu Gln Ser Asn Leu
                325                 330                 335 ggg gta ccg cca ggc cgg gga agc tgc ccg ctc acc atg ccc ctg ccc           1056
Gly Val Pro Pro Gly Arg Gly Ser Cys Pro Leu Thr Met Pro Leu Pro
            340                 345                 350 ttc gac ctc atc tac acc gac tac cac ggc ctg cag cag atg aag cgg           1104
Phe Asp Leu Ile Tyr Thr Asp Tyr His Gly Leu Gln Gln Met Lys Arg
        355                 360                 365 cac atg gga ctc tcc ttc aag aag tac cgg tgc cga atc agg gtc atc           1152
His Met Gly Leu Ser Phe Lys Lys Tyr Arg Cys Arg Ile Arg Val Ile
    370                 375                 380 gac acc ttt ggg acg gaa cct gcg tac aac cac gag gag tac gcc acg           1200
Asp Thr Phe Gly Thr Glu Pro Ala Tyr Asn His Glu Glu Tyr Ala Thr
385                 390                 395                 400 ctg cac ggc tac cgg acc aac tgg ggc tac tgg aac ctc aac ccc aag           1248
Leu His Gly Tyr Arg Thr Asn Trp Gly Tyr Trp Asn Leu Asn Pro Lys
                405                 410                 415 cag ttc atg acc atg ttt cct cat acc ccc gac aac tcc ttc atg ggc           1296
Gln Phe Met Thr Met Phe Pro His Thr Pro Asp Asn Ser Phe Met Gly
            420                 425                 430 ttt gtg tcc gag gag ctc aac gag acg gag aag cgg ctc atc aaa ggc           1344
Phe Val Ser Glu Glu Leu Asn Glu Thr Glu Lys Arg Leu Ile Lys Gly
        435                 440                 445 ggc aag gcc agc aac atg gcc gtg gtg tac ggc aag gag gcg agc atc           1392
Gly Lys Ala Ser Asn Met Ala Val Val Tyr Gly Lys Glu Ala Ser Ile
    450                 455                 460 tgg aag ctc cag ggg aag gag aag ttc ctg ggc atc ctg aac aaa tac           1440
Trp Lys Leu Gln Gly Lys Glu Lys Phe Leu Gly Ile Leu Asn Lys Tyr
465                 470                 475                 480 atg gag atc cat ggc acc gtg tac tac gag agc cag cgg ccc ccc gag           1488
Met Glu Ile His Gly Thr Val Tyr Tyr Glu Ser Gln Arg Pro Pro Glu
                485                 490                 495 gtg cca gcc ttt gtg aag aac cac ggc ctc tta ccg cag cct gag ttt           1536
Val Pro Ala Phe Val Lys Asn His Gly Leu Leu Pro Gln Pro Glu Phe
            500                 505                 510 cag cag ctg ctg cgc aag gcc aaa ctc ttc atc ggg ttt ggc ttc ccc           1584
Gln Gln Leu Leu Arg Lys Ala Lys Leu Phe Ile Gly Phe Gly Phe Pro
        515                 520                 525
```

| | | | | | | | | | | | | | | |
|---|---|---|---|---|---|---|---|---|---|---|---|---|---|---|
| tac | gag | ggc | ccc | gcc | ccc | ctg | gag | gcc | atc | gcc | aat | ggt | tgc | atc | ttc | 1632 |
| Tyr | Glu | Gly | Pro | Ala | Pro | Leu | Glu | Ala | Ile | Ala | Asn | Gly | Cys | Ile | Phe | |
| | 530 | | | | 535 | | | | 540 | | | | | | |

```
tac gag ggc ccc gcc ccc ctg gag gcc atc gcc aat ggt tgc atc ttc    1632
Tyr Glu Gly Pro Ala Pro Leu Glu Ala Ile Ala Asn Gly Cys Ile Phe
    530             535                 540 ctg cag tcc cgc ttc agc cca ccc cac agc tcc ctc aac cac gag ttc    1680
Leu Gln Ser Arg Phe Ser Pro Pro His Ser Ser Leu Asn His Glu Phe
545             550                 555                 560 ttc cga ggc aag ccc acc tcc aga gag gtg ttc tcc cag cat ccc tac    1728
Phe Arg Gly Lys Pro Thr Ser Arg Glu Val Phe Ser Gln His Pro Tyr
                565                 570                 575 gcg gag aac ttc atc ggc aag ccc cac gtg tgg aca gtc gac tac aac    1776
Ala Glu Asn Phe Ile Gly Lys Pro His Val Trp Thr Val Asp Tyr Asn
            580                 585                 590 aac tca gag gag ttt gaa gca gcc atc aag gcc att atg aga act cag    1824
Asn Ser Glu Glu Phe Glu Ala Ala Ile Lys Ala Ile Met Arg Thr Gln
        595                 600                 605 gta gac ccc tac cta ccc tat gag tac acc tgc gag ggg atg ctg gag    1872
Val Asp Pro Tyr Leu Pro Tyr Glu Tyr Thr Cys Glu Gly Met Leu Glu
    610                 615                 620 cgg atc cac gcc tac atc cag cac cag gac ttc tgc aga gct cca gac    1920
Arg Ile His Ala Tyr Ile Gln His Gln Asp Phe Cys Arg Ala Pro Asp
625                 630                 635                 640 cct gcc cta cca gag gcc cac gcc ccg cag agc ccc ttt gtc ctg gcc    1968
Pro Ala Leu Pro Glu Ala His Ala Pro Gln Ser Pro Phe Val Leu Ala
                645                 650                 655 ccc aat gcc acc cac ctc gag tgg gct cgg aac acc agc ttg gct cct    2016
Pro Asn Ala Thr His Leu Glu Trp Ala Arg Asn Thr Ser Leu Ala Pro
            660                 665                 670 ggg gcc tgg ccc ccc gcg cac gcc ctg cgg gcc tgg ctg gcc gtg cct    2064
Gly Ala Trp Pro Pro Ala His Ala Leu Arg Ala Trp Leu Ala Val Pro
        675                 680                 685 ggg agg gcc tgc acc gac acc tgc ctg gac cac ggg cta atc tgt gag    2112
Gly Arg Ala Cys Thr Asp Thr Cys Leu Asp His Gly Leu Ile Cys Glu
    690                 695                 700 ccc tcc ttc ttc ccc ttc ctg aac agc cag gac gcc ttc ctc aag ctg    2160
Pro Ser Phe Phe Pro Phe Leu Asn Ser Gln Asp Ala Phe Leu Lys Leu
705                 710                 715                 720 cag gtg ccc tgt gac agc acc gag tcg gag atg aac cac ctg tac ccg    2208
Gln Val Pro Cys Asp Ser Thr Glu Ser Glu Met Asn His Leu Tyr Pro
                725                 730                 735 gcg ttc gcc cag cct ggc cag gag tgc tac ctg cag aag gag cct ctg    2256
Ala Phe Ala Gln Pro Gly Gln Glu Cys Tyr Leu Gln Lys Glu Pro Leu
            740                 745                 750 ctc ttc agc tgc gcc ggc tcc aac acc aag tac cgc cgg ctc tgc ccc    2304
Leu Phe Ser Cys Ala Gly Ser Asn Thr Lys Tyr Arg Arg Leu Cys Pro
        755                 760                 765 tgc cgc gac ttc cgc aag ggc cag gtg gcc ttg tgc cag ggc tgt ctg    2352
Cys Arg Asp Phe Arg Lys Gly Gln Val Ala Leu Cys Gln Gly Cys Leu
    770                 775                 780 tga                                                                 2355

<210> SEQ ID NO 10
<211> LENGTH: 784
<212> TYPE: PRT
<213> ORGANISM: Homo sapiens

<400> SEQUENCE: 10

Met Ala Leu Pro Ala Leu Leu Thr Arg Leu Leu Pro Leu Arg Arg Leu
1               5                   10                  15

Phe Val Leu Gly Ile Gly Phe Phe Thr Leu Cys Phe Leu Met Thr Ser
            20                  25                  30
```

```
Leu Gly Gly Gln Phe Ser Ala Arg Arg Leu Gly Asp Ser Pro Phe Thr
        35                  40                  45

Ile Arg Thr Glu Val Met Gly Gly Pro Glu Ser Arg Gly Val Leu Arg
 50                  55                  60

Lys Met Ser Asp Leu Leu Glu Leu Met Val Lys Arg Met Asp Ala Leu
 65                  70                  75                  80

Ala Arg Leu Glu Asn Ser Ser Glu Leu His Arg Ala Gly Gly Asp Leu
                85                  90                  95

His Phe Pro Ala Asp Arg Met Pro Pro Gly Ala Gly Leu Met Glu Arg
            100                 105                 110

Ile Gln Ala Ile Ala Gln Asn Val Ser Asp Ile Ala Val Lys Val Asp
            115                 120                 125

Gln Ile Leu Arg His Ser Leu Leu His Ser Lys Val Ser Glu Gly
130                 135                 140

Arg Arg Asp Gln Cys Glu Ala Pro Ser Asp Pro Lys Phe Pro Asp Cys
145                 150                 155                 160

Ser Gly Lys Val Glu Trp Met Arg Ala Arg Trp Thr Ser Asp Pro Cys
                165                 170                 175

Tyr Ala Phe Phe Gly Val Asp Gly Thr Glu Cys Ser Phe Leu Ile Tyr
                180                 185                 190

Leu Ser Glu Val Glu Trp Phe Cys Pro Pro Leu Pro Trp Arg Asn Gln
            195                 200                 205

Thr Ala Ala Gln Arg Ala Pro Lys Pro Leu Pro Lys Val Gln Ala Val
            210                 215                 220

Phe Arg Ser Asn Leu Ser His Leu Leu Asp Leu Met Gly Ser Gly Lys
225                 230                 235                 240

Glu Ser Leu Ile Phe Met Lys Lys Arg Thr Lys Arg Leu Thr Ala Gln
                245                 250                 255

Trp Ala Leu Ala Ala Gln Arg Leu Ala Gln Lys Leu Gly Ala Thr Gln
            260                 265                 270

Arg Asp Gln Lys Gln Ile Leu Val His Ile Gly Phe Leu Thr Glu Glu
            275                 280                 285

Ser Gly Asp Val Phe Ser Pro Arg Val Leu Lys Gly Gly Pro Leu Gly
290                 295                 300

Glu Met Val Gln Trp Ala Asp Ile Leu Thr Ala Leu Tyr Val Leu Gly
305                 310                 315                 320

His Gly Leu Arg Val Thr Val Ser Leu Lys Glu Leu Gln Ser Asn Leu
                325                 330                 335

Gly Val Pro Pro Gly Arg Gly Ser Cys Pro Leu Thr Met Pro Leu Pro
            340                 345                 350

Phe Asp Leu Ile Tyr Thr Asp Tyr His Gly Leu Gln Gln Met Lys Arg
            355                 360                 365

His Met Gly Leu Ser Phe Lys Lys Tyr Arg Cys Arg Ile Arg Val Ile
            370                 375                 380

Asp Thr Phe Gly Thr Glu Pro Ala Tyr Asn His Glu Glu Tyr Ala Thr
385                 390                 395                 400

Leu His Gly Tyr Arg Thr Asn Trp Gly Tyr Trp Asn Leu Asn Pro Lys
                405                 410                 415

Gln Phe Met Thr Met Phe Pro His Thr Pro Asp Asn Ser Phe Met Gly
            420                 425                 430

Phe Val Ser Glu Glu Leu Asn Glu Thr Glu Lys Arg Leu Ile Lys Gly
            435                 440                 445
```

```
Gly Lys Ala Ser Asn Met Ala Val Val Tyr Gly Lys Glu Ala Ser Ile
    450                 455                 460

Trp Lys Leu Gln Gly Lys Glu Lys Phe Leu Gly Ile Leu Asn Lys Tyr
465                 470                 475                 480

Met Glu Ile His Gly Thr Val Tyr Tyr Glu Ser Gln Arg Pro Pro Glu
                485                 490                 495

Val Pro Ala Phe Val Lys Asn His Gly Leu Leu Pro Gln Pro Glu Phe
                500                 505                 510

Gln Gln Leu Leu Arg Lys Ala Lys Leu Phe Ile Gly Phe Gly Phe Pro
            515                 520                 525

Tyr Glu Gly Pro Ala Pro Leu Glu Ala Ile Ala Asn Gly Cys Ile Phe
    530                 535                 540

Leu Gln Ser Arg Phe Ser Pro Pro His Ser Ser Leu Asn His Glu Phe
545                 550                 555                 560

Phe Arg Gly Lys Pro Thr Ser Arg Glu Val Phe Ser Gln His Pro Tyr
                565                 570                 575

Ala Glu Asn Phe Ile Gly Lys Pro His Val Trp Thr Val Asp Tyr Asn
                580                 585                 590

Asn Ser Glu Glu Phe Glu Ala Ala Ile Lys Ala Ile Met Arg Thr Gln
            595                 600                 605

Val Asp Pro Tyr Leu Pro Tyr Glu Tyr Thr Cys Glu Gly Met Leu Glu
    610                 615                 620

Arg Ile His Ala Tyr Ile Gln His Gln Asp Phe Cys Arg Ala Pro Asp
625                 630                 635                 640

Pro Ala Leu Pro Glu Ala His Ala Pro Gln Ser Pro Phe Val Leu Ala
                645                 650                 655

Pro Asn Ala Thr His Leu Glu Trp Ala Arg Asn Thr Ser Leu Ala Pro
                660                 665                 670

Gly Ala Trp Pro Pro Ala His Ala Leu Arg Ala Trp Leu Ala Val Pro
            675                 680                 685

Gly Arg Ala Cys Thr Asp Thr Cys Leu Asp His Gly Leu Ile Cys Glu
    690                 695                 700

Pro Ser Phe Phe Pro Phe Leu Asn Ser Gln Asp Ala Phe Leu Lys Leu
705                 710                 715                 720

Gln Val Pro Cys Asp Ser Thr Glu Ser Glu Met Asn His Leu Tyr Pro
                725                 730                 735

Ala Phe Ala Gln Pro Gly Gln Glu Cys Tyr Leu Gln Lys Glu Pro Leu
                740                 745                 750

Leu Phe Ser Cys Ala Gly Ser Asn Thr Lys Tyr Arg Arg Leu Cys Pro
            755                 760                 765

Cys Arg Asp Phe Arg Lys Gly Gln Val Ala Leu Cys Gln Gly Cys Leu
    770                 775                 780

<210> SEQ ID NO 11
<211> LENGTH: 2476
<212> TYPE: DNA
<213> ORGANISM: Homo sapiens

<400> SEQUENCE: 11
ctgctcgcac caacaagttt gaacaatgat caccgtcaac cccgatggga agataatggt      60
cagaagatgc ctggtcaccc tgagacccttt tcggcttttt gtcctgggca tcggcttctt     120
cactctctgc ttcctgatga cgtctctggg aggccagttc tcggcccggc gcctggggga     180
ctcgccattc accatccgca cagaagtgat gggggggccc gagtcccgcg gcgtcctgcg     240
```

```
caagatgagc gacctgctgg agctgatggt gaagcgcatg gacgcactgg ccaggctgga      300
gaacagcagt gagctgcacc gggccggcgg cgacctgcac tttcccgcag acaggatgcc      360
ccctggggcc ggcctcatgg agcggatcca ggctattgcc cagaacgtct ccgacatcgc      420
tgtgaaggtg gaccagatcc tgcgccacag tctgctcctg cacagcaagg tgtcagaagg      480
ccggcgggac cagtgtgagg cacccagtga ccccaagttc cctgactgct cagggaaggt      540
ggagtggatg cgtgcccgct ggacctctga cccctgctac gccttctttg gggtggacgg      600
caccgagtgc tccttcctca tctacctcag tgaggtcgag tggttctgcc cccgctgcc       660
ctggaggaac cagacggctg cccagagggc acccaagccc ctccccaaag tccaggcagt      720
tttccgaagc aacctgtccc accttctgga cctgatgggc agcgggaagg agtccctgat      780
cttcatgaag aagcggacca agaggctcac agcccagtgg gcgctggctg cccagcgcct      840
ggcacagaag ctgggggcca cccagaggga ccagaagcag atcctggtcc acatcggctt      900
cctgacggag gagtccgggg acgtgttcag ccctcgggtc ctgaagggcg ggcccctagg      960
ggagatggtg cagtgggcgg acattctgac tgcactctat gtcctgggcc atggcctgcg     1020
ggtcacagtc tccctgaagg agctgcagag taacttaggg gtaccgccag gccggggaag     1080
ctgcccgctc accatgcccc tgcccttcga cctcatctac accgactacc acggcctgca     1140
gcagatgaag cggcacatgg gactctcctt caagaagtac cggtgccgaa tcagggtcat     1200
cgacaccttc gggacggaac ctgcgtacaa ccacgaggag tacgccacgc tgcacggcta     1260
ccggaccaac tggggctact ggaacctcaa ccccaagcag ttcatgacca tgtttcctca     1320
taccccgac aactccttca tgggcttcgt gtccgaggag ctcaacgaga cggagaagcg     1380
gctcatcaaa gcggcaagg ccagcaacat ggccgtggtg tacggcaagg aggcgagcat     1440
ctggaagctc caggggaagg agaagttcct gggcatcctg aacaaataca tggagatcca     1500
tggcaccgtg tactacgaga gccagcggcc ccccgaggtg ccagcctttg tgaagaacca     1560
cggcctctta ccgcagcctg agtttcagca gctgctgcgc aaggccaaac tcttcatcgg     1620
gtttggcttc ccctacgagg gccccgcccc cctggaggcc atcgccaatg gttgcatctt     1680
cctgcagtcc cgcttcagcc cgccccacag ctccctcaac cacgagttct ccgaggcaa     1740
gcccacctcc agagaggtgt tctcccagca tccctacgcg gagaacttca tcggcaagcc     1800
ccacgtgtgg acagtcgact acaacaactc agaggagttt gaagcagcca tcaaggccat     1860
tatgagaact caggtagacc cctacctacc ctatgagtac acctgcgagg ggatgctgga     1920
gcggatccac gcctacatcc agcaccagga cttctgcaga gctccagacc ctgccctacc     1980
agaggcccac gccccgcaga gccccttgtt cctggccccc aatgccaccc acctcgagtg     2040
ggctcggaac accagcttgg ctcctgggc ctggcccccc gcgcacgccc tgcgggcctg     2100
gctggccgtg cctgggaggg cctgcaccga cacctgcctg gaccacgggc taatctgtga     2160
gccctccttc ttccccttcc tgaacagcca ggacgccttc tcaagctgc aggtgccctg     2220
tgacagcacc gagtcggaga tgaaccacct gtacccggcg ttcgcccagc tggccagga     2280
gtgctacctg cagaaggagc ctctgctctt cagctgcgcc ggctccaaca ccaagtaccg     2340
ccggctctgc ccctgccgcg acttccgcaa gggccaggtg gccttgtgcc agggctgtct     2400
gtgaatccgc ctctgccgcc ctgcctggca cccacgctgg ctctctcctg ccgcgggaga     2460
aagcaccagc aggttc                                                     2476
```

<210> SEQ ID NO 12
<211> LENGTH: 792

-continued

```
<212> TYPE: PRT
<213> ORGANISM: Homo sapiens

<400> SEQUENCE: 12

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
            20                  25                  30

Thr Leu Cys Phe Leu Met Thr Ser Leu Gly Gly Gln Phe Ser Ala Arg
        35                  40                  45

Arg Leu Gly Asp Ser Pro Phe Thr Ile Arg Thr Glu Val Met Gly Gly
    50                  55                  60

Pro Glu Ser Arg Gly Val Leu Arg Lys Met Ser Asp Leu Leu Glu Leu
65                  70                  75                  80

Met Val Lys Arg Met Asp Ala Leu Ala Arg Leu Glu Asn Ser Ser Glu
                85                  90                  95

Leu His Arg Ala Gly Gly Asp Leu His Phe Pro Ala Asp Arg Met Pro
            100                 105                 110

Pro Gly Ala Gly Leu Met Glu Arg Ile Gln Ala Ile Ala Gln Asn Val
        115                 120                 125

Ser Asp Ile Ala Val Lys Val Asp Gln Ile Leu Arg His Ser Leu Leu
130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Glu Trp Met Arg
                165                 170                 175

Ala Arg Trp Thr Ser Asp Pro Cys Tyr Ala Phe Phe Gly Val Asp Gly
            180                 185                 190

Thr Glu Cys Ser Phe Leu Ile Tyr Leu Ser Glu Val Glu Trp Phe Cys
        195                 200                 205

Pro Pro Leu Pro Trp Arg Asn Gln Thr Ala Ala Gln Arg Ala Pro Lys
    210                 215                 220

Pro Leu Pro Lys Val Gln Ala Val Phe Arg Ser Asn Leu Ser His Leu
225                 230                 235                 240

Leu Asp Leu Met Gly Ser Gly Lys Glu Ser Leu Ile Phe Met Lys Lys
                245                 250                 255

Arg Thr Lys Arg Leu Thr Ala Gln Trp Ala Leu Ala Ala Gln Arg Leu
            260                 265                 270

Ala Gln Lys Leu Gly Ala Thr Gln Arg Asp Gln Lys Gln Ile Leu Val
        275                 280                 285

His Ile Gly Phe Leu Thr Glu Glu Ser Gly Asp Val Phe Ser Pro Arg
    290                 295                 300

Val Leu Lys Gly Gly Pro Leu Gly Glu Met Val Gln Trp Ala Asp Ile
305                 310                 315                 320

Leu Thr Ala Leu Tyr Val Leu Gly His Gly Leu Arg Val Thr Val Ser
                325                 330                 335

Leu Lys Glu Leu Gln Ser Asn Leu Gly Val Pro Pro Gly Arg Gly Ser
            340                 345                 350

Cys Pro Leu Thr Met Pro Leu Pro Phe Asp Leu Ile Tyr Thr Asp Tyr
        355                 360                 365

His Gly Leu Gln Gln Met Lys Arg His Met Gly Leu Ser Phe Lys Lys
    370                 375                 380

Tyr Arg Cys Arg Ile Arg Val Ile Asp Thr Phe Gly Thr Glu Pro Ala
385                 390                 395                 400
```

-continued

```
Tyr Asn His Glu Glu Tyr Ala Thr Leu His Gly Tyr Arg Thr Asn Trp
            405                 410                 415

Gly Tyr Trp Asn Leu Asn Pro Lys Gln Phe Met Thr Met Phe Pro His
        420                 425                 430

Thr Pro Asp Asn Ser Phe Met Gly Phe Val Ser Glu Glu Leu Asn Glu
            435                 440                 445

Thr Glu Lys Arg Leu Ile Lys Gly Gly Lys Ala Ser Asn Met Ala Val
450                 455                 460

Val Tyr Gly Lys Glu Ala Ser Ile Trp Lys Leu Gln Gly Lys Glu Lys
465                 470                 475                 480

Phe Leu Gly Ile Leu Asn Lys Tyr Met Glu Ile His Gly Thr Val Tyr
                485                 490                 495

Tyr Glu Ser Gln Arg Pro Pro Glu Val Pro Ala Phe Val Lys Asn His
            500                 505                 510

Gly Leu Leu Pro Gln Pro Glu Phe Gln Gln Leu Leu Arg Lys Ala Lys
            515                 520                 525

Leu Phe Ile Gly Phe Gly Phe Pro Tyr Glu Gly Pro Ala Pro Leu Glu
    530                 535                 540

Ala Ile Ala Asn Gly Cys Ile Phe Leu Gln Ser Arg Phe Ser Pro Pro
545                 550                 555                 560

His Ser Ser Leu Asn His Glu Phe Phe Arg Gly Lys Pro Thr Ser Arg
                565                 570                 575

Glu Val Phe Ser Gln His Pro Tyr Ala Glu Asn Phe Ile Gly Lys Pro
            580                 585                 590

His Val Trp Thr Val Asp Tyr Asn Asn Ser Glu Glu Phe Glu Ala Ala
        595                 600                 605

Ile Lys Ala Ile Met Arg Thr Gln Val Asp Pro Tyr Leu Pro Tyr Glu
    610                 615                 620

Tyr Thr Cys Glu Gly Met Leu Glu Arg Ile His Ala Tyr Ile Gln His
625                 630                 635                 640

Gln Asp Phe Cys Arg Ala Pro Asp Pro Ala Leu Pro Glu Ala His Ala
                645                 650                 655

Pro Gln Ser Pro Phe Val Leu Ala Pro Asn Ala Thr His Leu Glu Trp
            660                 665                 670

Ala Arg Asn Thr Ser Leu Ala Pro Gly Ala Trp Pro Pro Ala His Ala
        675                 680                 685

Leu Arg Ala Trp Leu Ala Val Pro Gly Arg Ala Cys Thr Asp Thr Cys
    690                 695                 700

Leu Asp His Gly Leu Ile Cys Glu Pro Ser Phe Phe Pro Phe Leu Asn
705                 710                 715                 720

Ser Gln Asp Ala Phe Lys Leu Gln Val Pro Cys Asp Ser Thr Glu
                725                 730                 735

Ser Glu Met Asn His Leu Tyr Pro Ala Phe Ala Gln Pro Gly Gln Glu
            740                 745                 750

Cys Tyr Leu Gln Lys Glu Pro Leu Leu Phe Ser Cys Ala Gly Ser Asn
        755                 760                 765

Thr Lys Tyr Arg Arg Leu Cys Pro Cys Arg Asp Phe Arg Lys Gly Gln
    770                 775                 780

Val Ala Leu Cys Gln Gly Cys Leu
785                 790
```

US 7,348,171 B2

N-ACETYLGLUCOSAMINYLTRANSFERASE VB CODING SEQUENCES, RECOMBINANT CELLS AND METHODS

CROSS REFERENCE TO RELATED APPLICATIONS

This application is a Continuation-in-Part of International Patent Application PCT/US03/12759, filed Apr. 23, 2003, which application claims benefit of U.S. Provisional Patent Application No. 60/375,172, filed Apr. 23, 2002.

ACKNOWLEDGMENT OF FEDERAL RESEARCH SUPPORT

This invention was made, at least in part, with funding from the National Cancer Institute (Grant No. 2 R01 CA64462-05A2). Accordingly, the United States Government has certain rights in this invention.

BACKGROUND OF THE INVENTION

The field of this invention is the area of protein glycosylation, specifically the area of the particular enzyme, UDP N-acetylglucosaminyltransferase V, involved in the expression of the β(1,6) branch structure found in tri- and tetraantennary NBlinked oligosaccharides. The field relates to the amino acid sequences of rat, human and hamster GlcNAc T-V proteins, genes encoding active enzyme and cell lines genetically engineered to express a nucleotide sequence encoding active enzyme.

UDP-N-acetylglucosamine:α-6-D-mannoside β-1,6-N-acetylglucosaminyltransferase V (EC 2.4.1.155) is the Golgi enzyme responsible for the synthesis of the β(1,6) branch structure of tri- and tetraantennary β-linked oligosaccharides. For brevity, this enzyme is abbreviated GlcNAc T-V herein. GlcNAc T-V activity has been found in many tissues and cell types. One GlcNAc T-V protein, termed GlcNAc T-Va herein, has been purified (Shoreibah et al. (1992) J. Biol. Chem. 262: 2920-2927, and the cDNA has been isolated and sequenced (Shoreibah et al. (1993) J. Biol. Chem. 268:15381-15385, U.S. Pat. Nos. 5,602,003 and 6,015,701). GlcNAc T-Va is determined by a gene on chromosome 2.

Altered glycosylation of membrane glycoproteins and glycolipids is observed in mammalian cells transformed with diverse tumor viruses, carcinogens, or transfection with certain oncogenes. In some cases, there is a quantitative increase in a particular substituent, e.g., sialylation. In other instances, there is the reappearance of an oligosaccharide structure in the tumor which is normally only found in fetal tissue; for instance, certain Lewis histo-blood group antigens have been detected in adenocarcinomas.

Qualitative differences in oligosaccharides may also be observed in certain transformed cells. BHK fibroblasts transformed with polyoma virus or with Rous sarcoma virus display more highly branched complex N-linked oligosaccharides than do the corresponding normal cells. The expression of the β-1,6 branch structure (-[GlcNAc-β(1,6)Man-α (1,6)Man]-) found in tri- and tetraantennary NBlinked oligosaccharides is increased in the transformed cells. This has been correlated with a 2 to 3-fold increase in the specific activity of GlcNAc T-V. Transformation of murine cells with polyoma viruses, adenovirus, tumorigenic DNA and either the ras or the her-2/new oncogenes also resulted in increased GlcNAc T-V activity. By contrast, several other glycosyl transferases involved in N-linked glycosylation are unchanged in the transformed cells. The mechanism for the increased specific activity of GlcNAc T-V in transformed cells is not known.

The increase in the β(1,6) branching of the cell surface-bound oligosaccharides has been associated, at least in some cases, with capacity for metastasis. Increased levels of β-1,6 branching over the level in normal tissue has been observed for some human breast tumor tissues.

Certain mammalian glycosyl transferases from the N-linked glycosylation pathway have been purified and characterized. The enzymatic machinery for the glycosylation of proteins in mammalian cells is generally located in the membranes of the Golgi apparatus. α(1,3) mannoside β(1,2) UDP-N-acetylglucosaminyl transferase I (GlcNAc T-I) (EC 2.4.1 101) and UDP-N-acetyl glucosaminyl transferase II (GlcNAc T-II) (EC 2.4.1.143) have been purified from rabbit liver and rat liver, respectively. GlcNAc T-I has been purified 7000-fold from a Triton X-100 extract of rabbit liver acetone powder by two rounds of affinity chromatography over UDP-hexanolamine agarose, in the first round by elution with NaCl, and in the second round by elution with UDP (Oppenheimer and Hill (1981) J. Biol. Chem. 256: 799-804). GlcNAc T-II (UDP-N-acetylglucosaminyl:α-D-mannoside β(1,2) Bacetylglucosaminyl-transferase II) was purified 60,000-fold from rat liver by Triton X-100 extraction of rat liver membranes, followed by chromatography over carboxymethyl-cellulose, hydroxylapatite, and sequential elutions using NaCl, UDP-GlcNAc and EDTA from 5-mercuri-UDP-GlcNAc-thiopropyl-SEPHAROSE, Affi-Gel (Bio-Rad Laboratories, Richmond, Calif.) blue affinity chromatography and finally UDP-GlcNAc-SEPHAROSE (Bendiak and Schachter (1987) J. Biol. Chem. 262: 5775-5783).

The cDNA encoding a rat liver Golgi sialyl transferase (β-galactoside α(2,6)-sialyl transferase (EC 2.4.99.1) has been cloned and sequenced (Weinstein et al. (1987) J. Biol. Chem. 262: 17735-17743). The corresponding enzyme has been purified 23,000-fold from Triton CF-54 extracts of rat liver membranes by three rounds of affinity chromatography over CDP-hexanolamine-agarose (Weinstein et al. (1982) J. Biol. Chem. 257: 13835-13844). Soluble recombinant glycosyl transferases are described in U.S. Pat. No. 5,032,519, issued Jul. 16, 1991, incorporated by reference herein.

There is a need in the art for enzymes which function in the glycosylation of proteins or in the remodeling of the glycosylation of proteins, especially to improve the glycosylation status of recombinant proteins.

SUMMARY OF THE INVENTION

An object of this invention are nucleotide sequences encoding a previously unknown N-acetylglucosaminyltransferase V enzyme, called Vb herein. The GlcNAc T-Vb of the present invention is useful in in vitro enzymatic reactions of this enzyme and in recombinant host cells for the production of glycoproteins with more efficient and extensive glycosylation. As specifically exemplified herein, four amino acid sequences of human GlcNAc T-Vb are given in Tables 2, 4, 5 and 8 (and SEQ ID NOs:2, 8, 10 and 12), and all synonymous coding sequences are within the scope of the present invention. The specifically exemplified human coding sequences for GlcNAc T-Vb are given in Tables 1, 4 and 5 and 7; see also SEQ ID NOs:1, 7, 9 and 11. The DNA sequence for an alternatively spliced sequence is given in Tables 4 and 7 and in SEQ ID NO:7 and SEQ ID NO: 11.

Additional aspects of the present invention are genetically engineered, soluble GlcNAc T-Vb enzymatically active proteins, including amino acids 33-782 of the human sequence provided in Table 2 (and in SEQ ID NO:2), for example. Also within the present invention are nucleic acid molecules genetically engineered to produce soluble and entire GlcNAc T-Vb proteins in culture media.

Also embodied in the invention are genomic and cDNA sequences encoding GlcNAc T-Vb, and recombinant host cells genetically engineered to express sequences encoding active GlcNAc T-Vb enzymes. Cultured cells suitable for recombinant expression of GlcNAc T-Vb include mouse fibroblast cells (e.g., 3T3 cells) and human embryonic kidney cells (e.g., HEK-293 cells) and insect cells (Sf9 cells, for example). Vectors useful for recombinant GlcNAc T-Vb expression include pCDNA3.1, pEAK (Edge Biosys, Gaithersburg, Md.) and baculovirus vectors (e.g., commercially available from Stratagene, La Jolla, Calif.) for mouse, human and insect cells, respectively. Aspergillus expression systems can also be used to express GlcNAc T-Vb in Golgi-bound or soluble form.

Also provided by this invention are polyclonal and monoclonal antibodies specific for human GlcNAc T-Vb. These antibodies also bind to and are useful for detection and isolation of GlcNAc T-Vb from mammalian and other sources.

Also provided in this invention is GlcNAc T-Vb produced by recombinant DNA technology in prokaryotic or eukaryotic host cells. Disclosed in this invention are the complete amino acid sequences for human and mouse. Examples of methods of producing recombinant active GlcNAc T-Vb by recombinant DNA technology are disclosed. The exemplified amino acid sequences and the nucleotide sequences encoding GlcNAc T-Vb, and subsequences within, as understood in the art, are useful for isolating GlcNAc T-Vb coding sequences from a wide range of species and for producing useful quantities of GlcNAc T-Vb by recombinant DNA technology.

Further objects of this invention are cDNA clones encoding GlcNAc T-Vb and genomic clones encoding GlcNAc T-Vb. The antibodies raised against human GlcNAc T-Vb (or other GlcNAc T-Vb's or peptide-specific antibodies for GlcNAc T-Vb) can be used to detect expression of GlcNAc T-Vb from sources other than human by virtue of cross-reactivity with those other GlcNAc T-Vb enzymes; alternatively, these antibodies can be used to screen cDNA expression libraries. Similarly, the specifically exemplified human or mouse sequences can be used to screen genomic or cDNA libraries constructed using nucleic acids from sources other than those exemplified herein, or these can be used to prepare primers to amplify sequences encoding GlcNAc T-Vb from mRNA populations prepared from rat, hamster, avian or from other animal cells. The cDNA and/or genomic sequences encoding GlcNAc T-Vb are useful in directing the recombinant expression of GlcNAc T-Vb.

Further objects of this invention are nucleotide sequences encoding human GlcNAc T-Vb, and nucleotide sequences encoding GlcNAc T-Vb from other vertebrate, preferably mammalian, sources, including cDNA and genomic sequences. Nucleotide sequences encoding human GlcNac T-Vb are provided in Tables 1, 4, 5 and 7 and in SEQ ID NOs:1, 7, 8 and 9, and mouse coding and deduced amino acid sequences are provided in Table 3 and in SEQ ID NO:3 and 4.

The skilled artisan recognizes that there will be more than one nucleotide sequence capable of encoding the same amino acid sequence due to the degeneracy of the genetic code. Exemplary human GlcNAc T-Vb amino acid sequences are given in Tables 2, 4 and 5 and specifically exemplified coding sequences are given in Tables 2-5. See also SEQ ID NOs:1-4 and SEQ ID NOs:7-10 and 11. SEQ ID NOs:7 and 8 and SEQ ID NOs:11 and 12 represent alternatively spliced sequences and deduced amino acid sequences for human; see also Tables 4 and 7-8. The first alternatively spliced sequence lacks two codons in the region of the stem-catalytic domains, resulting in an active protein which is two amino acids shorter. Another variant, which is expressed in human brain cells, is given in Table 8. Mouse sequences are given in Table 3 and in SEQ ID NO:3 and 4. These sequences, and sequence variants thereof which encode functionally equivalent GlcNAc T-Vb, can all be used to express functional GlcNAc T-Vb in a desired recombinant host cell. The GlcNAc T-Vb coding sequences from other vertebrate species, preferably from mammals, will be highly homologous at the nucleotide and amino acid sequence levels to the exemplified mouse and human GlcNAc T-Vb coding and amino acid sequences disclosed herein. Functionally equivalent GlcNAc T-Vb coding sequences with at least 70%, preferably at least 80%, more preferably at least 85% or 90% nucleotide sequence identity to the exemplified human and/or mouse GlcNAc T-Vb coding sequences can be identified and isolated from cDNA libraries prepared from mRNA sources other than human and mouse cells, using well-known DNA-DNA hybridization technology and the exemplified GlcNAc T-Vb coding sequences provided herein. Also contemplated are genomic clones encoding GlcNAc T-Vb, which clones comprise the natural regulatory sequences. It is understood that any intron sequences in genomic GlcNAc T-Vb are not to be included in sequence comparisons to the exemplified full-length coding sequence, and gaps may be introduced to maximize identity. Each of the specifically exemplified GlcNAc T-Vb sequences provided herein has enzymatic activity using the assay described in Example 2.

Additional objects of this invention are DNA molecules containing a first nucleotide sequence encoding an enzymatically active GlcNAc T-Vb and a second nucleotide sequence not found associated with the GlcNAc T-Vb coding sequence in nature, termed an exogenous nucleotide sequence herein. Preferably the first nucleotide sequence encodes a polypeptide sequence with GlcNAc T-Vb activity, said polypeptide having an amino acid sequence as given in Tables 2, 3, 4, 5 or 8.

Still further objects of the invention are cells genetically engineered to contain a DNA molecule containing a first nucleotide sequence encoding an enzymatically active GlcNAc T-Vb and a second nucleotide sequence not found associated with the GlcNAc T-Vb coding sequence in nature. Mammalian cells are preferred for recombinant expression of GlcNAc T-Vb coding sequences. Particularly preferred are 3T3 mouse cells and human HEK-293 cells; COS-7 cells and CHO (Chinese Hamster Ovary) cells and insect cells can also be used. The exemplified human and mouse GlcNAc T-VB amino acid sequences are particularly preferred, preferably encoded by the exemplified nucleotide coding sequences as in Tables 2, 3, 4, 5 and 7 (and in SEQ ID NO:1, 3, 7, 9 and 11).

DETAILED DESCRIPTION OF THE INVENTION

Figure 1:
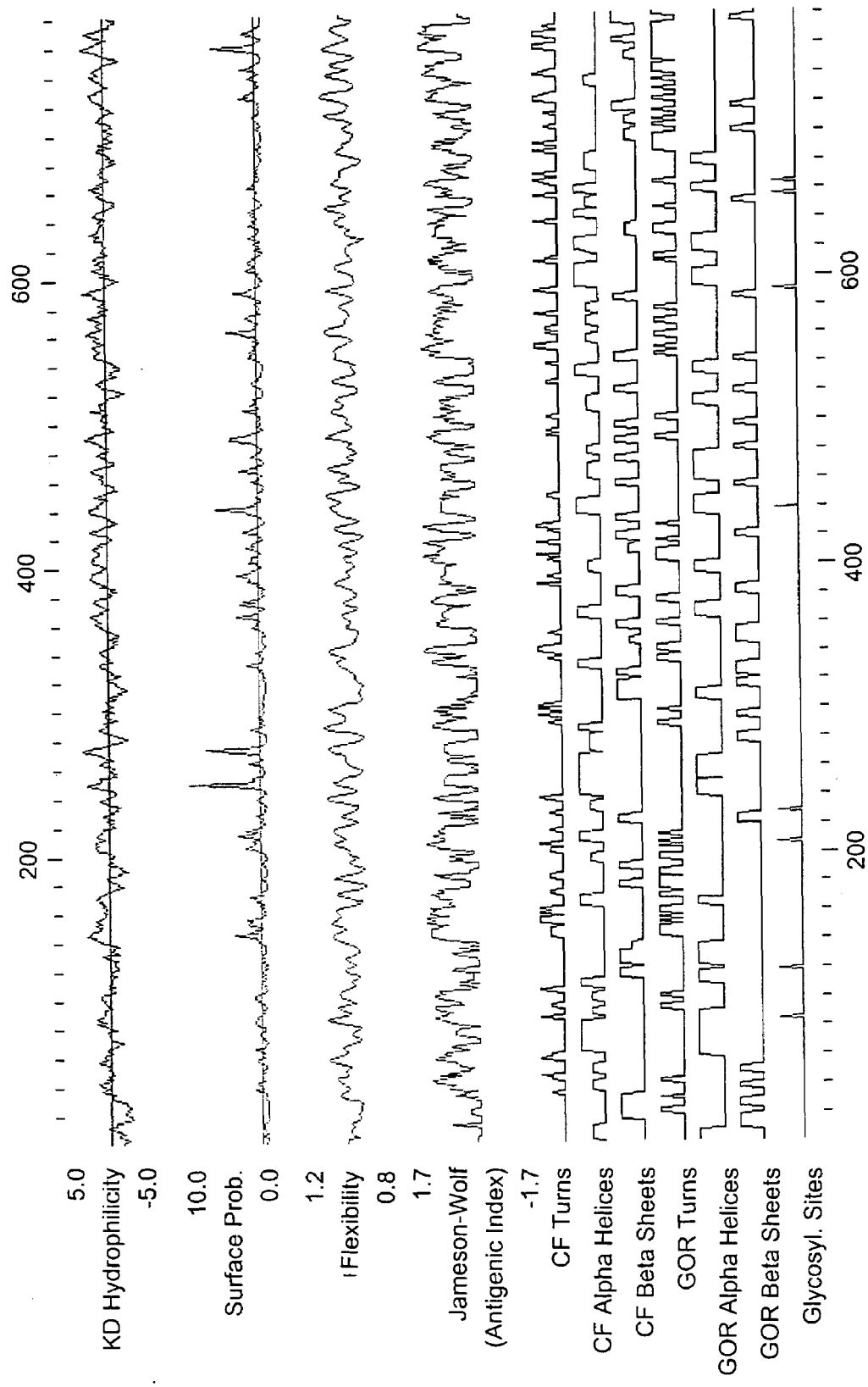
FIG. 1 summarizes the analysis of the primary structure of human GlcNAc T-Vb with respect to hydrophobicity (Kyte-Doolittle analysis), probability of particular residues being exposed at the surface of the protein, flexibility, antigenicity, CF (Chou-Fasman) turns, CF alpha-helical regions, CF beta sheet regions, GOR (Garnier-Osguthorpe-Robson) turns, GOR alpha helices, GOR beta sheets and glycosylation sites using the PLOTSTRUCTURE computer program (Wisconsin Sequence Analysis Package, accessed via the internet).

In general, the terminology used herein is standard, as understood by those of ordinary skill in the fields of molecular biology, biochemistry, protein chemistry, and cell biology. For added clarity, certain terms are defined herein. Standard abbreviations are used; these abbreviations are consistent with those used and approved by scientific journals in the field (e.g., Journal of Biological Chemistry, Science, Nature, etc.).

Methods used herein are either specifically referenced or are sufficiently well known as to be available in at least one of several readily accessible published collections of methodologies. See, e.g., Sambrook et al. (1989) *Molecular Cloning, A Laboratory Manual* (2nd ed.), Cold Spring Harbor Laboratory, Cold Spring Harbor, N.Y., Innis et al. (1990) *PCR Protocols: A Guide to Methods and Applications*, Academic Press, New York, N.Y., and references cited therein, all incorporated herein by reference.

Complementary DNA (cDNA) synthesis involves the in vitro synthesis of a double stranded DNA sequence by enzymatic reverse transcription of mRNA isolated from donor cells. Brain, skeletal muscle, testes and ovary are tissues in which there is relatively abundant expression of GlcNAc T-Vb. In the present invention, a human brain cDNA library (commercially available from OriGene Technologies, Inc., Rockville, Md.) is screened using primers specific to the GlcNAc T-Vb sequence, and amplification products were detected. Then the library was further screened to identify the largest and most 5' GlcNAc T-Vb cDNA inserts. Sequence databases were searched for related sequence using BLAST analysis, and the coding sequence for the human GlcNAc T-Vb was, in part, assembled from partial sequences (ESTs, expressed sequence tags) and in part, from empirical determination. The result is shown in Table 1, and the deduced amino acid sequence of the GlcNAc T-Vb protein is provided in Table 2. See also SEQ ID NO:1 and SEQ ID NO:2, respectively. Active GlcNAc T-Vb is encoded by a gene on chromosome 17. Without wishing to be bound by theory, analysis of the amino acid sequence indicates that the N-terminal 10 amino acids of this protein are cytoplasmic, there is a transmembrane domain extending from approximately amino acids 11-32, and the remainder of the protein encompasses a stem region and the catalytic region, which is most likely extending into the lumen of the Golgi apparatus.

The sequence encoding human GlcNAc T-Vb was used to search sequence databases to identify sequences encoding the mouse GlcNAc T-Vb enzyme. Numerous partial (EST) sequences were identified which are portions of the mouse GlcNAc T-Vb coding sequence. The complete mouse sequence is presented in Table 3 and in SEQ ID NO:3 See also SEQ ID NO:3 and SEQ ID NO:4 for nucleotide and amino acid sequences, respectively.

N-acetylglucosaminyl transferase Va (GlcNAc T-Va) is the enzyme described in Shoreibah et al. (1992) supra and in U.S. Pat. Nos. 5,602,003 and 6,015,701, incorporated by reference herein. It is encoded by a gene residing on human chromosome 2.

N-acetylglucosaminyl transferase Vb (GlcNAc T-Vb) is described herein. As specifically exemplified for the human enzyme, amino acid sequences are given in Tables 2, 4 and 5 and SEQ ID NOs:2, 8 and 10. Comparison of the GlcT-Va and GlcNAc T-Vb sequences revealed that there is only about 50% amino acid sequence identity and about 60% amino acid sequence similarity. Thus, the enzymes are distinct. They are further distinguished in terms of the relative abundances in various tissues, with GlcNAc T-Vb being especially abundant in brain whereas GlcNAc T-Va is more abundantly expressed in certain other tissues including kidney. GlcNAc T-Vb is encoded by a gene on chromosome 17.

Expression refers to the transcription and translation of a structural gene (coding sequence) so that a protein (i.e., expression product) having the biological activity of GlcNAc T-Vb is synthesized. It is understood that post-translational modification(s) may remove portions of the polypeptide which are not essential to enzymatic activity and that glycosylation processes may also occur.

The term expression control sequences refer to DNA sequences that control and regulate the transcription and translation of another DNA sequence (i.e., a coding sequence). A coding sequence is operatively linked to an expression control sequence when the expression control sequence controls and regulates the transcription and translation of that coding sequence. Expression control sequences include, but are not limited to, promoters, enhancers, promoter-associated regulatory sequences, transcription termination and polyadenylation sequences, and their positioning and use is well understood by the ordinary skilled artisan. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene. The combination of the expression control sequences and the GlcNAc T-Vb coding sequences form the GlcNAc T-Vb expression cassette.

As used herein, an exogenous or heterologous nucleotide sequence is one which is not in nature covalently linked to a particular nucleotide sequence, e.g., a GlcNAc T-Vb coding sequence. Examples of exogenous nucleotide sequences include, but are not limited to, plasmid vector sequences, expression control sequences not naturally associated with particular GlcNAc T-Vb coding sequences, and viral vector sequences. A non-naturally occurring DNA molecule is one which does not occur in nature, and it is thus distinguished from a chromosome, or example. As used herein, a non-naturally occurring DNA molecule comprising a sequence encoding an expression product with GlcNAc T-V activity is one which comprises said coding sequence and sequences which are not associated therewith in nature.

Similarly, as used herein an exogenous gene is one which does not naturally occur in a particular recombinant host cell but has been introduced in using genetic engineering techniques well known in the art. An exogenous gene as used herein can comprise a GlcNAc T-Vb coding sequence expressed under the control of an expression control sequence not associated in nature with said coding sequence.

Another feature of this invention is the expression of the sequences encoding GlcNAc T-Vb. As is well-known in the art, DNA sequences may be expressed by operatively linking them to an expression control sequence in an appropriate expression vector and employing that expression vector to transform an appropriate host cell.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *Escherichia coli* plasmids colE1, pCR1, pBR322, pMB9 and their derivatives, plasmids such as RP4; phage DNAs, e.g., M13 derivatives, the numerous derivatives of phage λ, e.g., λgt11, and other phage DNA; yeast plasmids derived from the 2μ circle; vectors useful in eukaryotic cells, such as insect or mammalian cells; vectors derived from combinations of plasmids and phage DNAs, such as plasmids that have been modified to employ phage DNA or other expression control sequences; baculovirus derivatives; and the like. For mammalian cells there are a number of well-known expression vectors available to the art.

Any of a wide variety of expression control sequences may be used in these vectors to express the DNA sequences of this invention. Such useful expression control sequences include, for example, the early and late promoters of SV40 or adenovirus for expression in mammalian cells, the lac system, the trp system, the tac or trc system, the major operator and promoter regions of phage λ, the control regions of fd coat protein, the promoter for 3-phosphoglycerate kinase of phosphatase (e.g., pho5), the promoters of the yeast α-mating factors, and other sequences known to control the expression of genes of prokaryotic or eukaryotic cells or their viruses, and various combinations thereof. The skilled artisan understands which expression control sequences are appropriate to particular vectors and host cells.

A wide variety of host cells are also useful in expressing the DNA sequences of this invention. These hosts may include well-known prokaryotic and eukaryotic hosts, such as strains of *E. coli, Pseudomonas, Bacillus, Streptomyces*, fungi such as yeasts, and animal cells, such as Chinese Hamster Ovary (CHO), R1.1, B-W and L-M cells, African Green Monkey kidney cells (e.g., COS 1, COS-7, BSC1, BSC40, and BMT10), insect cells (e.g., Sf9), and human cells and plant cells in culture.

It is understood that not all combinations of vector, expression control sequence and host cell will function equally well to express the DNA sequences of this invention. However, one skilled in the art will be able to select the proper vector, expression control sequence, and host cell combination without undue experimentation to accomplish the desired expression without departing from the scope of this invention.

In selecting a suitable expression control sequence, a variety of factors will normally be considered. These include, for example, the relative strength of the promoter, its controllability, and its compatibility with the particular DNA sequence or gene to be expressed, e.g., with regard to potential secondary structure. Suitable hosts will be selected by consideration of factors including compatibility with the chosen vector, secretion characteristics, ability to fold proteins correctly, and fermentation requirements, as well as any toxicity to the host of the product encoded by the DNA sequences to be expressed, and the ease of purification of the expression products. The practitioner will be able to select the appropriate host cells and expression mechanisms for a particular purpose.

Several strategies are available for the isolation and purification of recombinant GlcNAc T-Vb after expression in a host system. One method involves expressing the proteins in bacterial cells, lysing the cells, and purifying the protein by conventional means. Alternatively, one can engineer the DNA sequences for secretion from cells. See, e.g., Colley et al. (1989) *J. Biol. Chem.* 264:17619-17622, and U.S. Pat. No. 5,032,519, issued Jul. 16, 1991, which references describe purifying a sialyl transferase by engineering the cleavable signal peptide of human gamma-interferon onto the DNA sequence for the transferase. Larsen et al. (1990) *Proc. Natl. Acad. Sci. USA* 87:6674-6678, fused the DNA sequence for protein A to the amino-terminal end of a fucosyl transferase gene and expressed it as an excreted fusion protein. In these constructions, one can optionally remove the transmembrane region of these proteins that exists near the amino-terminus. After secretion the proteins are purified from the medium. Similar strategies are available for bacterial expression systems. Soluble GlcNAc T-Vb is similarly produced by fusing the portion of the coding sequence downstream of the transmembrane domain to suitable translation start site and signal peptide or peptide sequence which facilitates purification. A GlcNAc T-Vb protein, especially a soluble GlcNAc T-Vb protein, can be readily engineered to facilitate purification and/or immobilization to a solid support of choice. For example, a stretch of 6-8 histidines can be engineered through polymerase chain reaction or other recombinant DNA technology to allow purification of expressed recombinant protein over a nickel-charged nitrilotriacetic acid (NTA) column using commercially available materials. Other oligopeptide "tags" which can be fused to a protein of interest by such techniques include, without limitation, strep-tag (Sigma-Genosys, The Woodlands, Tex.) which directs binding to streptavidin or its derivative streptactin (Sigma-Genosys); a glutathione-S-transferase gene fusion system which directs binding to glutathione coupled to a solid support (Amersham Pharmacia Biotech, Uppsala, Sweden); a calmodulin-binding peptide fusion system which allows purification using a calmodulin resin (Stratagene, La Jolla, Calif.); a maltose binding protein fusion system allowing binding to an amylose resin (New England Biolabs, Beverly, Mass.); and an oligo-histidine fusion peptide system which allows purification using a $Ni^{2+}$-NTA column (Qiagen, Valencia, Calif.).

GlcNAc T-Vb has the same enzymatic activity as that described fro GlcNAc T-Va, i.e., UDP-N-acetylglucosamine:α-6-D-mannoside β(1,6)-N-acetylglucosaminyltransferase (EC 2.4.1.155), as determined by activity shown in vitro using the substrate described herein below. These enzymes are responsible for the synthesis of β-1,6 branch structure (-[GlcNAc-β-(1,6)Man-α(1,6)Man]-) found in both tri- and tetra-antennary N-linked oligosaccharides. Without wishing to be bound by any particular theory, the inventors believe that the GlcNAc T-Vb of the present invention has activity with O-linked mannose branched glycosylation substrates as well.

It is understood by those skilled in the art that the exemplified GlcNAc T-Vb coding sequences, provided herein in Tables 1, 4 and 5 and in SEQ ID NOs:1, 7 and 9, are representative of GlcNAc T-Vb from other vertebrate sources, especially of other mammalian sources, including humans. Table 3 and SEQ ID NOs:3 and 4 provide the mouse coding and amino acid sequences. The coding sequences for GlcNAc T-Vb provided herein are suitable for use in preparing or deriving PCR primers for identifying and/or amplifying sequences encoding human or other animal GlcNAc T-Vb, and/or for use as hybridization probes to identify clones encoding human, hamster, rat, other mammalian or other vertebrate GlcNAc T-Vb in appropriate genomic or cDNA libraries.

Species other than mouse and human contain genes encoding proteins which catalyze the same enzymatic reaction as GlcNAc T-Vb, which genes have significant sequence homology to the mouse and human sequences encoding GlcNAc T-Vb. One can isolate these homologous cDNAs and/or genes using the DNA sequences of this invention as probes or primers under standard hybridization conditions. This invention specifically contemplates and encompasses such sequences, i.e., those with at least 70%, 80%, 85% or 90% (and all integers between 70 and 100%) nucleotide sequence identity and/or which hybridize under conditions of moderate stringency and which have the same enzymatic activity.

A comparison of the human and partial mouse GlcNAc T-Vb nucleotide sequences are presented in Table 6.

Analysis of the coding regions of these sequences indicates that there is about 88% nucleotide sequence identity of the human sequence compared with the (partial) mouse sequence. Comparison of human and partial mouse amino acid sequences indicates that they are about 82-91% identical at the amino acid level, depending on the comparison program and the parameters set. See Table 6 for comparisons. In these tables, dots indicate similar amino acids, and vertical bars indicate identity. Gaps inserted to optimize alignment are treated as mismatches.

Thus, GlcNAc T-Vb coding sequences from vertebrate sources have significant sequence homology to the exemplified human and mouse GlcNAc T-V coding sequences, and the encoded GlcNAc T-V enzymes have a high degree of amino acid sequence identity as disclosed herein. It is obvious to one normally skilled in the art that human, mouse and other mammalian GlcNAc T-Vb cDNA clones, genomic clones and PCR amplification products can be readily isolated using standard procedures (i.e., hybridization under conditions of moderate stringency using the human or mouse coding sequences as probes) and the sequence information provided herein. It is further obvious to one normally skilled in the art that GlcNAc T-Vb cDNA and genomic clones, cDNA and genomic gene sequences, and amino acid sequences can be readily obtained and used for GlcNAc T-Vb from any mammalian species using standard procedures and the sequence information provided herein. The ordinary skilled artisan can utilize the exemplified sequences provided herein, or portions thereof, preferably at least 25-30 bases in length, in hybridization probes to identify cDNA (or genomic) clones encoding GlcNAc T-V, where there is at least 70%, desirably at least 80%, preferably at least 85% sequence identity to the probe sequence using appropriate art-known hybridization techniques. The skilled artisan understands that the capacity of a cloned cDNA to encode functional GlcNAc T-Vb enzyme can be readily tested as taught herein.

Hybridization conditions appropriate for detecting various extents of nucleotide sequence homology between probe and target sequences and theoretical and practical consideration are given, for example in B. D. Hames and S. J. Higgins (1985) *Nucleic Acid Hybridization*, IRL Press, Oxford, and in Sambrook et al. (1989) supra. Under particular hybridization conditions the DNA sequences of this invention will hybridize to other DNA sequences having sufficient homology, including homologous sequences from different species. It is understood in the art that the stringency of hybridization conditions is a factor in the degree of homology required for hybridization. The skilled artisan knows how to manipulate the hybridization conditions so that the stringency of hybridization is at the desired level (high, medium, low). If attempts to identify and isolate the GlcNAc T-Vb gene from another mammalian source fail using high stringency conditions, the skilled artisan will understand how to decrease the stringency of the hybridization conditions so that a sequence with a lower degree of sequence homology will hybridize to the sequence used as a probe. The choice of the length and sequence of the probe is readily understood by the skilled artisan.

When a cDNA library is used as a source of GlcNAc T-Vb coding sequences, the skilled artisan will take steps to insure that the library is of high quality, i.e., that rare mRNAs will be represented and that large mRNAs (larger than about 3 kb) will be present as full length cDNA clones. If the artisan uses one of the commercially available or otherwise accessible cDNA libraries, he or she chooses one that meets the criteria taught herein. Providing for rare and/or large message representation is within the skill of the art.

The DNA sequences of this invention refer to DNA sequences prepared or isolated using recombinant DNA techniques. These include cDNA sequences, sequences isolated using PCR, DNA sequences isolated from their native genome, and synthetic DNA sequences. As used herein, this term is not intended to encompass naturally-occurring chromosomes or genomes. Sequences derived from the GlcNAc T-Vb gene can be used in studying the regulation of GlcNAc T-Vb expression in normal cells, in transformed cells and in metastatic tumor cells, and can be used in designing mechanisms, e.g., via antisense RNA or DNA, for inhibiting metastasis of tumor cells. These sequences can also be used to direct recombinant synthesis of GlcNAc T-Vb.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or proteolytic cleavage of a signal sequence to produce a "mature" protein. Accordingly, as used herein, the term "GlcNAc T-Vb" encompasses full-length polypeptides and modifications or derivatives thereof, such as glycosylated versions of such polypeptides, mature proteins, polypeptides retaining a signal peptide, truncated polypeptides having comparable biological activity, and the like. Expression of GlcNAc T-Vb in eukaryotic cell lines expressing biologically active glycoproteins allows efficient branch structure initiation directed by GlcNAc T-Vb, where desired.

It is well-known in the biological arts that certain amino acid substitutions can be made within a protein without affecting the functioning of that protein. Preferably such substitutions are of amino acids similar in size and/or charge properties. For example, Dayhoff et al. (1978) in *Atlas of Protein Sequence and Structure*, Volume 5, Supplement 3, Chapter 22, pages 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

It will be a matter of routine experimentation for the ordinary skilled artisan to use the DNA sequence information presented herein to optimize GlcNAc T-Vb expression in a particular expression vector and cell line for a desired purpose. A cell line genetically engineered to contain and express a GlcNAc T-Vb coding sequence is useful for the recombinant expression of protein products with the characteristic glycosylation dependent on GlcNAc T-Vb modification of glycoproteins. Any means known to the art can be used to introduce an expressible GlcNAc T-Vb coding sequence into a cell to produce a recombinant host cell, i.e., to genetically engineer such a recombinant host cell. Recombinant host cell lines which express high levels of GlcNAc T-Vb will be useful as sources for the purification of GlcNAc T-Vb, e.g., for studies of inhibitors of GlcNAc T-Vb activity for preventing or slowing metastasis of tumors. The coding sequence of GlcNAc T-Vb is useful in preparing an antisense construct specific for GlcNAc T-Vb for inhibiting GlcNAc T-V expression where that is desired, for example, in metastasizing tumor cells. GlcNAc T-Vb, as an integral part of cells or as a soluble enzyme, is useful for glycosylation or for remodeling of the glycosyl portions of glycoproteins, especially of recombinantly expressed glycoproteins. The GlcNAc T-Vb of the present invention is useful for remodeling glycoproteins to improved half-life in circulation in a mammal or avian species.

Soluble secreted GlcNAc T-Vb enzyme proteins can be produced using the disclosure provided herein. A soluble GlcNAc T-Vb is one which lacks the sequences in the amino terminal region of the protein which localize it to and bind it within the cell membrane, particularly within the Golgi apparatus. When the coding region of the enzymatically active portion of GlcNAc T-Vb, but not including the transmembrane region, is fused downstream of and in frame with a signal sequence coding sequence, and operably linked to transcriptional control sequences, and expressed in a suitable host cell, such as a mammalian cell, soluble GlcNAc T-Vb is expressed and secreted into the culture medium after the signal peptide portion is removed by specific protease cleavage. A soluble, secreted GlcNAc T-Vb is engineered from the human cDNA encoding GlcNAc T-Vb essentially as described in U.S. Pat. No. 5,032,519 (Paulson et al., issued Jul. 16, 1991; see also Chen et al. (1995) *Glycoconjugate J.* 12:813-823) with removal of the N-terminal 32 amino acids of human GlcNAc T-Vb. The DNA encoding the remainder of GlcNAc T-Vb0 is fused to the human gamma-interferon signal sequence coding region, and there is a Gln residue derived from the gamma-interferon at the N-terminus of the soluble GlcNAc T-Vb. The ordinary skilled artisan can readily produce soluble GlcNAc T-Vb derivatives using the sequences provided herein, taken with what is well known to the art. Spent medium from cells expressing the soluble GlcNAc T-Vb is chromatographed over a copper chelating column and over CM fast flow Sepharose to yield purified soluble GlcNAc T-Vb. Desirably, at least one protease inhibitor is added during the processing of the culture medium to reduce degradation of the recombinant enzyme.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

As used herein expression directed by a particular sequence is the transcription of an associated downstream sequence. If appropriate and desired for the associated sequence, there the term expression also encompasses translation (protein synthesis) of the transcribed RNA. When expression of a sequence of interest is "up-regulated," the expression is increased.

In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer molecule is present in the medium in or on which the organism is cultivated.

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a GlcNAc T-Vb encoding polynucleotide which is substantially separated from other polynucleotide sequences which naturally accompany it on human chromosome 17. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other GlcNAc T-Vb coding sequences, for example, those from other species of mammals or from other animals such as birds. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially cultured mammalian cells, wherein protein expression is desired. Usually the construct is suitable for replication in a host cell, such as cultured mammalian cell or a bacterium, but a multicellular eukaryotic host may also be appropriate, with or without integration within the genome of the host cell. Commonly used prokaryotic hosts include strains of *Escherichia coli*, although other prokaryotes, such as *Bacillus subtilis* or a pseudomonad, may also be used. Eukaryotic host cells include mammalian cells, yeast, filamentous fungi, plant, insect, amphibian and avian cell lines. Such factors as ease of manipulation, ability to appropriately glycosylate expressed proteins, degree and control of recombinant protein expression, ease of purification of expressed proteins away from cellular contaminants or other factors influence the choice of the host cell.

The polynucleotides may also be produced by chemical synthesis, e.g., by the phosphoramidite method described by Beaucage and Caruthers (1981) *Tetra. Letts.* 22: 1859-1862 or the triester method according to Matteuci et al. (1981) *J. Am. Chem. Soc.* 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature*, 334: 31-36. Many useful vectors for expression in bacteria, yeast, fungal, mammalian, insect, plant or other cells are well known in the art and may be obtained from such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art which is appropriate for the particular type of cell, including without limitation, transfection, transformation, lipofection or electroporation.

It is recognized by those skilled in the art that the DNA sequences may vary due to the degeneracy of the genetic code and codon usage. All DNA sequences which code for the GlcNAc T-Vb protein are included in this invention, including DNA sequences as given in Tables 1, 3-5 and 7 having an ATG preceding the coding region for the mature protein.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that the sequence of the exemplified GlcNAc T-Vb protein and the nucleotide sequence encoding it can be used to identify and isolate additional, nonexemplified nucleotide sequences which are functionally equivalent to the sequences given Tables 1, 3-5 and 7 (and in SEQ ID NOs:1, 3, 7, 9 and 11).

Hybridization procedures are useful for identifying polynucleotides with sufficient homology to the subject regulatory sequences to be useful as taught herein. The particular hybridization techniques is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescent reagent such as luciferin, or fluorescent compounds like fluorescein and its derivatives. Alternatively, the probes can be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak (1987) *DNA Probes*, Stockton Press, New York, N.Y., pp. 169-170, hereby incorporated by reference.

As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5× Denhardt's solution/0.1% SDS, and washing in 0.2×SSC/0.1% SDS at room temperature. An example of conditions of moderate stringency are hybridizing at 68° C. in 5×SSC/5× Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) *Current Protocols in Molecular Biology*, John Wiley & Sons, NY, N.Y., for further guidance on hybridization conditions.

Specifically, hybridization of immobilized DNA in Southern blots with $^{32}P$-labeled gene specific probes was performed by standard methods (Maniatis et al.) In general, hybridization and subsequent washes were carried out under moderate to high stringency conditions that allowed for detection of target sequences with homology to the exemplified GlcNAc T-Vb sequences. For double-stranded DNA gene probes, hybridization can be carried out overnight at 20-25° C. below the melting temperature (Tm) of the DNA hybrid in 6×SSPE 5× Denhardt's solution, 0.1% SDS, 0.1 mg/ml denatured DNA. The melting temperature is described by the following formula (Beltz, G. A., Jacobe, T. H., Rickbush, P. T., Chorbas, and F. C. Kafatos [1983] *Methods of Enzymology*, R. Wu, L, Grossman and K Moldave [eds] Academic Press, New York 100:266-285).

Tm=81.5° C.+16.6 Log [Na+]+0.41(+G+C)−0.61(% formamide)−600/length of duplex in base pairs.

Washes are typically carried out as follows: twice at room temperature for 15 minutes in 1×SSPE, 0.1% SDS (low stringency wash), and once at TM-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid 6×SSPE, 5× Denhardt's solution, 0.1% SDS, 0.1 mg/ml denatured DNA. Tm for oligonucleotide probes was determined by the following formula: TM(° C.)=2 (number T/A base pairs+4(number G/C base pairs) [Suggs, S. V. et al. (1981) *ICB-UCLA Symp. Dev. Biol. Using Purified Genes*, D. D. Brown (ed.), Academic Press, New York, 23:683-693].

Washes were typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence identity refers to homology (or identity) which is sufficient to enable the variant polynucleotide to function in the same capacity as the polynucleotide from which the probe was derived. Preferably, this sequence identity is greater than 70% or 80%, more preferably, this identity is greater than 85%, or this identity is greater than 90%, and or alternatively, this is greater than 95%. The degree of homology or identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage.

Polymerase Chain Reaction (PCR) is a repetitive, enzymatic, primed synthesis of a nucleic acid sequence. This procedure is well known and commonly used by those skilled in this art [see, e.g., Mullis, U.S. Pat. Nos. 4,683,195, 4,683,202, and 4,800,159; Saiki et al. (1985) *Science* 230: 1350-1354]. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Bal31 exonuclease can be conveniently used for time-controlled limited digestion of DNA. See, for example, Maniatis (1982) *Molecular Cloning: A Laboratory Manual*, Cold Spring Harbor Laboratory, New York, pages 135-139, incorporated herein by reference. See also Wei et al. (1983 *J. Biol. Chem.* 258: 13006-13512. By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original GlcNAc T-Vb encoding sequence. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3):349-59; Shortle, D, DiMaio, D., and Nathans, D. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain GlcNAc T-Vb activity.

DNA sequences having at least 70, 80, 85, 90 or 95% or greater identity to the recited DNA coding sequence of Tables 1, 3, 4, 5 or 7 (SEQ ID NOs:1, 3, 7, 9 or 11) and functioning to encode a GlcNAc T-Vb protein are within the scope of the present invention. Functional equivalents are included in the definition of a GlcNAc T-Vb encoding sequence. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Altschul et al. (1997) *Nucl. Acids Res.* 25: 3389-3402; see also Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) *Nucl. Acids. Res.* 25:3389-3402. When utilizing BLAST and Gapped BLAST programs, the default parameters of the respective programs (NBLAST and XBLAST) are used. See the National Center for Biotechnology Information on the internet.

Monoclonal or polyclonal antibodies, preferably monoclonal, specifically reacting with a protein of interest can be made by methods well known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1993) *Current Protocols in Molecular Biology*, Wiley Interscience/Greene Publishing, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

The following examples are provided for illustrative purposes as well as for enablement. These examples are not intended to limit the scope of the invention. The examples use many techniques well known and accessible to those skilled in the arts of molecular biology and biochemistry. It will be readily apparent to the skilled artisan that modifications of the methods disclosed herein may be made, and that there will be DNA sequence modifications which can be made with the maintenance of the desired result. It will be readily apparent to one of ordinary skill in the art that the nucleotide sequences and amino acid sequences disclosed herein make it unnecessary to repeat many of the examples to practice the invention.

All references cited in this application are expressly incorporated by reference herein to the extent that there is no inconsistency with the present disclosure.

EXAMPLES

Example 1

Isolation of PCR Fragment Containing Human GlcNAc T-Vb Sequences

A human brain cDNA library was purchased from Origene Technologies, Rockville, Md. The library was a 96 well panel of cDNA clones, with about 5000 clones per well.

The primers used to amplify the GlcNAc T-Vb coding sequence were Primer 1 (forward) 5'-CTTCGACCTCATC-TACACCGACTACCAC-3' (SEQ ID NO:5) and Primer 2 (reverse(5'-GCCAAACCCGATGAAGAGTTTGGCCTTG-3' (SEQ ID NO:6). For the initial screening of the brain cDNA and in subsequent amplifications, the following conditions were used:

- 0.2 mM dNTP (Fisher Scientific, Pittsburgh, Pa.)
- 0.3 µM Primers 1 and 2
- 0.5 U thermostable polymerase (Pfu, Stratagene, La Jolla, Calif.)

To carry out the PCR, the instrument was programmed as follows:

- 94° C.—5 min for one cycle
- 35 cycles: 94EC—30 sec
- 65° C.—30 sec
- 72° C.—1 min
- 72° C.—1 min for one cycle PCR reaction samples were loaded onto 2% agarose gels and electrophoresed at 120V for 60 min before photographing the gel using a Fluor S machine (BioRad Laboratories, Hercules, Calif.).

To determine the largest 5' region in the library, the following conditions were used:

- 0.2 mM dNTP (Fisher Scientific, Pittsburgh, Pa.)
- 0.3 µM Primer provided with the Origene library and Primer 2
- 0.5 U thermostable polymerase (Pfu, Stratagene, La Jolla, Calif.)

To carry out the PCR, the instrument was programmed as follows:

- 94° C.—5 min for one cycle for 10 cycles:
- 94° C.—30 sec for one cycle
- 68° C.—7 min for 35 cycles:
- 94° C.—30 sec
- 65° C.—30 sec
- 72° C.—7 min
- 72° C.—7 min for one cycle PCR reaction samples were loaded on a 0.7% agarose gel and electrophoresed at 120V for 60 min and then photographed using the Fluor S instrument.

After positive clones were identified from subplate D11 sample D8, 18 colonies were selected and inoculated into 5 ml aliquots of LB medium containing 100 µg/ml ampicillin. Cultures were incubated overnight at 37° C. overnight with shaking at 240 rpm. The following day plasmid DNA samples were purified using a mini-prep kit (Roche, Basel, CH) and template resuspended in 100 µl water. Each sample was then digested with NotI to determine insert size (12 µl water, 0.15 µl 100×BSA, 1.5 µl 10× buffer, 1 µl NotI). The digested samples were then loaded onto a 0.7% agarose gel and electrophoresed at 120V for 60 min. Samples C1 and D9 contained the largest inserts, and the DNA sequences of the inserts were determined.

Example 2

Assay of GlcNAc T-V Activity

A typical radiochemical assay for determining activity contains the following reagents which were dried in vacuo in a 1.5 ml conical centrifuge tube: 2 mM ADP (pyrophosphatase inhibitor, 2.5 mM β-methylGlcNAc (β-hexosaminidase inhibitor), $10^6$ cpm UDP-[6-$^3$H]-GlcNAc (10 cpm/pmol) and 1 mM of the synthetic acceptor (β-D-GlcNAc)-(1,2)-α-D-Man-(1,6)-β-D-Man-O—$(CH_2)_8CO_2$Me in a total volume of 10 microliters.

To initiate the reaction, 0.01 ml of sample, in a buffer containing 50 mM MES pH 6.0, 0.1% Surfact-Amps (Triton) X-100 (Pierce, Rockford, Ill.), is added to the dried reagents and incubated at 37° C. for several hrs.

To terminate the assay, 0.5 ml water is added to each tube, vortexed thoroughly, and the contents of the tubes are centrifuged. The supernatant is then loaded onto a pellicular C18 Sep-Pak column (Millipore, Bedford, Mass.) activated with methanol and pre-equilibrated with water. The columns are washed with 200 ml water to remove water-soluble radioactivity resulting from unreacted substrate and degradation products. The radiolabeled product of the GlcNAc T-V reaction is then eluted with a 0-100% step gradient of methanol, and radioactivity is quantitated by liquid scintillation counting. All assays are conducted in duplicate, and the results are averaged. Assays are done in at least two separate experiments and averaged. The variation between the values derived from duplicates or from separate experiments typically does not exceed ±10%.

Radiolabeled product is then separated from the unreacted acceptor and radiolabeled UDP-GlcNAc by virtue of the hydrophobic moiety using C-18 chromatography.

Once the GlcNAc T-V protein is purified, the parameters in the assay are optimized.

GlcNAc T-Vb protein is measured using the enzyme-linked immunosorbent assay described in Crawely et al. (1990) *Analytical Biochem.* 185:112-117. The ELISA uses unlabeled UDP-GlcNAc and a trisaccharide acceptor (β-D-GlcNAc)-(1,2)-α-D-Man-(1,6)-β-O-Man-D-$(CH_2)_8CO_2$Me coupled to BSA. This assay relies on the use of a polyclonal antibody specific for the tetrasaccharide-BSA product of the GlcNAc T-Vb reaction. Due to the extreme sensitivity of the ELISA, column fractions containing an inhibitory amount of NaCl, for example, could be assayed without prior dialysis by simply diluting the samples. Standard calibration curves are generated in each assay and absorbance (or relative activity) is correlated to a specific activity by comparison to values obtained for a sample of known GlcNAc activity, as measured in the radiochemical assay.

Example 3

Measurement of Small Amounts of Protein

The BCA protein assay (Pierce, Rockford, Ill.) is adapted for use in a microtiter plate format using standard polystyrene 96 well plates (Pierce, Rockford, Ill.) to assay column fractions for protein content during purifications. BSA serves as the standard protein.

Example 4

Production of Antibodies Specific for GlcNAc T-Vb

Antigenic peptides, especially from hydrophilic regions of the protein, derived from the amino acid sequence of GlcNAc T-Vb are prepared and conjugated to a carrier protein (e.g., keyhole limpet hemocyanin) and used to immunize rabbits or other suitable source of antibody specific for GlcNAc T-Vb. The peptide-carrier complex (about 3 mg mixed with 1.0 ml of Freund's complete adjuvant. The resulting emulsion is administered to two rabbits by injecting intradermally in the back with 50-75 µl/site or about 75 µg protein per site. Each rabbit receives booster injections of 150 µg per dose, prepared in the same way, 14 days after the initial dose, and each rabbit receives 75 µg at 21, 34, 57 and 64 days after the initial injection. 10-20 ml of blood is collected from an ear vein of each rabbit at weekly intervals, and serum is prepared and stored at −20° C. Serum samples with the highest activity are pooled. Similarly, the entire protein can be incorporated into immunogenic compositions (with the appropriate adjuvants) and administered to experimental animals, e.g., rabbits, for the production of antibodies.

Alternatively, monoclonal antibodies specific for GlcNAc T-Vb are prepared according to standard procedures (e.g., Campbell (1984) *Monoclonal Antibody Technology: Laboratory Techniques in Biochemistry and Molecular Biology* (Burdon and van Knippenberg, eds.) Vol. 13, Elsevier, Amsterdam; Harlow and Lane (1988) *Antibodies: A Laboratory Manual*, Cold Spring Harbor Laboratory, Cold Spring Harbor, N.Y.) after immunization of mice with GlcNAc T-Vb-derived peptide antigens.

Sequences to be incorporated into immunogenic compositions can be selected from the particularly hydrophilic regions of the human GlcNAc T-V protein (see FIG. 1). Synthetic oligopeptides can be produced using automated technology and conjugated to carrier protein, or the chosen hydrophilic sequence can be incorporated into a multiantigenic peptide (see, e.g. Tam, J. P. (1988) *Proc. Natl. Acad. Sci. USA* 85: 5409-5413; Posnett et al. (1988) *J. Biol. Chem.* 263: 1719-1725).

Example 5

Isolation of Additional cDNA Clones for GlcNAc T-Vb

To prepare additional cDNA clones, messenger RNA (mRNA) is isolated by standard procedures (Maniatis et al., 1982) from brain. Poly$(A)^+$ mRNA is selected using an mRNA separator kit (Clontech Lab, Inc., Palo Alto, Calif.), and cDNA is synthesized using commercially available materials. Column-fractionated double-stranded cDNA was ligated into a suitable linearized vector such as the pSPORT-1 plasmid vector (BRL Life Technologies, Inc., Bethesda, Md.) and transformed into *Escherichia coli* (strain DH10B, for example) cells by electroporation (Dower et al. (1988) *Nucl. Acids Res.* 16:6127-6145) Transformed *E. coli* DH10B cells are propagated as several individual pools, and plasmid DNA is isolated from each pool.

An aliquot of plasmid DNA from each pool of the cDNA library was combined to form a cDNA library DNA mixture. PCR is carried out on the cDNA pool using primers 1 and 2 as described above.

An aliquot of the reaction products is analyzed by agarose gel electrophoresis (0.8% agarose in Tris Borate EDTA buffer (TBE) containing ethidium bromide) and the gel is photographed.

Example 6

DNA Sequence Analysis

The DNA of interest is sequenced using Taq DyeDioxy Terminator cycle sequencing kits (Applied Biosystems, Inc., Foster City, Calif.) and an automated DNA sequencer (Applied Biosystems 373A) following the manufacturer's instructions. The DNA fragment is sequenced after it is passed over a Centricon-100 unit (Amicon, Beverly, Mass.) and washed with sterile water. In some instances, sequences are derived after the PCR fragment is subcloned into a pUC13 vector (Promega, Madison, Wis.). Nucleotide sequencing is carried out using synthetic oligonucleotides as primers.

Alternatively, cDNA clones encoding GlcNAc T-Vb can be isolated using the following strategy. Total RNA is prepared in parallel isolations from mouse brain tissue (or brain tissue of the species of interest), according to standard procedures as described in Sambrook et al. (eds.) (1989) supra. The Poly(A)+ fraction of the total RNA is prepared by chromatography over Oligo(dT) cellulose chromatography as described in Sambrook et al. (eds.) (1989) supra. Polyadenylated mRNA encoding GlcNAc T-Vb is included within the Poly(A)+ RNA thus prepared.

cDNA libraries are prepared using the poly(A)+ RNA prepared from mouse or other brain cells according to the procedure of Sambrook et al. (eds.) (1989) supra. Cloning of the cDNA population into a suitable vector (such as λgt11) is done according to standard protocols. (See, e.g., Huynh et al. (1985) in *DNA Cloning, a Practical Approach,* Vol. 1 (Glover, D. M., ed.), IRL Press, Washington, D.C., pp. 49-78.) Commercially-available cDNA libraries can also be screened for GlcNAc T-Vb clones.

The cDNA libraries are screened for sequences encoding GlcNAc T-Vb by plaque hybridization under low stringency conditions using the human amplimer of Example 1, radiolabeled by random hexamer labeling as described in Sambrook et al. (eds.) (1989) supra. Clones specifically hybridizing the amplimer sequence are selected for further analysis (restriction endonuclease digestion, nucleotide sequence determination).

Genomic clones encoding GlcNAc T-Vb can be identified from a rat (or mouse or other mammal) genomic library using Primer 1 and Primer 2, or the amplimer where PCR synthesized as above was primed with Primer 1 and Primer 2 to identify appropriate genomic sequences.

From the clones analyzed it is possible to reconstruct the entire coding sequence of GlcNAc T-Vb. If a full-length coding sequence is not reconstructed, further primers can be designed using sequences near the ends of the sequenced region for use in the RACE procedure (Rapid Amplification of cDNA Ends) as described in Frohman et al. (1988) *Proc. Natl. Acad. Sci. USA* 85: 8998-9002. Where the entire gene is desired, genomic libraries can be screened, and "walking" procedures known in the art are used to extend in both directions.

Example 7

Assay of GlcNAc T-V Activity

In an alternate approach for assay of enzymatic activity of recombinant GlcNAc T-Vb, the coding sequence is fused to the N-terminal Protein A coding sequence as described in Larsen et al. (1989) *Proc. Natl. Acad. Sci. USA* 86: 8227-8231. The resultant recombinant plasmid is then introduced into mammalian cells such that cells which have incorporated the cDNA sequences survive in culture. Because the fusion protein contains the N-terminal sequences of Protein A, the fusion protein is directed to the secretion pathway and released from the cells. After removal of the cells by centrifugation, the culture medium is assayed for GlcNAc T-V activity as described herein. A portion of the cell-free medium is chromatographed over an IgG column to which the N-terminal Protein A sequences bind, causing GlcNAc T-Vb activity to be retained on the column.

A second approach for assay of recombinant GlcNAc T-Vb is to insert the complete cDNA into a vector under the control of regulatory sequences which will allow expression in the chosen mammalian host cells. The host cell chosen is a GlcNAc T-Va-deficient variant of the mouse lymphoma BW5147 cell line, which variant is PHA 2.1; this variant cell line is described in Cummings et al. (1982) *J. Biol. Chem.* 257: 13421-13427. An alternative GlcNAc T-V-deficient cell line is the Lec4 variant of CHO cells, described by Stanley, P. (1983) *Methods Enzymol.* 96: 157-184. Both variant cells lines were selected for growth in the presence of the cytotoxic lectin L-phytohemagglutinin, which binds to the galactosylated product of GlcNAc T-V. Expression of the cDNA sequences encoding the GlcNAc T-V restores GlcNAc T-V activity and lectin sensitivity to these variant cell lines.

Example 8

Construction of a Vector Engineered to Express Secretable GlcNAc T-Vb

Soluble, secreted recombinant human GlcNAc T-Vb with enzymatic activity is produced by the methods described in U.S. Pat. No. 5,032,519, "Method for Producing Secretable Glycosyltransferases and Other Golgi Processing Enzymes," J. Paulson et al., Jul. 16, 1991. Briefly, the membrane anchor domain and the Golgi apparatus retention signal are deleted and the sequence information for expressing a cleavable secretion signal are inserted in the GlcNAc T-Vb genetic material. After transfection of the modified GlcNAc T-V sequences into cells, the cells secrete into the culture media soluble enzymatically active GlcNAc T-Vb. The GlcNAc T-Vb can be readily purified from the culture media for further use.

Using standard procedures and following the teachings of the cited patent, the cleavable signal sequence of human gamma-interferon was fused with the human GlcNAc T-Vb at the sequence corresponding to amino acid number 33 (see Table 2 or SEQ ID NO:2) This chimera has replaced the GlcNAc T-Vb putative cytoplasmic domain (amino acids 1-10), transmembrane domain (amino acids 11-32) and a portion of the stem region with a fragment coding for the 23 amino acid signal peptide and first amino acid of mature human gamma-interferon. The resulting fusion gene product is cleaved to yield secretable GlcNAc T-V containing one amino acid from the gamma-interferon (Gln) at the new $NH_2$-terminus.

COS-7 cells are transfected with the mammalian expression vector containing the secretable human GlcNAc T-Vb cDNA insert by electroporation. The cells are transferred to T-75 culture flasks containing 10 ml of DMEM, 10% FBS (fetal bovine serum) and a 1× solution of Glutamine, Penicillin and Streptomycin (Irvine Scientific, Santa Ana, Calif.; final concentrations in medium: L-Glutamine 0.292 mg/ml; Penicillin G, 100 units/ml; Streptomycin sulfate 100 μg/ml) After a 7 hour incubation at 37° C., the medium is replaced with 7 ml of DMEM, 1% FBS and 1×GPS and incubation continued for an additional 3 days. The cell conditioned medium from each COS-7 plasmid transfection flask is collected and centrifuged to pellet cells and debris. The clear supernatant is frozen at −70° C. until analyzed by radiochemical assay as described in U.S. Pat. Nos. 5,602,003 and 6,015,701.

The secreted human GlcNAc T-Vb expression vector is transfected into CHO dhfr⁻ cells by the calcium phosphate precipitation method (Graham and van der Eb, *Virology* (1973) 52:456-467) modified as described by Wigler et al. (*Cell* (1978) 41:725-731) and Lewis et al. (*Somatic Cell Genetics* (1980) 6:333-347). Following selection by growth in media containing 5% dialyzed FBS (Irvine Scientific), pools and clones of stably transfected CHO dhfr⁻ cells are obtained. Cell conditioned media from the transfected CHO dhfr⁻ cell lines are collected and analyzed by the radionucleotide assay. The CHO dhfr⁻ cell line which produces the highest amount of active soluble GlcNAc T-Vb as determined by the radiochemical assay is used to seed a spinner cell culture flask. The cells are propagated in suspension cell culture and then used to seed roller bottles at an initial seeding density of 2.5×10⁷ cells in 200 ml of a 50/50 mixture of DMEM and F-12 media (Gibco) supplemented with 5% dialyzed FBS, 1× non-essential amino acids (Gibco) and 2 mM L-glutamine (Gibco). After three days the roller bottles are shifted to 200 ml of serum-free medium. Harvests are collected at 6-day intervals with new serum-free medium added after each harvest. Conditioned medium is harvested and concentrated by cross-flow ultrafiltration through Mini Sartocon polysulfone modules (Sartorius Corporation, Bohemia, N.Y.) and then stored at −80° C. prior to purification. Radionucleotide assays are carried out to analyze the GlcNAc T-V activity in the concentrated conditioned medium.

20-fold concentrated cell conditioned medium is the starting material for soluble GlcNAc T-Vb purification. Soluble GlcNAc T-Vb can be purified from the culture supernatant using art-known techniques.

Protein assays are carried out using the BCA microtiter plate assay method. SDS-PAGE is done using 10% (1.5 mm thickness) gels on a Bio-Rad mini gel system.

TABLE 1

| Nucleotide Sequence Encoding Human GlcNAc T-Vb (SEQ ID NO:1) | |
|---|---|
| gccagcatct tgtagttgag ctctctttat cctatagtgg gggggccctc ctgggtctgg | 60 |
| agctcagccc ccatcctttc attctcccctt gcttccttca ctcatgcact cattcgtaaa | 120 |
| acatttgtgc agccggtacg tggtggagcg tcagggcacg atgcccttc ctgccctcct | 180 |
| gacccgcctc cttcctctcc gcaggctttt tgtcctgggc atcggcttct tcactctctg | 240 |
| cttcctgatg acgtctctgg gaggccagtt ctcggcccgg cgcctggggg actgccatt | 300 |
| caccatccgc acagaagtga tgggggccc cgagtcccgc ggcgtcctgc gcaagatgag | 360 |
| cgacctgctg gagctgatgg tgaagcgcat ggacgcactg gccaggctgg agaacagcag | 420 |
| tgagctgcac cgggccggcg gcgacctgca cttttcccgca gacaggatgc cccctggggc | 480 |
| cggcctcatg gagcggatcc aggctattgc ccagaacgtc tccgacatcg ctgtgaaggt | 540 |
| ggaccagatc ctgcgccaca gtctgctcct gcacagcaag gtgtcagaag ccggcggga | 600 |
| ccagtgtgag gcacccagtg accccaagtt ccctgactgc tcaggaagg tggagtggat | 660 |
| gcgtgcccgc tggacctctg accctgcta cgccttcttt ggggtggacg caccgagtg | 720 |
| ctccttcctc atctacctca gtgaggtcga gtggttctgc ccccgctgc ctggaggaa | 780 |
| ccagacggct gcccagaggg cacccaagcc cctccccaaa gtccaggcag ttttccgaag | 840 |
| caacctgtcc caccttctgg acctgatggg cagcggaag gagtccctga tcttcatgaa | 900 |
| gaagcggacc aagaggctca gcccagtg ggcgctggct gcccagcgcc tggcacagaa | 960 |
| gctgggggcc acccagaggg accagaagca gatcctggtc cacatcggct tcctgacgga | 1020 |
| ggagtccggg gacgtgttca gccctcgggt cctgaagggc gggcccctag gggagatggt | 1080 |
| gcagtgggcg gacattctga ctgcactcta tgtcctgggc catggcctgc gggtcacagt | 1140 |
| ctcccctgaag gagctgcaga gtaacttagg ggtaccgcca ggccgcggaa gctgcccgct | 1200 |
| caccatgccc ctgcccttcg acctcatcta caccgactac cacggcctgc agcagatgaa | 1260 |
| gcggcacatg ggactctcct tcaagaagta ccggtgccga atcagggtca tcgacacctt | 1320 |
| cgggacggaa cctgcgtaca accacgagga gtacgccacg ctgcacgct accggaccaa | 1380 |
| ctggggctac tggaacctca ccccaagca gttcatgacc atgtttcctc atacccccga | 1440 |
| caactccttc atgggcttcg tgtccgagga gctcaacgag acggagaagc ggctcatcaa | 1500 |
| aggcggcaag gccagcaaca tggccgtggt gtacggcaag gaggcgagca tctggaaggg | 1560 |
| gaaggagaag ttcctgggca tcctgaacaa atacatggag atccatggca ccgtgtacta | 1620 |
| cgagagccag cggccccccg aggtgccagc ctttgtgaag aaccacggcc tcttaccgca | 1680 |
| gcctgagttt cagcagctgc tgcgcaaggc caaactcttc atcgggtttg gcttcccctta | 1740 |
| cgagggcccc gccccctgg aggccatcgc caatggttgc atcttcctgc agtcccgctt | 1800 |
| cagcccgccc cacagctccc tcaaccacga gttcttccga ggcaagccca cctccagaga | 1860 |
| ggtgttctcc cagcatccct acgcggagaa cttcatcggc aagccccacg tgtggacagt | 1920 |
| cgactacaac aactcagagg agtttgaagc agccatcaag gccattatga gaactcaggt | 1980 |
| agaccctac ctaccctacg agtacacctg cgaggggatg ctggagcgga tccacgccta | 2040 |
| catccagcac caggacttct gcagagctcc agaccctgcc ctaccagagg cccacgcccc | 2100 |
| gcagagcccc tttgtcctgg cccccaatgc caccacctc gagtgggctc ggaacaccag | 2160 |
| cttggctcct ggggcctggc ccccgcgca cgccctgcgg gcctggctgg ccgtgcctgg | 2220 |
| gagggcctgc accgacacct gcctggacca cgggctaatc tgtgagccct ccttcttccc | 2280 |
| cttcctgaac agccaggacg ccttcctcaa gctgcaggtg cctgtgaca gcaccgagtc | 2340 |

TABLE 1-continued

Nucleotide Sequence Encoding Human GlcNAc T-Vb (SEQ ID NO:1)

```
ggagatgaac cacctgtacc cggcgttcgc ccagcctggc caggagtgct acctgcagaa    2400
ggagcctctg ctcttcagct gcgccggctc caacaccaag taccgccggc tctgcccctg    2460
ccgcgacttc gcaagggcc aggtggcctt gtgccagggc tgtctgtgaa tccgcctctg     2520
ccgccctgcc tggcacccac gctggctctc tcctgcc                              2557
```

TABLE 2

Amino Sequence of Human GlcNAc T-Vb

| | | | | | | | | | | | | | | |
|---|---|---|---|---|---|---|---|---|---|---|---|---|---|---|
| Met | Ala | Leu | Pro | Ala | Leu | Leu | Thr | Arg | Leu | Leu | Pro | Leu | Arg | Arg | Leu |
| 1 | | | | 5 | | | | | 10 | | | | | 15 | |
| Phe | Val | Leu | Gly | Ile | Gly | Phe | Phe | Thr | Leu | Cys | Phe | Leu | Met | Thr | Ser |
| | | | 20 | | | | | 25 | | | | | 30 | | |
| Leu | Gly | Gly | Gln | Phe | Ser | Ala | Arg | Arg | Leu | Gly | Asp | Ser | Pro | Phe | Thr |
| | | 35 | | | | | 40 | | | | | 45 | | | |
| Ile | Arg | Thr | Glu | Val | Met | Gly | Gly | Pro | Glu | Ser | Arg | Gly | Val | Leu | Arg |
| | 50 | | | | | 55 | | | | | 60 | | | | |
| Lys | Met | Ser | Asp | Leu | Leu | Glu | Leu | Met | Val | Lys | Arg | Met | Asp | Ala | Leu |
| 65 | | | | | 70 | | | | | 75 | | | | | 80 |
| Ala | Arg | Leu | Glu | Asn | Ser | Ser | Glu | Leu | His | Arg | Ala | Gly | Gly | Asp | Leu |
| | | | | 85 | | | | | 90 | | | | | 95 | |
| His | Phe | Pro | Ala | Asp | Arg | Met | Pro | Pro | Gly | Ala | Gly | Leu | Met | Glu | Arg |
| | | | 100 | | | | | 105 | | | | | 110 | | |
| Ile | Gln | Ala | Ile | Ala | Gln | Asn | Val | Ser | Asp | Ile | Ala | Val | Lys | Val | Asp |
| | | 115 | | | | | 120 | | | | | 125 | | | |
| Gln | Ile | Leu | Arg | His | Ser | Leu | Leu | His | Ser | Lys | Val | Ser | Glu | Gly |
| | 130 | | | | | 135 | | | | | 140 | | | | |
| Arg | Arg | Asp | Gln | Cys | Glu | Ala | Pro | Ser | Asp | Pro | Lys | Phe | Pro | Asp | Cys |
| 145 | | | | | 150 | | | | | 155 | | | | | 160 |
| Ser | Gly | Lys | Val | Glu | Trp | Met | Arg | Ala | Arg | Trp | Thr | Ser | Asp | Pro | Cys |
| | | | | 165 | | | | | 170 | | | | | 175 | |
| Tyr | Ala | Phe | Phe | Gly | Val | Asp | Gly | Thr | Glu | Cys | Ser | Phe | Leu | Ile | Tyr |
| | | | 180 | | | | | 185 | | | | | 190 | | |
| Leu | Ser | Glu | Val | Glu | Trp | Phe | Cys | Pro | Pro | Leu | Pro | Trp | Arg | Asn | Gln |
| | | 195 | | | | | 200 | | | | | 205 | | | |
| Thr | Ala | Ala | Gln | Arg | Ala | Pro | Lys | Pro | Leu | Pro | Lys | Val | Gln | Ala | Val |
| | 210 | | | | | 215 | | | | | 220 | | | | |
| Phe | Arg | Ser | Asn | Leu | Ser | His | Leu | Leu | Asp | Leu | Met | Gly | Ser | Gly | Lys |
| 225 | | | | | 230 | | | | | 235 | | | | | 240 |
| Glu | Ser | Leu | Ile | Phe | Met | Lys | Lys | Arg | Thr | Lys | Arg | Leu | Thr | Ala | Gln |
| | | | | 245 | | | | | 250 | | | | | 255 | |
| Trp | Ala | Leu | Ala | Ala | Gln | Arg | Leu | Ala | Gln | Lys | Leu | Gly | Ala | Thr | Gln |
| | | | 260 | | | | | 265 | | | | | 270 | | |
| Arg | Asp | Gln | Lys | Gln | Ile | Leu | Val | His | Ile | Gly | Phe | Leu | Thr | Glu | Glu |
| | | 275 | | | | | 280 | | | | | 285 | | | |
| Ser | Gly | Asp | Val | Phe | Ser | Pro | Arg | Val | Leu | Lys | Gly | Gly | Pro | Leu | Gly |
| | 290 | | | | | 295 | | | | | 300 | | | | |
| Glu | Met | Val | Gln | Trp | Ala | Asp | Ile | Leu | Thr | Ala | Leu | Tyr | Val | Leu | Gly |
| 305 | | | | | 310 | | | | | 315 | | | | | 320 |

TABLE 2-continued

Amino Sequence of Human GlcNAc T-Vb

His Gly Leu Arg Val Thr Val Ser Leu Lys Glu Leu Gln Ser Asn Leu
                325                 330                 335

Gly Val Pro Pro Gly Arg Gly Ser Cys Pro Leu Thr Met Pro Leu Pro
            340                 345                 350

Phe Asp Leu Ile Tyr Thr Asp Tyr His Gly Leu Gln Gln Met Lys Arg
            355                 360                 365

His Met Gly Leu Ser Phe Lys Lys Tyr Arg Cys Arg Ile Arg Val Ile
    370                 375                 380

Asp Thr Phe Gly Thr Glu Pro Ala Tyr Asn His Glu Glu Tyr Ala Thr
385                 390                 395                 400

Leu His Gly Tyr Arg Thr Asn Trp Gly Tyr Trp Asn Leu Asn Pro Lys
                405                 410                 415

Gln Phe Met Thr Met Phe Pro His Thr Pro Asp Asn Ser Phe Met Gly
            420                 425                 430

Phe Val Ser Glu Glu Leu Asn Glu Thr Glu Lys Arg Leu Ile Lys Gly
            435                 440                 445

Gly Lys Ala Ser Asn Met Ala Val Val Tyr Gly Lys Glu Ala Ser Ile
    450                 455                 460

Trp Lys Gly Lys Glu Lys Phe Leu Gly Ile Leu Asn Lys Tyr Met Glu
465                 470                 475                 480

Ile His Gly Thr Val Tyr Tyr Glu Ser Gln Arg Pro Pro Glu Val Pro
                485                 490                 495

Ala Phe Val Lys Asn His Gly Leu Leu Pro Gln Pro Glu Phe Gln Gln
            500                 505                 510

Leu Leu Arg Lys Ala Lys Leu Phe Ile Gly Phe Gly Phe Pro Tyr Glu
            515                 520                 525

Gly Pro Ala Pro Leu Glu Ala Ile Ala Asn Gly Cys Ile Phe Leu Gln
    530                 535                 540

Ser Arg Phe Ser Pro Pro His Ser Ser Leu Asn His Glu Phe Phe Arg
545                 550                 555                 560

Gly Lys Pro Thr Ser Arg Glu Val Phe Ser Gln His Pro Tyr Ala Glu
                565                 570                 575

Asn Phe Ile Gly Lys Pro His Val Trp Thr Val Asp Tyr Asn Asn Ser
            580                 585                 590

Glu Glu Phe Glu Ala Ala Ile Lys Ala Ile Met Arg Thr Gln Val Asp
            595                 600                 605

Pro Tyr Leu Pro Tyr Glu Tyr Thr Cys Glu Gly Met Leu Glu Arg Ile
    610                 615                 620

His Ala Tyr Ile Gln His Gln Asp Phe Cys Arg Ala Pro Asp Pro Ala
625                 630                 635                 640

Leu Pro Glu Ala His Ala Pro Gln Ser Pro Phe Val Leu Ala Pro Asn
                645                 650                 655

Ala Thr His Leu Glu Trp Ala Arg Asn Thr Ser Leu Ala Pro Gly Ala
            660                 665                 670

Trp Pro Pro Ala His Ala Leu Arg Ala Trp Leu Ala Val Pro Gly Arg
            675                 680                 685

Ala Cys Thr Asp Thr Cys Leu Asp His Gly Leu Ile Cys Glu Pro Ser
    690                 695                 700

Phe Phe Pro Phe Leu Asn Ser Gln Asp Ala Phe Leu Lys Leu Gln Val
705                 710                 715                 720

TABLE 2-continued

Amino Sequence of Human GlcNAc T-Vb

Pro Cys Asp Ser Thr Glu Ser Glu Met Asn His Leu Tyr Pro Ala Phe
                725                 730                 735

Ala Gln Pro Gly Gln Glu Cys Tyr Leu Gln Lys Glu Pro Leu Leu Phe
            740                 745                 750

Ser Cys Ala Gly Ser Asn Thr Lys Tyr Arg Arg Leu Cys Pro Cys Arg
            755                 760                 765

Asp Phe Arg Lys Gly Gln Val Ala Leu Cys Gln Gly Cys Leu
        770                 775                 780

TABLE 3

Coding Sequence (SEQ ID NO:3) and Deduced Amino Acid
Sequence (SEQ ID NO:4) for Monse GlcNAc T-Vb

| | |
|---|---:|
| ggcgcccgcc gcgggaagcc cgtttgcgcg ccgcggcgcc gtcccgccca gccagcgagc | 60 |
| ctagcaggca gacgcgcggc cggcgatctg ggggcgcgcc gcctcgcctt ccccaaaatg | 120 |
| tgaatcgggg agggcggaga cgcagagagc gcccggcccc aagctctcgc cgaacccctg | 180 |
| ccctgcgcgc ccaggccgcg ccgtgccccg cgcggggctg cagagccacc gtgccccgcg | 240 |
| ctccctcggt gctgcgaccc cccggcttcg ggccgcagcg gcttcgtggt tcccgaggcg | 300 |
| gtcagagccg ggcccaggac ggtgcgtccg gcctcgcccc cggcttctcg cccagacaag | 360 |

```
tttgaaca atg atc aca gtc aac cca gat ggg aag ata atg gtc aga aga         410
         Met Ile Thr Val Asn Pro Asp Gly Lys Ile Met Val Arg Arg
           1               5                  10 tgc ctg gtc acc ctg aga ccc ttt cgg ctg ttt gtc ctg ggc atc ggc         458
Cys Leu Val Thr Leu Arg Pro Phe Arg Leu Phe Val Leu Gly Ile Gly
 15                  20                  25                  30 ttc ttc act ctc tgc ttc ctg atg aca tct ttg gga ggc cag ttc tct         506
Phe Phe Thr Leu Cys Phe Leu Met Thr Ser Leu Gly Gly Gln Phe Ser
                 35                  40                  45 gcc cgg cgc ctg ggg gac tcg ccc ttc acc atc cgc aca gaa gtg cca         554
Ala Arg Arg Leu Gly Asp Ser Pro Phe Thr Ile Arg Thr Glu Val Pro
         50                  55                  60 ggc agc cca gag tca cgt ggt gcc ctt cgc aag atg agc gac ctg ctg         602
Gly Ser Pro Glu Ser Arg Gly Ala Leu Arg Lys Met Ser Asp Leu Leu
         65                  70                  75 gag ctg atg gtg aag cgc atg gat atg ctg gcc agg ctg gag aat agc         650
Glu Leu Met Val Lys Arg Met Asp Met Leu Ala Arg Leu Glu Asn Ser
         80                  85                  90 agc gag ctg cac cgg act gcc agt gtg gcg cac tta gcc gca gac agg         698
Ser Glu Leu His Arg Thr Ala Ser Val Ala His Leu Ala Ala Asp Arg
 95                 100                 105                 110 ctc acc cct ggg gcc agc ctc att gaa agg atc cag gcc att gcc cag         746
Leu Thr Pro Gly Ala Ser Leu Ile Glu Arg Ile Gln Ala Ile Ala Gln
                115                 120                 125 aat gtg tct gac atc gct gtg aag gtg gac cag atc ctg cgc cac agc         794
Asn Val Ser Asp Ile Ala Val Lys Val Asp Gln Ile Leu Arg His Ser
        130                 135                 140 ctg att ctg cat agc aag gtg tct gaa ggt cgg agg gac cag tgt gaa         842
Leu Ile Leu His Ser Lys Val Ser Glu Gly Arg Arg Asp Gln Cys Glu
        145                 150                 155 gca ccc agt gac ccc aag ttc cct gac tgt tcc ggg aaa gtg gag tgg         890
Ala Pro Ser Asp Pro Lys Phe Pro Asp Cys Ser Gly Lys Val Glu Trp
160                 165                 170
```

TABLE 3-continued

Coding Sequence (SEQ ID NO:3) and Deduced Amino Acid
Sequence (SEQ ID NO:4) for Monse GlcNAc T-Vb

| | |
|---|---:|
| atg cgc gcc cgc tgg acc tct gac ccc tgc tac gcc ttc ttt gga gta<br>Met Arg Ala Arg Trp Thr Ser Asp Pro Cys Tyr Ala Phe Phe Gly Val<br>175                            180                          185                      190 | 938 |
| gac ggc act gag tgc tcc ttc ctc atc tac ctc agt gag gtt gag tgg<br>Asp Gly Thr Glu Cys Ser Phe Leu Ile Tyr Leu Ser Glu Val Glu Trp<br>                          195                          200                          205 | 986 |
| ttc tgt ccc ccg ttg ccc tgg agg aac cag aca gct gcc cgg aca gcc<br>Phe Cys Pro Pro Leu Pro Trp Arg Asn Gln Thr Ala Ala Arg Thr Ala<br>                    210                          215                          220 | 1034 |
| ccc aag tcc ctt ccc aga gtc cag gct gtg ttc cga agc aac ctg tcc<br>Pro Lys Ser Leu Pro Arg Val Gln Ala Val Phe Arg Ser Asn Leu Ser<br>             225                          230                          235 | 1082 |
| cac ctc ctg gag ctg atg ggc agt ggg aag gag tcc ctc atc ttc atg<br>His Leu Leu Glu Leu Met Gly Ser Gly Lys Glu Ser Leu Ile Phe Met<br>      240                        245                          250 | 1130 |
| aag aag cga acc agg cgg ttc acc gca cag tgg acc aag gct gcc aag<br>Lys Lys Arg Thr Arg Arg Phe Thr Ala Gln Trp Thr Lys Ala Ala Lys<br>255                            260                          265                          270 | 1178 |
| tac ctg gca cag aag ctg ggg gac att cgg agg gac cag aag caa atc<br>Tyr Leu Ala Gln Lys Leu Gly Asp Ile Arg Arg Asp Gln Lys Gln Ile<br>                    275                          280                          285 | 1226 |
| ctt gtc cac att ggc ttc ctg aca gag gag tct ggg gac gtg ttc agc<br>Leu Val His Ile Gly Phe Leu Thr Glu Glu Ser Gly Asp Val Phe Ser<br>      290                        295                          300 | 1274 |
| cca agg gta ctg aag ggc ggg cct ctg gga gag atg gta cag tgg gca<br>Pro Arg Val Leu Lys Gly Gly Pro Leu Gly Glu Met Val Gln Trp Ala<br>             305                          310                          315 | 1322 |
| gac atc ctg gct gct ctc tac gtg ctg ggc cat agc ctg cgg atc aca<br>Asp Ile Leu Ala Ala Leu Tyr Val Leu Gly His Ser Leu Arg Ile Thr<br>      320                        325                          330 | 1370 |
| gtc tcc ctg aag gag ctg cag agt aac tta ggg gtg ccg cca ggc cgg<br>Val Ser Leu Lys Glu Leu Gln Ser Asn Leu Gly Val Pro Pro Gly Arg<br>335                            340                          345                          350 | 1418 |
| ggg aac tgc cca ctc acc gta cct ctg cct ttt gac ctc atc tac acg<br>Gly Asn Cys Pro Leu Thr Val Pro Leu Pro Phe Asp Leu Ile Tyr Thr<br>                    355                          360                          365 | 1466 |
| gac tat cac ggc ttg cag cag atg aaa cag cac atg gga ctg tcc ttc<br>Asp Tyr His Gly Leu Gln Gln Met Lys Gln His Met Gly Leu Ser Phe<br>             370                          375                          380 | 1514 |
| aag aag tac cgg tgc aga atc cga gtc atc gac acc ttt ggg acg gag<br>Lys Lys Tyr Arg Cys Arg Ile Arg Val Ile Asp Thr Phe Gly Thr Glu<br>      385                        390                          395 | 1562 |
| cca gcg tac aac cac gag gag tat gcc acg ctg cac ggc tac cgg acc<br>Pro Ala Tyr Asn His Glu Glu Tyr Ala Thr Leu His Gly Tyr Arg Thr<br>400                            405                          410 | 1610 |
| aac tgg ggt tac tgg aac ctc aac ccc aag cag ttc atg acc atg ttc<br>Asn Trp Gly Tyr Trp Asn Leu Asn Pro Lys Gln Phe Met Thr Met Phe<br>415                            420                          425                          430 | 1658 |
| cct cac acc cca gac aac tcc ttc atg ggc ttc gtg tcc gag gag ctc<br>Pro His Thr Pro Asp Asn Ser Phe Met Gly Phe Val Ser Glu Glu Leu<br>                    435                          440                          445 | 1706 |
| aat gag acc gag aag cag ctc atc aaa gat ggc aag gcc agc aac atg<br>Asn Glu Thr Glu Lys Gln Leu Ile Lys Asp Gly Lys Ala Ser Asn Met<br>             450                          455                          460 | 1754 |
| gcg gtg gtg tac ggc aag gag gcg agt atc tgg aag gtg agc aag gag<br>Ala Val Val Tyr Gly Lys Glu Ala Ser Ile Trp Lys Val Ser Lys Glu<br>             465                          470                          475 | 1802 |

TABLE 3-continued

Coding Sequence (SEQ ID NO:3) and Deduced Amino Acid
Sequence (SEQ ID NO:4) for Monse GlcNAc T-Vb

| | | | | | | | | | | | | | | | |
|---|---|---|---|---|---|---|---|---|---|---|---|---|---|---|---|
| aag | ttc | ctg | gcc | gtc | ctc | aac | aag | tac | atg | gag | atc | cac | ggt | acc | gtg | 1850 |
| Lys | Phe | Leu | Ala | Val | Leu | Asn | Lys | Tyr | Met | Glu | Ile | His | Gly | Thr | Val |
| | 480 | | | | 485 | | | | | 490 | | | | | |

| tac | tat | gag | agc | cag | cgg | cca | ccc | gag | gtc | ccc | gcc | ttc | gtg | aag | aac | 1898 |
|---|---|---|---|---|---|---|---|---|---|---|---|---|---|---|---|---|
| Tyr | Tyr | Glu | Ser | Gln | Arg | Pro | Pro | Glu | Val | Pro | Ala | Phe | Val | Lys | Asn |
| 495 | | | | | 500 | | | | | 505 | | | | | 510 |

| cac | ggc | ctc | cta | ccg | cag | cct | gag | ttc | cag | cag | ctg | ctg | cgg | aag | gcc | 1946 |
|---|---|---|---|---|---|---|---|---|---|---|---|---|---|---|---|---|
| His | Gly | Leu | Leu | Pro | Gln | Pro | Glu | Phe | Gln | Gln | Leu | Leu | Arg | Lys | Ala |
| | | | | 515 | | | | | 520 | | | | | 525 | |

| aag | ctc | ttt | ata | ggg | ttc | gga | ttc | ccc | tac | gag | ggc | cca | gca | ccg | ttg | 1994 |
|---|---|---|---|---|---|---|---|---|---|---|---|---|---|---|---|---|
| Lys | Leu | Phe | Ile | Gly | Phe | Gly | Phe | Pro | Tyr | Glu | Gly | Pro | Ala | Pro | Leu |
| | | | 530 | | | | | 535 | | | | | 540 | | |

| gaa | gcc | att | gcc | aat | ggc | tgc | atc | ttc | cta | cag | tct | cgc | ttc | agc | ccg | 2042 |
|---|---|---|---|---|---|---|---|---|---|---|---|---|---|---|---|---|
| Glu | Ala | Ile | Ala | Asn | Gly | Cys | Ile | Phe | Leu | Gln | Ser | Arg | Phe | Ser | Pro |
| | | 545 | | | | | 550 | | | | | 555 | | | |

| ccc | cac | agc | tcc | ctc | aac | cac | gag | ttc | ttc | cgg | ggc | aag | ccc | acc | tcc | 2090 |
|---|---|---|---|---|---|---|---|---|---|---|---|---|---|---|---|---|
| Pro | His | Ser | Ser | Leu | Asn | His | Glu | Phe | Phe | Arg | Gly | Lys | Pro | Thr | Ser |
| | 560 | | | | | 565 | | | | | 570 | | | | |

| agg | gag | gtg | ttc | tcc | cag | cat | ccg | tat | gca | gag | aac | ttt | att | ggc | aag | 2138 |
|---|---|---|---|---|---|---|---|---|---|---|---|---|---|---|---|---|
| Arg | Glu | Val | Phe | Ser | Gln | His | Pro | Tyr | Ala | Glu | Asn | Phe | Ile | Gly | Lys |
| 575 | | | | | 580 | | | | | 585 | | | | | 590 |

| ccg | cac | gtg | tgg | acc | gtg | gac | tat | aac | aac | tcc | gat | gag | ttt | gaa | aca | 2186 |
|---|---|---|---|---|---|---|---|---|---|---|---|---|---|---|---|---|
| Pro | His | Val | Trp | Thr | Val | Asp | Tyr | Asn | Asn | Ser | Asp | Glu | Phe | Glu | Thr |
| | | | | 595 | | | | | 600 | | | | | 605 | |

| gcc | att | aag | gcc | atc | atg | aac | acc | cag | gta | gac | cca | tat | ctg | ccc | tat | 2234 |
|---|---|---|---|---|---|---|---|---|---|---|---|---|---|---|---|---|
| Ala | Ile | Lys | Ala | Ile | Met | Asn | Thr | Gln | Val | Asp | Pro | Tyr | Leu | Pro | Tyr |
| | | 610 | | | | | 615 | | | | | 620 | | | |

| gaa | tat | acc | tgt | gca | ggg | atg | ctg | gaa | cgg | atc | aat | gcc | tac | atc | caa | 2282 |
|---|---|---|---|---|---|---|---|---|---|---|---|---|---|---|---|---|
| Glu | Tyr | Thr | Cys | Ala | Gly | Met | Leu | Glu | Arg | Ile | Asn | Ala | Tyr | Ile | Gln |
| | | 625 | | | | | 630 | | | | | 635 | | | |

| cac | cag | gac | ttc | tgt | gtg | ggt | cca | agc | cct | ctt | cca | cca | ggg | gcc | agc | 2330 |
|---|---|---|---|---|---|---|---|---|---|---|---|---|---|---|---|---|
| His | Gln | Asp | Phe | Cys | Val | Gly | Pro | Ser | Pro | Leu | Pro | Pro | Gly | Ala | Ser |
| | 640 | | | | | 645 | | | | | 650 | | | | |

| act | gcc | cag | agt | cca | ttt | gtc | tta | gct | cct | aat | gca | act | cat | ctc | gag | 2378 |
|---|---|---|---|---|---|---|---|---|---|---|---|---|---|---|---|---|
| Thr | Ala | Gln | Ser | Pro | Phe | Val | Leu | Ala | Pro | Asn | Ala | Thr | His | Leu | Glu |
| 655 | | | | | 660 | | | | | 665 | | | | | 670 |

| tgg | gcc | cag | aac | atc | agc | tca | gtt | ccg | gga | gcc | tgg | ccc | cct | acc | cac | 2426 |
|---|---|---|---|---|---|---|---|---|---|---|---|---|---|---|---|---|
| Trp | Ala | Gln | Asn | Ile | Ser | Ser | Val | Pro | Gly | Ala | Trp | Pro | Pro | Thr | His |
| | | | | 675 | | | | | 680 | | | | | 685 | |

| tct | ctg | cgg | gcc | tgg | ctg | gca | gcc | cct | gga | agg | gcc | tgc | acg | gac | gcc | 2474 |
|---|---|---|---|---|---|---|---|---|---|---|---|---|---|---|---|---|
| Ser | Leu | Arg | Ala | Trp | Leu | Ala | Ala | Pro | Gly | Arg | Ala | Cys | Thr | Asp | Ala |
| | | 690 | | | | | 695 | | | | | 700 | | | |

| tgc | ctg | gac | cat | gga | ttg | atc | tgc | gag | cct | tcc | ttc | ttc | cct | ttc | ctc | 2522 |
|---|---|---|---|---|---|---|---|---|---|---|---|---|---|---|---|---|
| Cys | Leu | Asp | His | Gly | Leu | Ile | Cys | Glu | Pro | Ser | Phe | Phe | Pro | Phe | Leu |
| | | 705 | | | | | 710 | | | | | 715 | | | |

| aac | agc | cag | aat | tcg | ttc | ctc | aag | ctg | cag | gtg | ccc | tgt | gac | agc | act | 2570 |
|---|---|---|---|---|---|---|---|---|---|---|---|---|---|---|---|---|
| Asn | Ser | Gln | Asn | Ser | Phe | Leu | Lys | Leu | Gln | Val | Pro | Cys | Asp | Ser | Thr |
| | 720 | | | | | 725 | | | | | 730 | | | | |

| gag | tgg | gag | atg | cat | cac | ttg | tac | cct | gcc | ttt | gcc | caa | ccc | ggc | caa | 2618 |
|---|---|---|---|---|---|---|---|---|---|---|---|---|---|---|---|---|
| Glu | Trp | Glu | Met | His | His | Leu | Tyr | Pro | Ala | Phe | Ala | Gln | Pro | Gly | Gln |
| 735 | | | | | 740 | | | | | 745 | | | | | 750 |

| gag | tgc | tac | cta | caa | aaa | gag | cca | ctg | ctc | ttc | agc | tgt | gct | ggt | gcc | 2666 |
|---|---|---|---|---|---|---|---|---|---|---|---|---|---|---|---|---|
| Glu | Cys | Tyr | Leu | Gln | Lys | Glu | Pro | Leu | Leu | Phe | Ser | Cys | Ala | Gly | Ala |
| | | | 755 | | | | | 760 | | | | | 765 | | |

| agc | acc | aag | tac | cag | agg | ctc | tgc | ccc | tgc | cgt | gac | ttc | cgc | aag | ggt | 2714 |
|---|---|---|---|---|---|---|---|---|---|---|---|---|---|---|---|---|
| Ser | Thr | Lys | Tyr | Gln | Arg | Leu | Cys | Pro | Cys | Arg | Asp | Phe | Arg | Lys | Gly |
| | | | 770 | | | | | 775 | | | | | 780 | | |

TABLE 3-continued

Coding Sequence (SEQ ID NO:3) and Deduced Amino Acid Sequence (SEQ ID NO:4) for Monse GlcNAc T-Vb

```
cag gtg gcc ttg tgc cag ggc tgc ctg tga ggccggagcc accctgccca      2764
Gln Val Ala Leu Cys Gln Gly Cys Leu
            785                 790 gaacctgccc accegcacgt ggttggcaag caccagcact ttctgagctc cggtcacgct   2824
cactacgtgt ccoctggctg cagcctcccc tggccaggga tgggaagagg aagctgagga   2884
gacagcagct ccaggcctgc agctccctcc tagggcttc  cttgcctcgc cataggacct   2944
gaggccaagc atgtgggctg acctccctgt cgggtgtacc caggagcacg tggatggaga   3004
tccctggctt tctgaggtct ggaccagctg agatgtggc  cttgaccatg cttggaccca   3064
gcataggcct tttgatccac aaggctggga gcatggccat gccgcccct  attcaccaga   3124 ggtctcaagg gatagggaac aggtcacagc cacacttgct gtgagggcca ccctcaca    3184 tgaggcaaca gttcacgcag ggccagtcca gcctcctcag ttgcttgggg ggggggggga   3244
acgacaaagg gacagagagc tcagggaggc tagtgccct  cctgttgct  caaccctgct   3304 tcctccagca gacttccctc tgggcctctc ctgacaccca gttctggcat ggcctgtgac   3364
tggtcc                                                             3370
```

TABLE 4

Alternately-Spliced Coding Sequence (SEQ ID NO:7) and Corresponding Deduced Amino Sequence (SEQ ID NO:8) for Human GlcNAc TR-Vb

```
atg gcc ctt cct gcc ctc ctg acc cgc ctc ctt cct ctc cgc agg ctt    48
Met Ala Leu Pro Ala Leu Leu Thr Arg Leu Leu Pro Leu Arg Arg Leu
1               5                   10                  15 ttt gtc ctg ggc atc ggc ttc ttc act ctc tgc ttc ctg atg acg tct    96
Phe Val Leu Gly Ile Gly Phe Phe Thr Leu Cys Phe Leu Met Thr Ser
                20                  25                  30 ctg gga ggc cag ttc tcg gcc cgg cgc ctg ggg gac tcg cca ttc acc   144
Leu Gly Gly Gln Phe Ser Ala Arg Arg Leu Gly Asp Ser Pro Phe Thr
            35                  40                  45 atc cgc aca gaa gtg atg ggg ggc ccc gag tcc cgc ggc gtc ctg cgc   192
Ile Arg Thr Glu Val Met Gly Gly Pro Glu Ser Arg Gly Val Leu Arg
50                  55                  60 aag atg agc gac ctg ctg gag ctg atg gtg aag cgc atg gac gca ctg   240
Lys Met Ser Asp Leu Leu Glu Leu Met Val Lys Arg Met Asp Ala Leu
65                  70                  75                  80 gcc agg ctg gag aac agc agt gag ctg cac cgg gcc ggc ggc gac ctg   288
Ala Arg Leu Glu Asn Ser Ser Glu Leu His Arg Ala Gly Gly Asp Leu
                85                  90                  95 cac ttt ccc gca gac agg atg ccc cct ggg gcc ggc ctc atg gag cgg   336
His Phe Pro Ala Asp Arg Met Pro Pro Gly Ala Gly Leu Met Glu Arg
            100                 105                 110 atc cag gct att gcc cag aac gtc tcc gac atc gct gtg aag gtg gac   384
Ile Gln Ala Ile Ala Gln Asn Val Ser Asp Ile Ala Val Lys Val Asp
        115                 120                 125 cag atc ctg cgc cac agt ctg ctc ctg cac agc aag gtg tca gaa ggc   432
Gln Ile Leu Arg His Ser Leu Leu Leu His Ser Lys Val Ser Glu Gly
    130                 135                 140 cgg cgg gac cag tgt gag gca ccc agt gac ccc aag ttc cct gac tgc   480
Arg Arg Asp Gln Cys Glu Ala Pro Ser Asp Pro Lys Phe Pro Asp Cys
145                 150                 155                 160
```

TABLE 4-continued

Alternately-Spliced Coding Sequence (SEQ ID NO:7)
and Corresponding Deduced Amino Sequence (SEQ ID NO:8)
for Human GlcNAc TR-Vb

| | |
|---|---:|
| tca ggg aag gtg gag tgg atg cgt gcc cgc tgg acc tct gac ccc tgc<br>Ser Gly Lys Val Glu Trp Met Arg Ala Arg Trp Thr Ser Asp Pro Cys<br>               165                    170                  175 | 528 |
| tac gcc ttc ttt ggg gtg gac ggc acc gag tgc tcc ttc ctc atc tac<br>Tyr Ala Phe Phe Gly Val Asp Gly Thr Glu Cys Ser Phe Leu Ile Tyr<br>          180                    185                    190 | 576 |
| ctc agt gag gtc gag tgg ttc tgc ccc ccg ctg ccc tgg agg aac cag<br>Leu Ser Glu Val Glu Trp Phe Cys Pro Pro Leu Pro Trp Arg Asn Gln<br>       195                  200                    205 | 624 |
| acg gct gcc cag agg gca ccc aag ccc ctc ccc aaa gtc cag gca gtt<br>Thr Ala Ala Gln Arg Ala Pro Lys Pro Leu Pro Lys Val Gln Ala Val<br>    210                  215                    220 | 672 |
| ttc cga agc aac ctg tcc cac ctt ctg gac ctg atg ggc agc ggg aag<br>Phe Arg Ser Asn Leu Ser His Leu Leu Asp Leu Met Gly Ser Gly Lys<br>225                  230                    235                  240 | 720 |
| gag tcc ctg atc ttc atg aag aag cgg acc aag agg ctc aca gcc cag<br>Glu Ser Leu Ile Phe Met Lys Lys Arg Thr Lys Arg Leu Thr Ala Gln<br>                  245                    250                    255 | 768 |
| tgg gcg ctg gct gcc cag cgc ctg gca cag aag ctg ggg gcc acc cag<br>Trp Ala Leu Ala Ala Gln Arg Leu Ala Gln Lys Leu Gly Ala Thr Gln<br>            260                    265                    270 | 816 |
| agg gac cag aag cag atc ctg gtc cac atc ggc ttc ctg acg gag gag<br>Arg Asp Gln Lys Gln Ile Leu Val His Ile Gly Phe Leu Thr Glu Glu<br>        275                    280                    285 | 864 |
| tcc ggg gac gtg ttc agc cct cgg gtc ctg aag ggc ggg ccc cta ggg<br>Ser Gly Asp Val Phe Ser Pro Arg Val Leu Lys Gly Gly Pro Leu Gly<br>            290                    295                    300 | 912 |
| gag atg gtg cag tgg gcg gac att ctg act gca ctc tat gtc ctg ggc<br>Glu Met Val Gln Trp Ala Asp Ile Leu Thr Ala Leu Tyr Val Leu Gly<br>305                  310                    315                  320 | 960 |
| cat ggc ctg cgg gtc aca gtc tcc ctg aag gag ctg cag agt aac tta<br>His Gly Leu Arg Val Thr Val Ser Leu Lys Glu Leu Gln Ser Asn Leu<br>                  325                    330                    335 | 1008 |
| ggg gta ccg cca ggc cgc gga agc tgc ccg ctc acc atg ccc ctg ccc<br>Gly Val Pro Pro Gly Arg Gly Ser Cys Pro Leu Thr Met Pro Leu Pro<br>            340                    345                    350 | 1056 |
| ttc gac ctc atc tac acc gac tac cac ggc ctg cag cag atg aag cgg<br>Phe Asp Leu Ile Tyr Thr Asp Tyr His Gly Leu Gln Gln Met Lys Arg<br>                  355                    360                    365 | 1104 |
| cac atg gga ctc tcc ttc aag aag tac cgg tgc cga atc agg gtc atc<br>His Met Gly Leu Ser Phe Lys Lys Tyr Arg Cys Arg Ile Arg Val Ile<br>            370                    375                    380 | 1152 |
| gac acc ttc ggg acg gaa cct gcg tac aac cac gag gag tac gcc acg<br>Asp Thr Phe Gly Thr Glu Pro Ala Tyr Asn His Glu Glu Tyr Ala Thr<br>385                  390                    395                  400 | 1200 |
| ctg cac ggc tac cgg acc aac tgg ggc tac tgg aac ctc aac ccc aag<br>Leu His Gly Tyr Arg Thr Asn Trp Gly Tyr Trp Asn Leu Asn Pro Lys<br>                  405                    410                    415 | 1248 |
| cag ttc atg acc atg ttt cct cat acc ccc gac aac tcc ttc atg ggc<br>Gln Phe Met Thr Met Phe Pro His Thr Pro Asp Asn Ser Phe Met Gly<br>            420                    425                    430 | 1296 |
| ttc gtg tcc gag gag ctc aac gag acg gag aag cgg ctc atc aaa ggc<br>Phe Val Ser Glu Glu Leu Asn Glu Thr Glu Lys Arg Leu Ile Lys Gly<br>        435                    440                    445 | 1344 |

TABLE 4-continued

Alternately-Spliced Coding Sequence (SEQ ID NO:7)
and Corresponding Deduced Amino Sequence (SEQ ID NO:8)
for Human GlcNAc TR-Vb

```
ggc aag gcc agc aac atg gcc gtg gtg tac ggc aag gag gcg agc atc   1392
Gly Lys Ala Ser Asn Met Ala Val Val Tyr Gly Lys Glu Ala Ser Ile
        450                 455                 460 tgg aag ggg aag gag aag ttc ctg ggc atc ctg aac aaa tac atg gag   1440
Trp Lys Gly Lys Glu Lys Phe Leu Gly Ile Leu Asn Lys Tyr Met Glu
465                 470                 475                 480 atc cat ggc acc gtg tac tac gag agc cag cgg ccc ccc gag gtg cca   1488
Ile His Gly Thr Val Tyr Tyr Glu Ser Gln Arg Pro Pro Glu Val Pro
                485                 490                 495 gcc ttt gtg aag aac cac ggc ctc tta ccg cag cct gag ttt cag cag   1536
Ala Phe Val Lys Asn His Gly Leu Leu Pro Gln Pro Glu Phe Gln Gln
            500                 505                 510 ctg ctg cgc aag gcc aaa ctc ttc atc ggg ttt ggc ttc ccc tac gag   1584
Leu Leu Arg Lys Ala Lys Leu Phe Ile Gly Phe Gly Phe Pro Tyr Glu
        515                 520                 525 ggc ccc gcc ccc ctg gag gcc atc gcc aat ggt tgc atc ttc ctg cag   1632
Gly Pro Ala Pro Leu Glu Ala Ile Ala Asn Gly Cys Ile Phe Leu Gln
530                 535                 540 tcc cgc ttc agc ccg ccc cac agc tcc ctc aac cac gag ttc ttc cga   1680
Ser Arg Phe Ser Pro Pro His Ser Ser Leu Asn His Glu Phe Phe Arg
545                 550                 555                 560 ggc aag ccc acc tcc aga gag gtg ttc tcc cag cat ccc tac gcg gag   1728
Gly Lys Pro Thr Ser Arg Glu Val Phe Ser Gln His Pro Tyr Ala Glu
                565                 570                 575 aac ttc atc ggc aag ccc cac gtg tgg aca gtc gac tac aac aac tca   1776
Asn Phe Ile Gly Lys Pro His Val Trp Thr Val Asp Tyr Asn Asn Ser
            580                 585                 590 gag gag ttt gaa gca gcc atc aag gcc att atg aga act cag gta gac   1824
Glu Glu Phe Glu Ala Ala Ile Lys Ala Ile Met Arg Thr Gln Val Asp
        595                 600                 605 ccc tac cta ccc tac gag tac acc tgc gag ggg atg ctg gag cgg atc   1872
Pro Tyr Leu Pro Tyr Glu Tyr Thr Cys Glu Gly Met Leu Glu Arg Ile
610                 615                 620 cac gcc tac atc cag cac cag gac ttc tgc aga gct cca gac cct gcc   1920
His Ala Tyr Ile Gln His Gln Asp Phe Cys Arg Ala Pro Asp Pro Ala
625                 630                 635                 640 cta cca gag gcc cac gcc ccg cag agc ccc ttt gtc ctg gcc ccc aat   1968
Leu Pro Glu Ala His Ala Pro Gln Ser Pro Phe Val Leu Ala Pro Asn
                645                 650                 655 gcc acc cac ctc gag tgg gct cgg aac acc agc ttg gct cct ggg gcc   2016
Ala Thr His Leu Glu Trp Ala Arg Asn Thr Ser Leu Ala Pro Gly Ala
            660                 665                 670 tgg ccc ccc gcg cac gcc ctg cgg gcc tgg ctg gcc gtg cct ggg agg   2064
Trp Pro Pro Ala His Ala Leu Arg Ala Trp Leu Ala Val Pro Gly Arg
        675                 680                 685 gcc tgc acc gac acc tgc ctg gac cac ggg cta atc tgt gag ccc tcc   2112
Ala Cys Thr Asp Thr Cys Leu Asp His Gly Leu Ile Cys Glu Pro Ser
690                 695                 700 ttc ttc ccc ttc ctg aac agc cag gac gcc ttc ctc aag ctg cag gtg   2160
Phe Phe Pro Phe Leu Asn Ser Gln Asp Ala Phe Leu Lys Leu Gln Val
705                 710                 715                 720 ccc tgt gac agc acc gag tcg gag atg aac cac ctg tac ccg gcg ttc   2208
Pro Cys Asp Ser Thr Glu Ser Glu Met Asn His Leu Tyr Pro Ala Phe
                725                 730                 735
```

TABLE 4-continued

Alternately-Spliced Coding Sequence (SEQ ID NO:7)
and Corresponding Deduced Amino Sequence (SEQ ID NO:8)
for Human GlcNAc TR-Vb

| | |
|---|---|
| gcc cag cct ggc cag gag tgc tac ctg cag aag gag cct ctg ctc ttc<br>Ala Gln Pro Gly Gln Glu Cys Tyr Leu Gln Lys Glu Pro Leu Leu Phe<br>740 745 750 | 2256 |
| agc tgc gcc ggc tcc aac acc aag tac cgc cgg ctc tgc ccc tgc cgc<br>Ser Cys Ala Gly Ser Asn Thr Lys Tyr Arg Arg Leu Cys Pro Cys Arg<br>755 760 765 | 2304 |
| gac ttc cgc aag ggc cag gtg gcc ttg tgc cag ggc tgt ctg tga<br>Asp Phe Arg Lys Gly Gln Val Ala Leu Cys Gln Gly Cys Leu<br>770 775 780 | 2349 |

TABLE 5

Alternative Coding Sequence (SEQ ID NO:9) and Corresponding
Deduced Amino Acid Sequence (SEQ ID No:10) for
Human GlcNAc T-Vb

| | |
|---|---|
| atg gcc ctt cct gcc ctc ctg acc cgc ctc ctt cct ctc cgc agg ctt<br>Met Ala Leu Pro Ala Leu Leu Thr Arg Leu Leu Pro Leu Arg Arg Leu<br>1 5 10 15 | 48 |
| ttt gtc ctg ggc atc ggc ttc ttc act ctc tgc ttc ctg atg acg tct<br>Phe Val Leu Gly Ile Gly Phe Phe Thr Leu Cys Phe Leu Met Thr Ser<br>20 25 30 | 96 |
| ctg gga ggc cag ttc tcg gcc cgg cgc ctg ggg gac tcg cca ttc acc<br>Leu Gly Gly Gln Phe Ser Ala Arg Arg Leu Gly Asp Ser Pro Phe Thr<br>35 40 45 | 144 |
| atc cgc aca gaa gtg atg ggg ggc ccc gag tcc cgc ggc gtc ctg cgc<br>Ile Arg Thr Glu Val Met Gly Gly Pro Glu Ser Arg Gly Val Leu Arg<br>50 55 60 | 192 |
| aag atg agc gac ctg ctg gag ctg atg gtg aag cgc atg gac gca ctg<br>Lys Met Ser Asp Leu Leu Glu Leu Met Val Lys Arg Met Asp Ala Leu<br>65 70 75 80 | 240 |
| gcc agg ctg gag aac agc agt gag ctg cac cgg gcc ggc ggc gac ctg<br>Ala Arg Leu Glu Asn Ser Ser Glu Leu His Arg Ala Gly Gly Asp Leu<br>85 90 95 | 288 |
| cac ttt ccc gca gac agg atg ccc cct ggg gcc ggc ctc atg gag cgg<br>His Phe Pro Ala Asp Arg Met Pro Pro Gly Ala Gly Leu Met Glu Arg<br>100 105 110 | 336 |
| atc cag gct att gcc cag aac gtc tcc gac atc gct gtg aag gtg gac<br>Ile Gln Ala Ile Ala Gln Asn Val Ser Asp Ile Ala Val Lys Val Asp<br>115 120 125 | 384 |
| cag atc ctg cgc cac agt ctg ctc ctg cac agc aag gtg tca gaa ggc<br>Gln Ile Leu Arg His Ser Leu Leu Leu His Ser Lys Val Ser Glu Gly<br>130 135 140 | 432 |
| cgg cgg gac cag tgt gag gca ccc agt gac ccc aag ttc cct gac tgc<br>Arg Arg Asp Gln Cys Glu Ala Pro Ser Asp Pro Lys Phe Pro Asp Cys<br>145 150 155 160 | 480 |
| tca ggg aag gtg gag tgg atg cgt gcc cgc tgg acc tct gac ccc tgc<br>Ser Gly Lys Val Glu Trp Met Arg Ala Arg Trp Thr Ser Asp Pro Cys<br>165 170 175 | 528 |
| tac gcc ttc ttt ggg gtg gac ggc acc gag tgc tcc ttc ctc atc tac<br>Tyr Ala Phe Phe Gly Val Asp Gly Thr Glu Cys Ser Phe Leu Ile Tyr<br>180 185 190 | 576 |
| ctc agt gag gtc gag tgg ttc tgc ccc ccg ctg ccc tgg agg aac cag<br>Leu Ser Glu Val Glu Trp Phe Cys Pro Pro Leu Pro Trp Arg Asn Gln<br>195 200 205 | 624 |

TABLE 5-continued

Alternative Coding Sequence (SEQ ID NO:9) and Corresponding
Deduced Amino Acid Sequence (SEQ ID No:10) for
Human GlcNAc T-Vb

| | |
|---|---|
| acg gct gcc cag agg gca ccc aag ccc ctc ccc aaa gtc cag gca gtt<br>Thr Ala Ala Gln Arg Ala Pro Lys Pro Leu Pro Lys Val Gln Ala Val<br>210                        215                        220 | 672 |
| ttc cga agc aac ctg tcc cac ctt ctg gac ctg atg ggc agc ggg aag<br>Phe Arg Ser Asn Leu Ser His Leu Leu Asp Leu Met Gly Ser Gly Lys<br>225                        230                        235                        240 | 720 |
| gag tcc ctg atc ttc atg aag aag cgg acc aag agg ctc aca gcc cag<br>Glu Ser Leu Ile Phe Met Lys Lys Arg Thr Lys Arg Leu Thr Ala Gln<br>                        245                        250                        255 | 768 |
| tgg gcg ctg gct gcc cag cgc ctg gca cag aag ctg ggg gcc acc cag<br>Trp Ala Leu Ala Ala Gln Arg Leu Ala Gln Lys Leu Gly Ala Thr Gln<br>                260                        265                        270 | 816 |
| agg gac cag aag cag atc ctg gtc cac atc ggc ttc ctg acg gag gag<br>Arg Asp Gln Lys Gln Ile Leu Val His Ile Gly Phe Leu Thr Glu Glu<br>                275                        280                        285 | 864 |
| tcc ggg gac gtg ttc agc cct cgg gtc ctg aag ggc ggg ccc cta ggg<br>Ser Gly Asp Val Phe Ser Pro Arg Val Leu Lys Gly Gly Pro Leu Gly<br>290                        295                        300 | 912 |
| gag atg gtg cag tgg gcg gac att ctg act gca ctc tat gtc ctg ggc<br>Glu Met Val Gln Trp Ala Asp Ile Leu Thr Ala Leu Tyr Val Leu Gly<br>305                        310                        315                        320 | 960 |
| cat ggc ctg cgg gtc aca gtc tcc ctg aag gag ctg cag agt aac tta<br>His Gly Leu Arg Val Thr Val Ser Leu Lys Glu Leu Gln Ser Asn Leu<br>                325                        330                        335 | 1008 |
| ggg gta ccg cca ggc cgg gga agc tgc ccg ctc acc atg ccc ctg ccc<br>Gly Val Pro Pro Gly Arg Gly Ser Cys Pro Leu Thr Met Pro Leu Pro<br>                340                        345                        350 | 1056 |
| ttc gac ctc atc tac acc gac tac cac ggc ctg cag cag atg aag cgg<br>Phe Asp Leu Ile Tyr Thr Asp Tyr His Gly Leu Gln Gln Met Lys Arg<br>                355                        360                        365 | 1104 |
| cac atg gga ctc tcc ttc aag aag tac cgg tgc cga atc agg gtc atc<br>His Met Gly Leu Ser Phe Lys Lys Tyr Arg Cys Arg Ile Arg Val Ile<br>        370                        375                        380 | 1152 |
| gac acc ttt ggg acg gaa cct gcg tac aac cac gag gag tac gcc acg<br>Asp Thr Phe Gly Thr Glu Pro Ala Tyr Asn His Glu Glu Tyr Ala Thr<br>385                        390                        395                        400 | 1200 |
| ctg cac ggc tac cgg acc aac tgg ggc tac tgg aac ctc aac ccc aag<br>Leu His Gly Tyr Arg Thr Asn Trp Gly Tyr Trp Asn Leu Asn Pro Lys<br>                405                        410                        415 | 1248 |
| cag ttc atg acc atg ttt cct cat acc ccc gac aac tcc ttc atg ggc<br>Gln Phe Met Thr Met Phe Pro His Thr Pro Asp Asn Ser Phe Met Gly<br>                420                        425                        430 | 1296 |
| ttt gtg tcc gag gag ctc aac gag acg gag aag cgg ctc atc aaa ggc<br>Phe Val Ser Glu Glu Leu Asn Glu Thr Glu Lys Arg Leu Ile Lys Gly<br>                435                        440                        445 | 1344 |
| ggc aag gcc agc aac atg gcc gtg gtg tac ggc aag gag gcg agc atc<br>Gly Lys Ala Ser Asn Met Ala Val Val Tyr Gly Lys Glu Ala Ser Ile<br>    450                        455                        460 | 1392 |
| tgg aag ctc cag ggg aag gag aag ttc ctg ggc atc ctg aac aaa tac<br>Trp Lys Leu Gln Gly Lys Glu Lys Phe Leu Gly Ile Leu Asn Lys Tyr<br>465                        470                        475                        480 | 1440 |
| atg gag atc cat ggc acc gtg tac tac gag agc cag cgg ccc ccc gag<br>Met Glu Ile His Gly Thr Val Tyr Tyr Glu Ser Gln Arg Pro Pro Glu<br>                485                        490                        495 | 1488 |

TABLE 5-continued

Alternative Coding Sequence (SEQ ID NO:9) and Corresponding
Deduced Amino Acid Sequence (SEQ ID No:10) for
Human GlcNAc T-Vb

| | |
|---|---:|
| gtg cca gcc ttt gtg aag aac cac ggc ctc tta ccg cag cct gag ttt<br>Val Pro Ala Phe Val Lys Asn His Gly Leu Leu Pro Gln Pro Glu Phe<br>           500                  505                    510 | 1536 |
| cag cag ctg ctg cgc aag gcc aaa ctc ttc atc ggg ttt ggc ttc ccc<br>Gln Gln Leu Leu Arg Lys Ala Lys Leu Phe Ile Gly Phe Gly Phe Pro<br>       515                  520                  525 | 1584 |
| tac gag ggc ccc gcc ccc ctg gag gcc atc gcc aat ggt tgc atc ttc<br>Tyr Glu Gly Pro Ala Pro Leu Glu Ala Ile Ala Asn Gly Cys Ile Phe<br>530                     535                  540 | 1632 |
| ctg cag tcc cgc ttc agc cca ccc agc tcc ctc aac cac gag ttc<br>Leu Gln Ser Arg Phe Ser Pro Pro His Ser Ser Leu Asn His Glu Phe<br>545                     550                  555                  560 | 1680 |
| ttc cga ggc aag ccc acc tcc aga gag gtg ttc tcc cag cat ccc tac<br>Phe Arg Gly Lys Pro Thr Ser Arg Glu Val Phe Ser Gln His Pro Tyr<br>                    565                  570                  575 | 1728 |
| gcg gag aac ttc atc ggc aag ccc cac gtg tgg aca gtc gac tac aac<br>Ala Glu Asn Phe Ile Gly Lys Pro His Val Trp Thr Val Asp Tyr Asn<br>                580                  585                  590 | 1776 |
| aac tca gag gag ttt gaa gca gcc atc aag gcc att atg aga act cag<br>Asn Ser Glu Glu Phe Glu Ala Ala Ile Lys Ala Ile Met Arg Thr Gln<br>         595                  600                  605 | 1824 |
| gta gac ccc tac cta ccc tat gag tac acc tgc gag ggg atg ctg gag<br>Val Asp Pro Tyr Leu Pro Tyr Glu Tyr Thr Cys Glu Gly Met Leu Glu<br>610                     615                  620 | 1872 |
| cgg atc cac gcc tac atc cag cac cag gac ttc tgc aga gct cca gac<br>Arg Ile His Ala Tyr Ile Gln His Gln Asp Phe Cys Arg Ala Pro Asp<br>625                     630                  635                  640 | 1920 |
| cct gcc cta cca gag gcc cac gcc ccg cag agc ccc ttt gtc ctg gcc<br>Pro Ala Leu Pro Glu Ala His Ala Pro Gln Ser Pro Phe Val Leu Ala<br>                645                  650                  655 | 1968 |
| ccc aat gcc acc cac ctc gag tgg gct cgg aac acc agc ttg gct cct<br>Pro Asn Ala Thr His Leu Glu Trp Ala Arg Asn Thr Ser Leu Ala Pro<br>                660                  665                  670 | 2016 |
| ggg gcc tgg ccc ccc gcg cac gcc ctg cgg gcc tgg ctg gcc gtg cct<br>Gly Ala Trp Pro Pro Ala His Ala Leu Arg Ala Trp Leu Ala Val Pro<br>             675                  680                  685 | 2064 |
| ggg agg gcc tgc acc gac acc tgc ctg gac cac ggg cta atc tgt gag<br>Gly Arg Ala Cys Thr Asp Thr Cys Leu Asp His Gly Leu Ile Cys Glu<br>       690                  695                  700 | 2112 |
| ccc tcc ttc ttc ccc ttc ctg aac agc cag gac gcc ttc ctc aag ctg<br>Pro Ser Phe Phe Pro Phe Leu Asn Ser Gln Asp Ala Phe Leu Lys Leu<br>705                   710                  715                  720 | 2160 |
| cag gtg ccc tgt gac agc acc gag tcg gag atg aac cac ctg tac ccg<br>Gln Val Pro Cys Asp Ser Thr Glu Ser Glu Met Asn His Leu Tyr Pro<br>                    725                  730                  735 | 2208 |
| gcg ttc gcc cag cct ggc cag gag tgc tac ctg cag aag gag cct ctg<br>Ala Phe Ala Gln Pro Gly Gln Glu Cys Tyr Leu Gln Lys Glu Pro Leu<br>             740                  745                  750 | 2256 |
| ctc ttc agc tgc gcc ggc tcc aac acc aag tac cgc cgg ctc tgc ccc<br>Leu Phe Ser Cys Ala Gly Ser Asn Thr Lys Tyr Arg Arg Leu Cys Pro<br>       755                  760                  765 | 2304 |
| tgc cgc gac ttc cgc aag ggc cag gtg gcc ttg tgc cag ggc tgt ctg<br>Cys Arg Asp Phe Arg Lys Gly Gln Val Ala Leu Cys Gln Gly Cys Leu<br>770                     775                  780 | 2352 |
| tga | 2355 |

TABLE 7

Human GnT-Vb variant DNA sequence ctgctcgcaccaacaagtttgaaca

ATGatcaccgtcaaccccgatgggaagataatggtcagaagatgcctggtcaccc tgagacccttcggcttttgtcctgggcatcggcttcttcactctctgcttcctgatgacgtctctgggaggccagttc tcggcccggcgcctggggactcgccattcaccatccgcacagaagtgatgggggccccgagtccgcggcgtcctgcg caagatgagcgacctgctggagctgatggtgaagcgcatggacgcactggccaggctggagaacagcagtgagctgcacc gggccggcggcgacctgcactttcccgcagacaggatgcccctggggccggcctcatggagcggatccaggctattgcc cagaacgtctccgacatcgctgtgaaggtggaccagatcctgcgccacagtctgctcctgcacagcaaggtgtcagaagg ccggcgggaccagtgtgaggcacccagtgaccccaagttccctgactgctcagggaaggtggagtggatgcgtgcccgct ggacctctgaccccgctacgccttctttggggtggacggcaccgagtgctccttcctcatctacctcagtgaggtcgag tggttctgccccccgctgccctggaggaaccagacggctgcccagagggcacccaagcccctccccaaagtccaggcagt tttccgaagcaacctgtcccaccttctggacctgatgggcagcgggaaggagtccctgatcttcatgaagaagcggacca agaggctcacagcccagtgggcgctggctgcccagcgcctggcacagaagctgggggccacccagagggaccagaagcag atcctggtccacatcggcttcctgacggaggagtccggggacgtgttcagccctcgggtcctgaagggcgggcccctagg ggagatggtgcagtgggcggacattctgactgcactctatgtcctgggccatggcctgcgggtcacagtctccctgaagg agctgcagagtaacttaggggtaccgccaggccggggaagctgcccgctcaccatgcccctgcccttcgacctcatctac accgactaccacggcctgcagcagatgaagcggcacatgggactctccttcaagaagtaccggtgccgaatcagggtcat cgacaccttcgggacggaacctgcgtacaaccacgaggagtacgccacgctgcacggctaccggaccaactgggctact ggaacctcaaccccaagcagttcatgaccatgtttcctcataccccgacaactccttcatgggcttcgtgtccgaggag ctcaacgagacggagaagcggctcatcaaaggcggcaaggccagcaacatggccgtggtgtacggcaaggaggcgagcat ctggaagctccaggggaaggagaagttcctgggcatcctgaacaaatacatggagatccatggcaccgtgtactacgaga gccagcggcccccgaggtgccagcctttgtgaagaaccacggcctcttaccgcagcctgagtttcagcagctgctgcgc aaggccaaactcttcatcgggtttggcttcccctacgagggccccgcccccctggaggccatcgccaatggttgcatctt cctgcagtcccgcttcagcccgccccacagctccctcaaccacgagttcttccgaggcaagcccacctccagagaggtgt tctcccagcatccctacgcggagaacttcatcggcaagccccacgtgtggacagtcgactacaacaactcagaggagttt gaagcagccatcaaggccattatgagaactcaggtagaccctacctacctatgagtacacctgcgaggggatgctgga gcggatccacgcctacatccagcaccaggacttctgcagagctccagaccctgccctaccagaggccacgccccgcaga gccccttgtcctggcccccaatgccacccacctcgagtgggctcggaacaccagcttggctcctggggcctggccccc gcgcacgccctgcgggcctggctggccgtgcctggggaggcctgcaccgacacctgcctggaccacgggctaatctgtga gccctccttcttcccctcctgaacagccaggacgccttcctcaagctgcaggtgccctgtgacagcaccgagtcggaga tgaaccacctgtacccggcgttcgcccagcctggccaggagtgctacctgcagaaggagcctctgctcttcagctgcgcc ggctccaacaccaagtaccgccggctctgcccctgccgcgacttccgcaagggccaggtggccttgtgccagggctgtct gtgaatccgcctctgccgccctgcctggcacccacgctggctctctcctgccgcgggagaaagcaccagcaggttc

TABLE 8

Human GnT-Vb variant protein sequence

MITVNPDGKIMVRRCLVTLRPFRLFVLGIGFFTLCFLMTSLGGQFSARRLGDSPFTIRTEVMGGPESRGVLRKMSDLLEL

MVKRMDALARLENSSELHRAGGDLHFPADRMPPGAGLMERIQAIAQNVSDIAVKVDQILRHSLLLHSKVSEGRRDQCEAP

SDPKFPDCSGKVEWMRARWTSDPCYAFFGVDGTECSFLIYLSEVEWFCPPPLPWRNQTAAQRAPKPLPKVQAVFRSNLSHL

TABLE 8-continued

Human GnT-Vb variant protein sequence

LDLMGSGKESLIFMKKRTKRLTAQWALAAQRLAQKLGATQRDQKQILVHIGFLTEESGDVFSPRVLKGGPLGEMVQWADI

LTALYVLGHGLRVTVSLKELQSNLGVPPGRGSCPLTMPLPFDLIYTDYHGLQQMKRHMGLSFKKYRCRIRVIDTFGTEPA

YNHEEYATLHGYRTNWGYWNLNPKQFMTMFPHTPDNSFMGFVSEELNETEKRLIKGGKASNMAVVYGKEASIWKLQGKEK

FLGILNKYMEIHGTVYYESQRPPEVPAFVKNHGLLPQPEFQQLLRKAKLFIGFGFPYEGPAPLEAIANGCIFLQSRFSPP

HSSLNHEFFRGKPTSREVFSQHPYAENFIGKPHVWTVDYNNSEEFEAAIKAIMRTQVDPYLPYEYTCEGMLERIHAYIQH

QDFCRAPDPALPEAHAPQSPFVLAPNATHLEWARNTSLAPGAWPPAHALRAWLAVPGRACTDTCLDHGLICEPSFFPFLN

SQDAFLKLQVPCDSTESEMNHLYPAFAQPGQECYLQKEPLLFSCAGSNTKYRRLCPCRDFRKGQVALCQGCL

TABLE 6

Comparison of Partial Human GNTVb and Mouse GNTVb Amino Acid Sequences

Gap Weight: 8 Average Match: 2.778

Length Weight: 2 Average Mismatch: -2.248

Quality: 1099 Length: 225

Ratio: 4.884 Gaps: 0

Percent Similarity: 92.444 Percent Identity: 90.667

Match display thresholds for the alignment(s):

| = IDENTITY

: = 2

. = 1 mousentv.pep x newgntvC.pep

```
  1 ARWTSDPCYAFFGVDGTECSFLIYLSEVEWFCPPLPWRNQTAARTAPKSL   50
    |||||||||||||||||||||||||||||||||||||||||.||| ||| |
169 ARWTSDPCYAFFGVDGTECSFLIYLSEVEWFCPPLPWRNQTAAQRAPKPL  218

51 PRVQAVFRSNLSHLLELMGSGKESLIFMKKRTRRFTAQWTKAAKYLAQKL  100
    |:|||||||||||||:||||  ||||| |||||:| ||||  ||. |||
219 PKVQAVFRSNLSHLLDLMGSGKESLIFMKKRTKRLTAQWALAAQRLAQKL  268

101 GDIRRDQKQILVHIGFLTEESGDVFSPRVLKGGPLGEMVQWADILAALYV  150
    |.||||||||||||||||||||||||||||||||||||||||||  |||
269 GATQRDQKQILVHIGFLTEESGDVFSPRVLKGGPLGEMVQWADILTALYV  318

151 LGHSLRITVSLKELQSNLGVPPGRGNCPLTVPLPFDLIYTDYHGLQQMKQ  200
    |||  ||:|||||||||||||||||.||||.||||||||||||||||||.
319 LGHGLRVTVSLKELQSNLGVPPGRGSCPLTMPLPFDLIYTDYHGLQQMKR  368

201 HMGLSFxKYRCRIRVIDTFGTEPAY                          225
    ||||||  |||||||||||||||||
369 HMGLSFKKYRCRIRVIDTFGTEPAY                          393
```

We claim:

1. An isolated DNA molecule comprising a nucleotide sequence encoding a polypeptide having N-acetylglucosaminyl transferase V activity, said nucleotide sequence having at least 95% homology with a nucleotide sequence given in SEQ ID NO:7.

2. The DNA molecule of claim 1, wherein said nucleotide sequence encodes human GlcNAc T-Vb.

3. The DNA molecule of claim 2, wherein said nucleotide sequence encodes a polypeptide having the amino acid sequence given in SEQ ID NO:8.

4. The DNA molecule of claim 3, wherein said nucleotide sequence is given in SEQ ID NO:7.

5. A DNA molecule comprising the DNA sequence of claim 1 and further comprising an exogenous nucleotide sequence.

6. The DNA molecule of claim 5, wherein said exogenous nucleotide sequence is an expression vector.

7. An isolated recombinant host cell comprising the DNA molecule of claim 1.

8. The recombinant cell of claim 7, wherein said cell is a bacterial cell.

9. The recombinant cell of claim 8, wherein said bacterial cell is *Escherichia coli*.

10. The recombinant cell of claim 7, wherein said cell is a mammalian cell.

11. The recombinant cell of claim 10, wherein said cell is selected from the group consisting of a COS-7 cell, a HEK-293 cell and a 3T3 cell.

12. The recombinant cell of claim 7, wherein said cell is an insect cell, a yeast cell or a fungal cell.

13. An isolated recombinant host cell comprising the DNA molecule of claim 3.

14. The recombinant cell of claim 13, wherein said cell is a bacterial cell.

15. The recombinant cell of claim 14, wherein said bacterial cell is *Escherichia coli*.

16. The recombinant cell of claim 13, wherein said cell is a mammalian cell.

17. The recombinant cell of claim 16, wherein said cell is selected from the group consisting of a COS-7 cell, a HEK-293 cell and a 3T3 cell.

18. The recombinant cell of claim 13, wherein said cell is an insect cell, a yeast cell or a fungal cell.

19. A method of producing a polypeptide having N-Acetylglucosaminyl transferase V-b activity, said method comprising the step of culturing the recombinant cell of claim 7 under conditions for expression of said GlcNAc T-Vb.

20. A method of producing a polypeptide having N-Acetylglucosaminyl transferase V-b activity, said method comprising the step of culturing the recombinant cell of claim 13 under conditions for expression of said GlcNAc T-Vb.

* * * * *